(12) United States Patent
Miyazono et al.

(10) Patent No.: US 8,080,639 B2
(45) Date of Patent: Dec. 20, 2011

(54) ANTIBODIES WHICH BIND SPECIFICALLY TO ACTIVIN RECEPTOR LIKE KINASE 3

(75) Inventors: Kohei Miyazono, Uppsala (SE); Peter ten Dijke, Uppsala (SE); Petra Franzen, Uppsala (SE); Hidetoshi Yamashita, Uppsala (SE); Carl-Henrik Heldin, Uppsala (SE)

(73) Assignee: Ludwig Institute for Cancer Research, New York, NY (US)

( * ) Notice: Subject to any disclaimer, the term of this patent is extended or adjusted under 35 U.S.C. 154(b) by 1082 days.

(21) Appl. No.: 11/981,260

(22) Filed: Oct. 31, 2007

(65) Prior Publication Data

US 2010/0330657 A1    Dec. 30, 2010

Related U.S. Application Data

(60) Continuation of application No. 11/656,720, filed on Jan. 23, 2007, now Pat. No. 7,932,351, which is a division of application No. 10/630,555, filed on Jul. 30, 2003, now Pat. No. 7,592,428, which is a division of application No. 09/903,068, filed on Jul. 11, 2001, now Pat. No. 6,982,319, which is a division of application No. 09/679,187, filed on Oct. 3, 2000, now Pat. No. 6,331,621, which is a division of application No. 08/436,265, filed as application No. PCT/GB93/02367 on Nov. 17, 1993, now Pat. No. 6,316,217.

(30) Foreign Application Priority Data

| Nov. 17, 1992 | (GB) | 9224057.1 |
| Mar. 8, 1993 | (GB) | 9304677.9 |
| Mar. 8, 1993 | (GB) | 9304680.3 |
| May 28, 1993 | (GB) | 9311047.6 |
| Jul. 2, 1993 | (GB) | 9313763.6 |
| Aug. 3, 1993 | (GB) | 9136099.2 |
| Oct. 15, 1993 | (GB) | 9321344.5 |

(51) Int. Cl.
*C07K 16/28* (2006.01)
*C07K 14/00* (2006.01)
*A61K 39/395* (2006.01)

(52) U.S. Cl. ............... 530/388.22; 530/350; 424/144.1

(58) Field of Classification Search .................. None
See application file for complete search history.

*Primary Examiner* — Robert Landsman
*Assistant Examiner* — Bruce D Hissong
(74) *Attorney, Agent, or Firm* — Abelman, Frayne & Schwab

(57) ABSTRACT

A new receptor family has been identified, of activin-like kinases. Novel proteins have activin/TGF-β-type I receptor functionality, and have consequential diagnostic/therapeutic utility. They may have a serine/threonine kinase domain, a DFKSRN or DLKSKN sequence in subdomain VIB and/or a GTKRYM sequence in subdomain VIII.

4 Claims, 11 Drawing Sheets

```
cons.aa         G G   G V                    A K                   E
hTGFBR-II    LDTLVGKGRFAEVYKAKLKQNTSEQFETVAVKIFPYDHYASWKDRKDIFSDINLKHENILQF
mActR-IIB    LLEIKARGRFGCVWKAQLMN------DFVAVKIKPLQDKQSWQSEREIFSTPGMKHENLLQF
mActR-II     LLEVKARGRFGCVWKAQLLN------EYVAVKIFPIQDKQSWQNEYEVYSIPGMKHENILQF
daf-1        LFURVGSGRFGNVSRGDYRG------EAVAVKVFNAIDEPAFHKEIEIFETRMLRHPNVLRY
subdomains         I                    II      III            IV hTGFBR-II    LTAEERKTELGKQYWLITAFHAKGNLQEYLTRHVISWEDLRNVGSSLARGLSHLHSDHTP·C
mActR-IIB    IAAEKRGSNLEVELWLITAFHDKGSLIDYLKGNIITWNELCHVAETMSRGISYLHEDVPWCR
mActR-II     IGAEKRGTSVDVDLWLITAFHEKGSLSDFLKANVVSWNELCHIAETMARGLAYLHEDIPGLK
daf-1        IGSDRVDTGFVTELWLVIEYHPSGSLHDFLLENTVNIETYYNLMRSTASGLAFLHNQIGGSK
subdomains                          V                         VI-A cons.aa            DLK  N             DFG
hTGFBR-II    ·GRPKMPIVHRDLKSSNILVKNDLTCCLCDFGLSLRL···GPYSSVDDLANSGQVGTARYMAP
mActR-IIB    GEGHKPSIAHRDFKSKNVLLKSDLTAVLADFGLAVRF···EPGKPPGD··THGQVGTRRYMAP
mActR-II     ·DGHKPAISHRDIKSKNVLLKNNLTACIADFGLALKF···EAGKSAGD··THGQVGTRRYMAP
daf-1        ·ESHKPAMAHRDIKSKNIMYKNDLTCAIGDLGLSLSKPEDAASDIIAN··ENYKCGTVRYLAP
subdomains       VI-B                  VII                  VIII
```

Fig. 1

```
a.a        C  C  E  G  N  M  C
5' GCGGATCCTGTTGTGAAGGNAATATGTG 3'   Fig. 2A
      BAMHI  C  C  G     C
```

```
a.a        V  A  V  K  I  F
5' GCGGATCCGTCGCAGTCAAAATTTT 3'      Fig. 2B
      BamHI    G  C  G  G  C
               T  T  T     A
```

```
a.a        R  D  I  K  S  K  N
5' GCGGATCCGCGATATTAAAAGCAA 3'       Fig. 2C
      BAMHI    A  C  C  GTCT
               G     A
```

```
a.a        E  P  A  M  Y
5' CGGAATTCTGGTGCCATATA                Fig. 2D
      EcoRI G  G     G
            A  A
```

Fig. 3

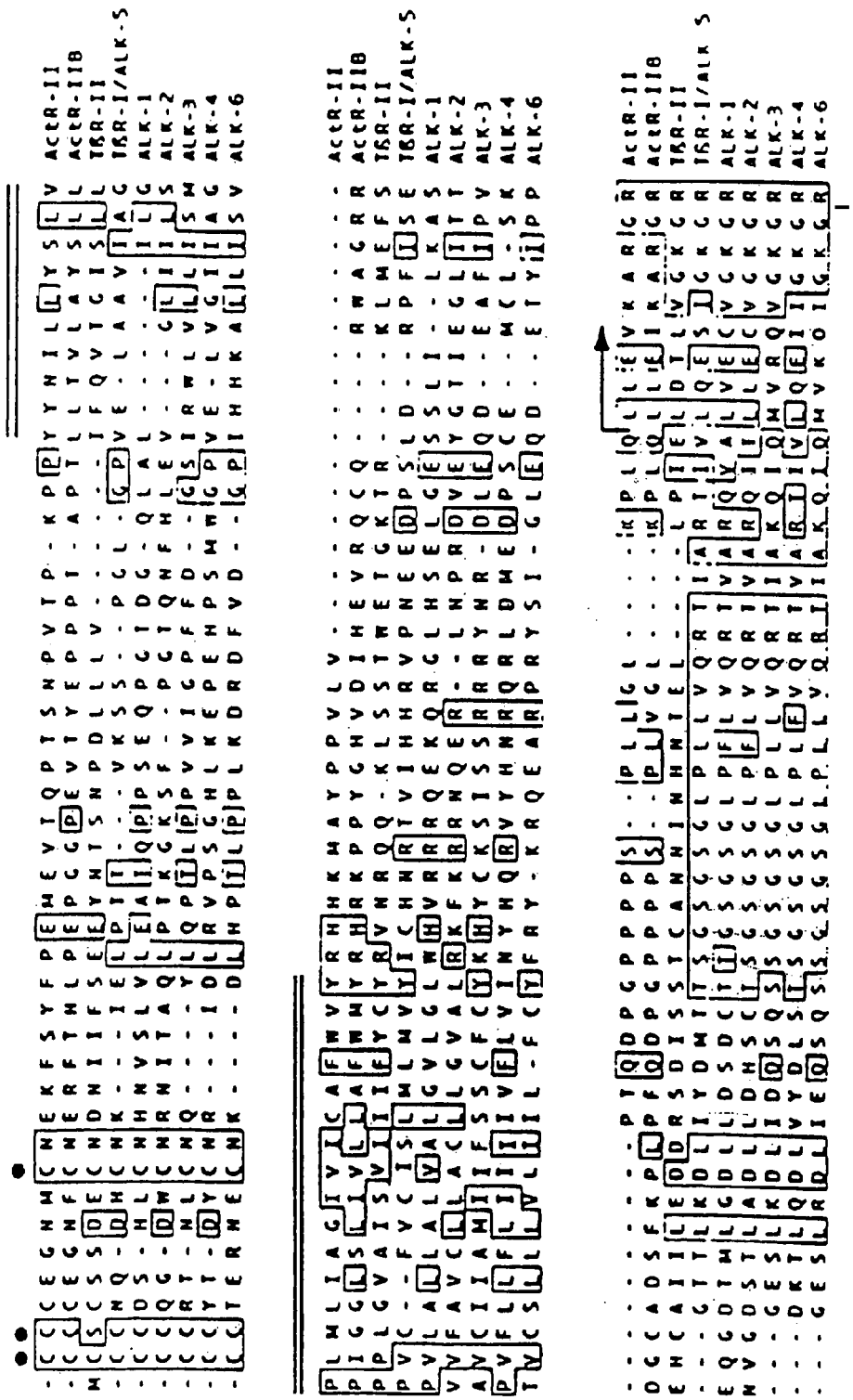
Fig. 3 contd.

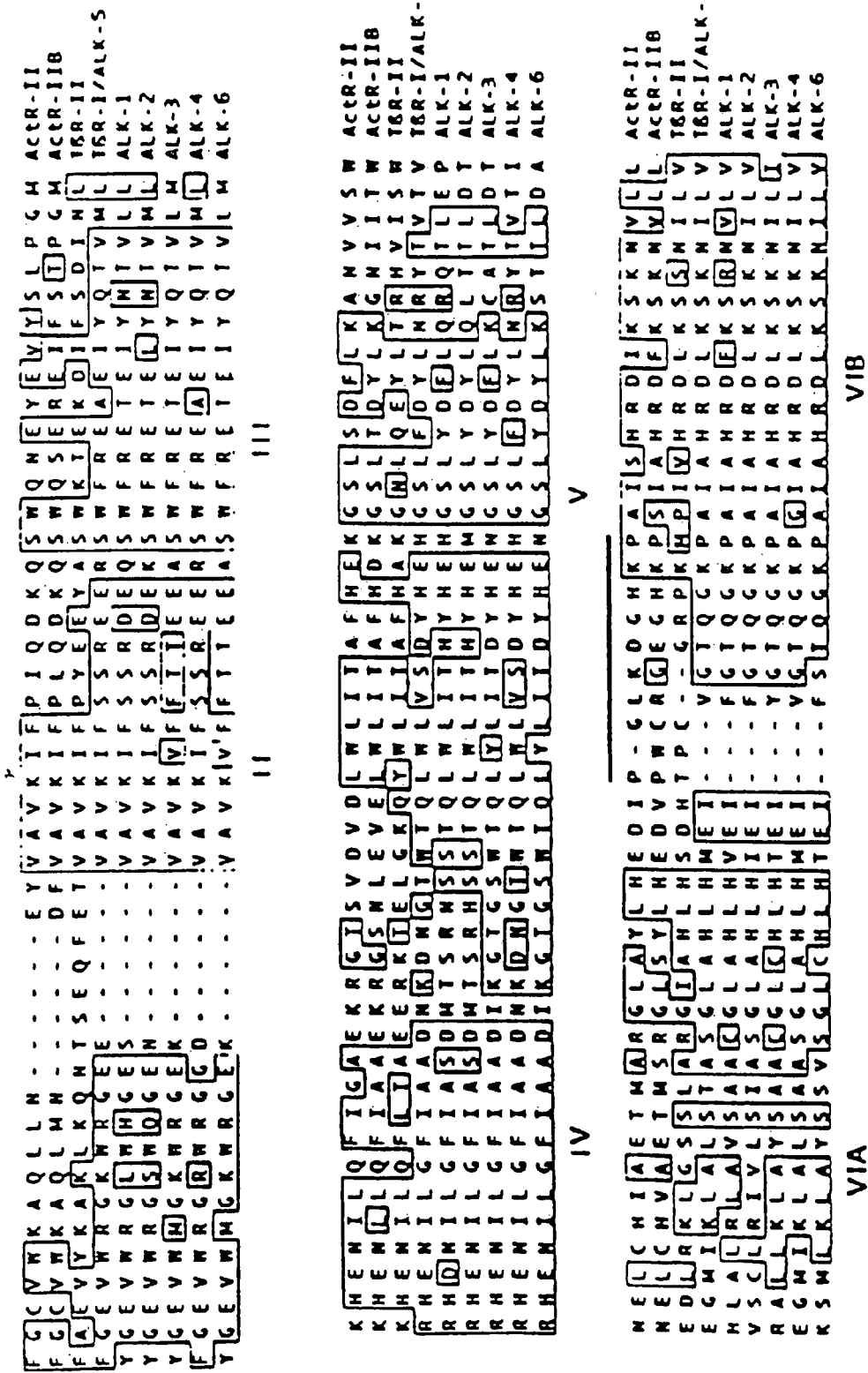
Fig. 3 contd.

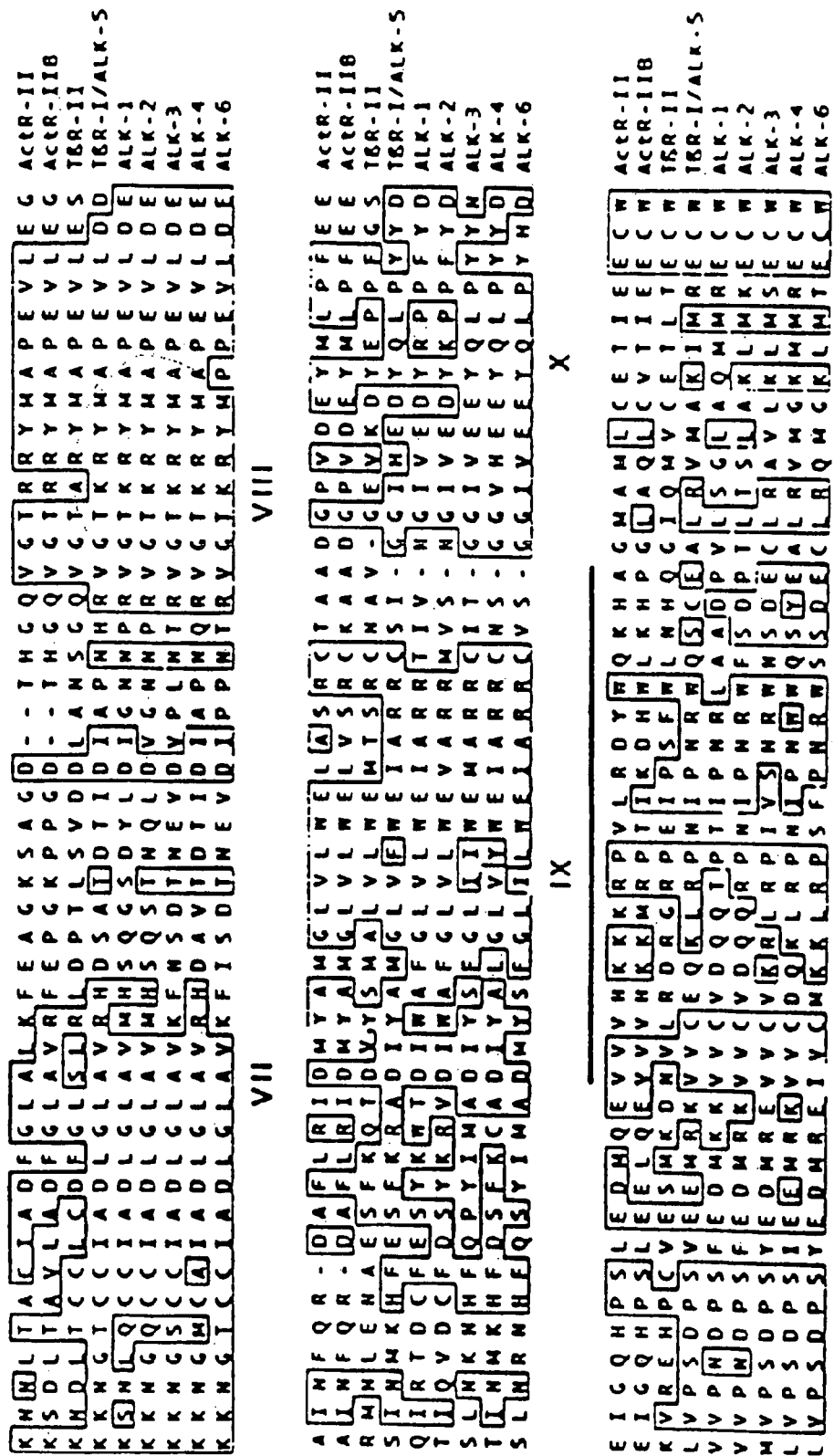
Fig. 3 contd.

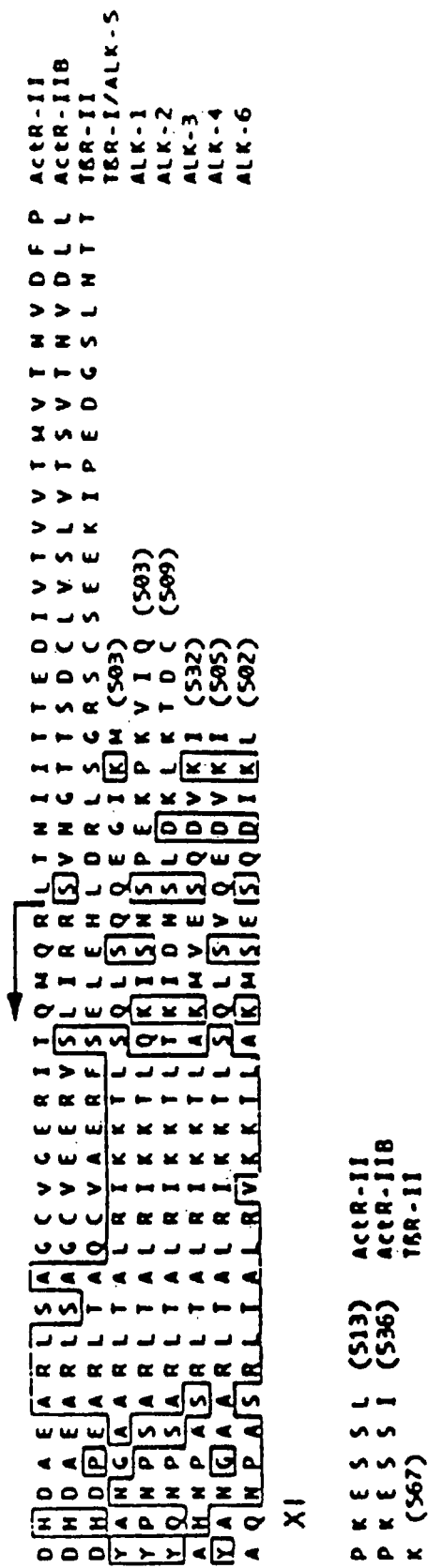
Fig. 3 contd.

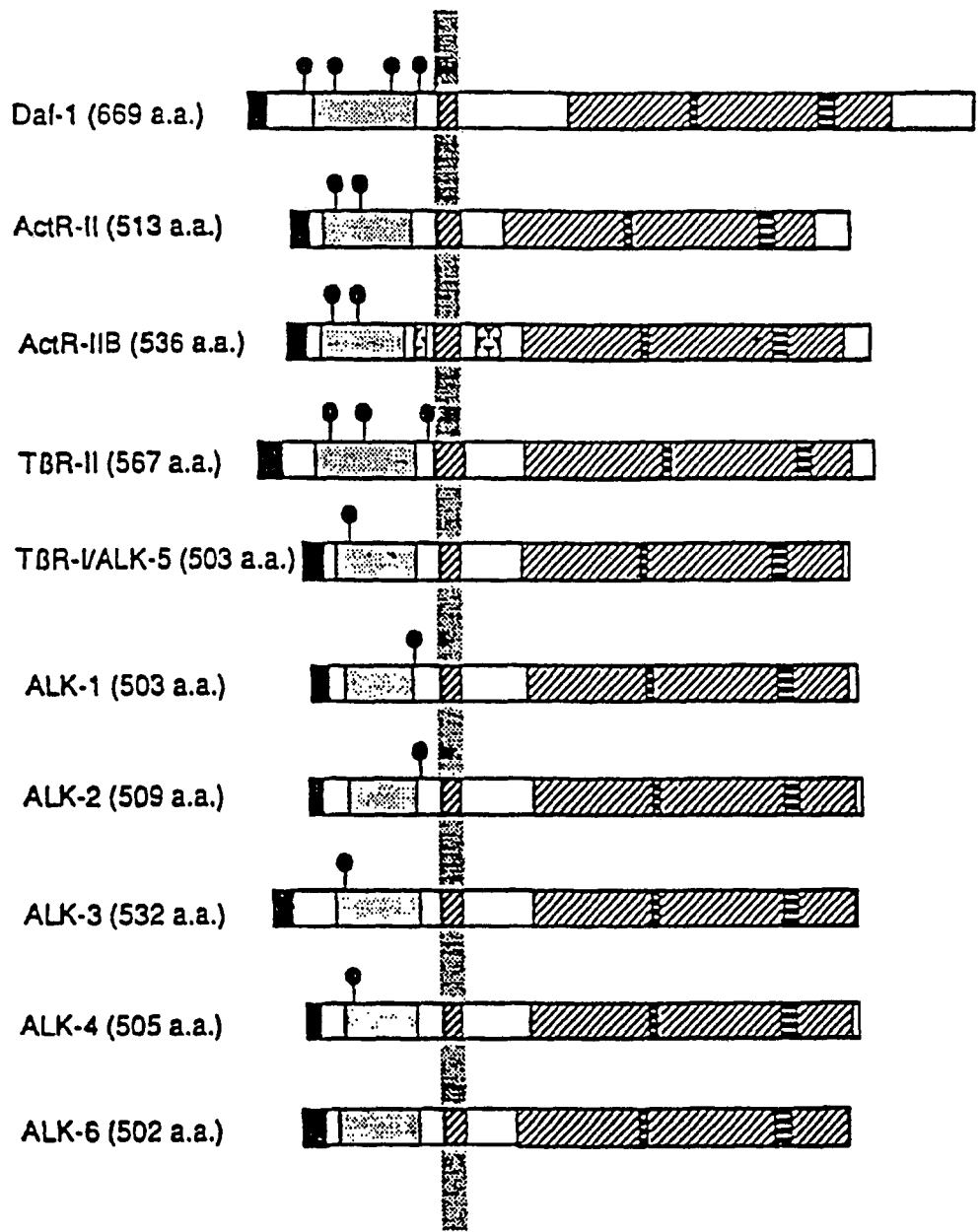
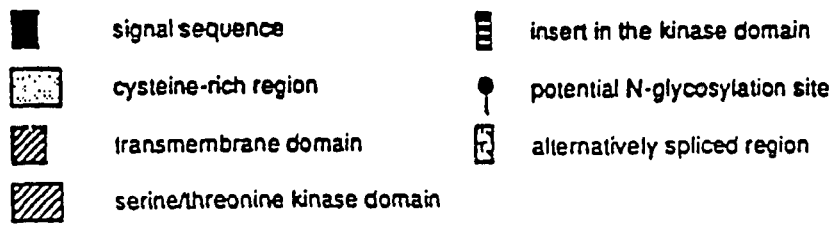
Fig. 4

Fig. 5

|  | ALK-2 | ALK-3 | ALK-4 | ALK-5 | ActR-II | ActR-IIB | TβR-II | daf-1 |  |
|---|---|---|---|---|---|---|---|---|---|
| ALK-1 | 79 | 60 | 61 | 63 | 40 | 40 | 37 | 39 | |
| ALK-2 | | 63 | 64 | 65 | 41 | 39 | 37 | 39 | |
| ALK-3 | | | 63 | 65 | 41 | 38 | 37 | 39 | |
| ALK-4 | | | | 90 | 41 | 40 | 39 | 42 | |
| ALK-5 | | | | | 42 | 40 | 41 | 43 | |
| ActR-II | | | | | | 78 | 48 | 35 | |
| ActR-IIB | | | | | | | 47 | 32 | |
| TβR-II | | | | | | | | 34 | |

Fig. 6

SEQUENCE LISTING

```
(1) GENERAL INFORMATION:

(iii) NUMBER OF SEQUENCES: 48

(2) INFORMATION FOR SEQ ID NO: 1:

(i) SEQUENCE CHARACTERISTICS:
        (A) LENGTH: 1984 base pairs
        (B) TYPE: nucleic acid
        (C) STRANDEDNESS: unknown
        (D) TOPOLOGY: linear (ii) MOLECULE TYPE: cDNA (iii) HYPOTHETICAL: NO (iv) ANTI-SENSE: NO (v) FRAGMENT TYPE: internal (vi) ORIGINAL SOURCE:
         (A) ORGANISM: Homo sapiens (ix) FEATURE:
         (A) NAME/KEY: CDS
         (B) LOCATION: 283..1791

(xi) SEQUENCE DESCRIPTION: SEQ ID NO: 1:

AGGAAACGGT TTATTAGGAG GGAGTGGTGG AGCTGGGCCA GGCAGGAAGA CGCTGGAATA        60

AGAAACATTT TTGCTCCAGC CCCCATCCCA GTCCCGGGAG GCTGCCGCGC CAGCTGCGCC       120

GAGCGAGCCC CTCCCCGGCT CCAGCCCGGT CCGGGGCCGC GCCGGACCCC AGCCCGCCGT       180

CCAGCGCTGG CGGTGCAACT GCGGCCGCGC GGTGGAGGGG AGGTGGCCCC GGTCCGCCGA       240

AGGCTAGCGC CCCGCCACCC GCAGAGCGGG CCCAGAGGGA CC ATG ACC TTG GGC         294
                                              Met Thr Leu Gly
                                                1

TCC CCC AGG AAA GGC CTT CTG ATG CTG CTG ATG GCC TTG GTG ACC CAG        342
Ser Pro Arg Lys Gly Leu Leu Met Leu Leu Met Ala Leu Val Thr Gln
  5              10                  15                  20

GGA GAC CCT GTG AAG CCG TCT CGG GGC CCG CTG GTG ACC TGC ACG TGT        390
Gly Asp Pro Val Lys Pro Ser Arg Gly Pro Leu Val Thr Cys Thr Cys
               25                  30                  35

GAG AGC CCA CAT TGC AAG GGG CCT ACC TGC CGG GGG GCC TGG TGC ACA        438
Glu Ser Pro His Cys Lys Gly Pro Thr Cys Arg Gly Ala Trp Cys Thr
               40                  45                  50

GTA GTG CTG GTG CGG GAG GAG GGG AGG CAC CCC CAG GAA CAT CGG GGC        486
Val Val Leu Val Arg Glu Glu Gly Arg His Pro Gln Glu His Arg Gly
```

-continued

```
                55                    60                    65
TGC GGG AAC TTG CAC AGG GAG CTC TGC AGG GGG CGC CCC ACC GAG TTC        534
Cys Gly Asn Leu His Arg Glu Leu Cys Arg Gly Arg Pro Thr Glu Phe
     70                   75                   80

GTC AAC CAC TAC TGC TGC GAC AGC CAC CTC TGC AAC CAC AAC GTG TCC        582
Val Asn His Tyr Cys Cys Asp Ser His Leu Cys Asn His Asn Val Ser
 85                   90                   95                  100

CTG GTG CTG GAG GCC ACC CAA CCT CCT TCG GAG CAG CCG GGA ACA GAT        630
Leu Val Leu Glu Ala Thr Gln Pro Pro Ser Glu Gln Pro Gly Thr Asp
                         105                  110                  115

GGC CAG CTG GCC CTG ATC CTG GGC CCC GTG CTG GCC TTG CTG GCC CTG        678
Gly Gln Leu Ala Leu Ile Leu Gly Pro Val Leu Ala Leu Leu Ala Leu
                    120                  125                  130

GTG GCC CTG GGT GTC CTG GGC CTG TGG CAT GTC CGA CGG AGG CAG GAG        726
Val Ala Leu Gly Val Leu Gly Leu Trp His Val Arg Arg Arg Gln Glu
               135                  140                  145

AAG CAG CGT GGC CTG CAC AGC GAG CTG GGA GAG TCC AGT CTC ATC CTG        774
Lys Gln Arg Gly Leu His Ser Glu Leu Gly Glu Ser Ser Leu Ile Leu
          150                  155                  160

AAA GCA TCT GAG CAG GGC GAC ACG ATG TTG GGG GAC CTC CTG GAC AGT        822
Lys Ala Ser Glu Gln Gly Asp Thr Met Leu Gly Asp Leu Leu Asp Ser
165                  170                  175                  180

GAC TGC ACC ACA GGG AGT GGC TCA GGG CTC CCC TTC CTG GTG CAG AGG        870
Asp Cys Thr Thr Gly Ser Gly Ser Gly Leu Pro Phe Leu Val Gln Arg
                    185                  190                  195

ACA GTG GCA CGG CAG GTT GCC TTG GTG GAG TGT GTG GGA AAA GGC CGC        918
Thr Val Ala Arg Gln Val Ala Leu Val Glu Cys Val Gly Lys Gly Arg
               200                  205                  210

TAT GGC GAA GTG TGG CGG GGC TTG TGG CAC GGT GAG AGT GTG GCC GTC        966
Tyr Gly Glu Val Trp Arg Gly Leu Trp His Gly Glu Ser Val Ala Val
          215                  220                  225

AAG ATC TTC TCC TCG AGG GAT GAA CAG TCC TGG TTC CGG GAG ACT GAG       1014
Lys Ile Phe Ser Ser Arg Asp Glu Gln Ser Trp Phe Arg Glu Thr Glu
230                  235                  240

ATC TAT AAC ACA GTA TTG CTC AGA CAC GAC AAC ATC CTA GGC TTC ATC       1062
Ile Tyr Asn Thr Val Leu Leu Arg His Asp Asn Ile Leu Gly Phe Ile
245                  250                  255                  260

GCC TCA GAC ATG ACC TCC CGC AAC TCG AGC ACG CAG CTG TGG CTC ATC       1110
Ala Ser Asp Met Thr Ser Arg Asn Ser Ser Thr Gln Leu Trp Leu Ile
                    265                  270                  275

ACG CAC TAC CAC GAG CAC GGC TCC CTC TAC GAC TTT CTG CAG AGA CAG       1158
Thr His Tyr His Glu His Gly Ser Leu Tyr Asp Phe Leu Gln Arg Gln
               280                  285                  290

ACG CTG GAG CCC CAT CTG GCT CTG AGG CTA GCT GTG TCC GCG GCA TGC       1206
Thr Leu Glu Pro His Leu Ala Leu Arg Leu Ala Val Ser Ala Ala Cys
          295                  300                  305

GGC CTG GCG CAC CTG CAC GTG GAG ATC TTC GGT ACA CAG GGC AAA CCA       1254
Gly Leu Ala His Leu His Val Glu Ile Phe Gly Thr Gln Gly Lys Pro
310                  315                  320

GCC ATT GCC CAC CGC GAC TTC AAG AGC CGC AAT GTG CTG GTC AAG AGC       1302
Ala Ile Ala His Arg Asp Phe Lys Ser Arg Asn Val Leu Val Lys Ser
325                  330                  335                  340

AAC CTG CAG TGT TGC ATC GCC GAC CTG GGC CTG GCT GTG ATG CAC TCA       1350
Asn Leu Gln Cys Cys Ile Ala Asp Leu Gly Leu Ala Val Met His Ser
                    345                  350                  355

CAG GGC AGC GAT TAC CTG GAC ATC GGC AAC AAC CCG AGA GTG GGC ACC       1398
Gln Gly Ser Asp Tyr Leu Asp Ile Gly Asn Asn Pro Arg Val Gly Thr
               360                  365                  370

AAG CGG TAC ATG GCA CCC GAG GTG CTG GAC GAG CAG ATC CGC ACG GAC       1446
Lys Arg Tyr Met Ala Pro Glu Val Leu Asp Glu Gln Ile Arg Thr Asp
```

-continued

```
                    375                 380                 385
TGC TTT GAG TCC TAC AAG TGG ACT GAC ATC TGG GCC TTT GGC CTG GTG     1494
Cys Phe Glu Ser Tyr Lys Trp Thr Asp Ile Trp Ala Phe Gly Leu Val
    390                 395                 400

CTG TGG GAG ATT GCC CGC CGG ACC ATC GTG AAT GGC ATC GTG GAG GAC     1542
Leu Trp Glu Ile Ala Arg Arg Thr Ile Val Asn Gly Ile Val Glu Asp
405                 410                 415                 420

TAT AGA CCA CCC TTC TAT GAT GTG GTG CCC AAT GAC CCC AGC TTT GAG     1590
Tyr Arg Pro Pro Phe Tyr Asp Val Val Pro Asn Asp Pro Ser Phe Glu
                425                 430                 435

GAC ATG AAG AAG GTG GTG TGT GTG GAT CAG CAG ACC CCC ACC ATC CCT     1638
Asp Met Lys Lys Val Val Cys Val Asp Gln Gln Thr Pro Thr Ile Pro
            440                 445                 450

AAC CGG CTG GCT GCA GAC CCG GTC CTC TCA GGC CTA GCT CAG ATG ATG     1686
Asn Arg Leu Ala Ala Asp Pro Val Leu Ser Gly Leu Ala Gln Met Met
        455                 460                 465

CGG GAG TGC TGG TAC CCA AAC CCC TCT GCC CGA CTC ACC GCG CTG CGG     1734
Arg Glu Cys Trp Tyr Pro Asn Pro Ser Ala Arg Leu Thr Ala Leu Arg
    470                 475                 480

ATC AAG AAG ACA CTA CAA AAA ATT AGC AAC AGT CCA GAG AAG CCT AAA     1782
Ile Lys Lys Thr Leu Gln Lys Ile Ser Asn Ser Pro Glu Lys Pro Lys
485                 490                 495                 500

GTG ATT CAA TAGCCCAGGA GCACCTGATT CCTTTCTGCC TGCAGGGGGC             1831
Val Ile Gln

TGGGGGGGTG GGGGGCAGTG GATGGTGCCC TATCTGGGTA GAGGTAGTGT GAGTGTGGTG   1891

TGTGCTGGGG ATGGGCAGCT GCGCCTGCCT GCTCGGCCCC CAGCCCACCC AGCCAAAAAT   1951

ACAGCTGGGC TGAAACCTGA AAAAAAAAAA AAA                                1984

(2) INFORMATION FOR SEQ ID NO: 2:

(i) SEQUENCE CHARACTERISTICS:
        (A) LENGTH: 503 amino acids
        (B) TYPE: amino acid
        (D) TOPOLOGY: linear (ii) MOLECULE TYPE: protein (xi) SEQUENCE DESCRIPTION: SEQ ID NO: 2:

Met Thr Leu Gly Ser Pro Arg Lys Gly Leu Leu Met Leu Leu Met Ala
1               5                   10                  15

Leu Val Thr Gln Gly Asp Pro Val Lys Pro Ser Arg Gly Pro Leu Val
                20                  25                  30

Thr Cys Thr Cys Glu Ser Pro His Cys Lys Gly Pro Thr Cys Arg Gly
            35                  40                  45

Ala Trp Cys Thr Val Val Leu Val Arg Glu Glu Gly Arg His Pro Gln
    50                  55                  60

Glu His Arg Gly Cys Gly Asn Leu His Arg Glu Leu Cys Arg Gly Arg
65                  70                  75                  80

Pro Thr Glu Phe Val Asn His Tyr Cys Cys Asp Ser His Leu Cys Asn
                85                  90                  95

His Asn Val Ser Leu Val Leu Glu Ala Thr Gln Pro Pro Ser Glu Gln
            100                 105                 110

Pro Gly Thr Asp Gly Gln Leu Ala Leu Ile Leu Gly Pro Val Leu Ala
    115                 120                 125

Leu Leu Ala Leu Val Ala Leu Gly Val Leu Gly Leu Trp His Val Arg
130                 135                 140

Arg Arg Gln Glu Lys Gln Arg Gly Leu His Ser Glu Leu Gly Glu Ser
145                 150                 155                 160
```

Ser Leu Ile Leu Lys Ala Ser Glu Gln Gly Asp Thr Met Leu Gly Asp
            165                 170                 175

Leu Leu Asp Ser Asp Cys Thr Thr Gly Ser Gly Ser Gly Leu Pro Phe
        180                 185                 190

Leu Val Gln Arg Thr Val Ala Arg Gln Val Ala Leu Val Glu Cys Val
    195                 200                 205

Gly Lys Gly Arg Tyr Gly Glu Val Trp Arg Gly Leu Trp His Gly Glu
210                 215                 220

Ser Val Ala Val Lys Ile Phe Ser Ser Arg Asp Glu Gln Ser Trp Phe
225                 230                 235                 240

Arg Glu Thr Glu Ile Tyr Asn Thr Val Leu Leu Arg His Asp Asn Ile
            245                 250                 255

Leu Gly Phe Ile Ala Ser Asp Met Thr Ser Arg Asn Ser Ser Thr Gln
        260                 265                 270

Leu Trp Leu Ile Thr His Tyr His Glu His Gly Ser Leu Tyr Asp Phe
    275                 280                 285

Leu Gln Arg Gln Thr Leu Glu Pro His Leu Ala Leu Arg Leu Ala Val
290                 295                 300

Ser Ala Ala Cys Gly Leu Ala His Leu His Val Glu Ile Phe Gly Thr
305                 310                 315                 320

Gln Gly Lys Pro Ala Ile Ala His Arg Asp Phe Lys Ser Arg Asn Val
            325                 330                 335

Leu Val Lys Ser Asn Leu Gln Cys Cys Ile Ala Asp Leu Gly Leu Ala
        340                 345                 350

Val Met His Ser Gln Gly Ser Asp Tyr Leu Asp Ile Gly Asn Asn Pro
    355                 360                 365

Arg Val Gly Thr Lys Arg Tyr Met Ala Pro Glu Val Leu Asp Glu Gln
370                 375                 380

Ile Arg Thr Asp Cys Phe Glu Ser Tyr Lys Trp Thr Asp Ile Trp Ala
385                 390                 395                 400

Phe Gly Leu Val Leu Trp Glu Ile Ala Arg Arg Thr Ile Val Asn Gly
            405                 410                 415

Ile Val Glu Asp Tyr Arg Pro Pro Phe Tyr Asp Val Val Pro Asn Asp
        420                 425                 430

Pro Ser Phe Glu Asp Met Lys Lys Val Val Cys Val Asp Gln Gln Thr
    435                 440                 445

Pro Thr Ile Pro Asn Arg Leu Ala Ala Asp Pro Val Leu Ser Gly Leu
450                 455                 460

Ala Gln Met Met Arg Glu Cys Trp Tyr Pro Asn Pro Ser Ala Arg Leu
465                 470                 475                 480

Thr Ala Leu Arg Ile Lys Lys Thr Leu Gln Lys Ile Ser Asn Ser Pro
            485                 490                 495

Glu Lys Pro Lys Val Ile Gln
            500

(2) INFORMATION FOR SEQ ID NO: 3:

(i) SEQUENCE CHARACTERISTICS:
        (A) LENGTH: 2724 base pairs
        (B) TYPE: nucleic acid
        (C) STRANDEDNESS: unknown
        (D) TOPOLOGY: linear (ii) MOLECULE TYPE: cDNA (iii) HYPOTHETICAL: NO (iv) ANTI-SENSE: NO (v) FRAGMENT TYPE: internal (vi) ORIGINAL SOURCE:
    (A) ORGANISM: Homo sapiens (ix) FEATURE:
    (A) NAME/KEY: CDS
    (B) LOCATION: 104..1630

(xi) SEQUENCE DESCRIPTION: SEQ ID NO: 3:

```
CTCCGAGTAC CCCAGTGACC AGAGTGAGAG AAGCTCTGAA CGAGGGCACG CGGCTTGAAG          60

GACTGTGGGC AGATGTGACC AAGAGCCTGC ATTAAGTTGT ACA ATG GTA GAT GGA          115
                                             Met Val Asp Gly
                                              1

GTG ATG ATT CTT CCT GTG CTT ATC ATG ATT GCT CTC CCC TCC CCT AGT          163
Val Met Ile Leu Pro Val Leu Ile Met Ile Ala Leu Pro Ser Pro Ser
 5              10                  15                  20

ATG GAA GAT GAG AAG CCC AAG GTC AAC CCC AAA CTC TAC ATG TGT GTG          211
Met Glu Asp Glu Lys Pro Lys Val Asn Pro Lys Leu Tyr Met Cys Val
                 25                  30                  35

TGT GAA GGT CTC TCC TGC GGT AAT GAG GAC CAC TGT GAA GGC CAG CAG          259
Cys Glu Gly Leu Ser Cys Gly Asn Glu Asp His Cys Glu Gly Gln Gln
             40                  45                  50

TGC TTT TCC TCA CTG AGC ATC AAC GAT GGC TTC CAC GTC TAC CAG AAA          307
Cys Phe Ser Ser Leu Ser Ile Asn Asp Gly Phe His Val Tyr Gln Lys
         55                  60                  65

GGC TGC TTC CAG GTT TAT GAG CAG GGA AAG ATG ACC TGT AAG ACC CCG          355
Gly Cys Phe Gln Val Tyr Glu Gln Gly Lys Met Thr Cys Lys Thr Pro
     70                  75                  80

CCG TCC CCT GGC CAA GCT GTG GAG TGC TGC CAA GGG GAC TGG TGT AAC          403
Pro Ser Pro Gly Gln Ala Val Glu Cys Cys Gln Gly Asp Trp Cys Asn
 85                  90                  95                 100

AGG AAC ATC ACG GCC CAG CTG CCC ACT AAA GGA AAA TCC TTC CCT GGA          451
Arg Asn Ile Thr Ala Gln Leu Pro Thr Lys Gly Lys Ser Phe Pro Gly
                105                 110                 115

ACA CAG AAT TTC CAC TTG GAG GTT GGC CTC ATT ATT CTC TCT GTA GTG          499
Thr Gln Asn Phe His Leu Glu Val Gly Leu Ile Ile Leu Ser Val Val
            120                 125                 130

TTC GCA GTA TGT CTT TTA GCC TGC CTG CTG GGA GTT GCT CTC CGA AAA          547
Phe Ala Val Cys Leu Leu Ala Cys Leu Leu Gly Val Ala Leu Arg Lys
        135                 140                 145

TTT AAA AGG CGC AAC CAA GAA CGC CTC AAT CCC CGA GAC GTG GAG TAT          595
Phe Lys Arg Arg Asn Gln Glu Arg Leu Asn Pro Arg Asp Val Glu Tyr
    150                 155                 160

GGC ACT ATC GAA GGG CTC ATC ACC ACC AAT GTT GGA GAC AGC ACT TTA          643
Gly Thr Ile Glu Gly Leu Ile Thr Thr Asn Val Gly Asp Ser Thr Leu
165                 170                 175                 180

GCA GAT TTA TTG GAT CAT TCG TGT ACA TCA GGA AGT GGC TCT GGT CTT          691
Ala Asp Leu Leu Asp His Ser Cys Thr Ser Gly Ser Gly Ser Gly Leu
                185                 190                 195

CCT TTT CTG GTA CAA AGA ACA GTG GCT CGC CAG ATT ACA CTG TTG GAG          739
Pro Phe Leu Val Gln Arg Thr Val Ala Arg Gln Ile Thr Leu Leu Glu
            200                 205                 210

TGT GTC GGG AAA GGC AGG TAT GGT GAG GTG TGG AGG GGC AGC TGG CAA          787
Cys Val Gly Lys Gly Arg Tyr Gly Glu Val Trp Arg Gly Ser Trp Gln
        215                 220                 225

GGG GAA AAT GTT GCC GTG AAG ATC TTC TCC TCC CGT GAT GAG AAG TCA          835
Gly Glu Asn Val Ala Val Lys Ile Phe Ser Ser Arg Asp Glu Lys Ser
    230                 235                 240

TGG TTC AGG GAA ACG GAA TTG TAC AAC ACT GTG ATG CTG AGG CAT GAA          883
```

```
Trp Phe Arg Glu Thr Glu Leu Tyr Asn Thr Val Met Leu Arg His Glu
245                 250                 255                 260

AAT ATC TTA GGT TTC ATT GCT TCA GAC ATG ACA TCA AGA CAC TCC AGT      931
Asn Ile Leu Gly Phe Ile Ala Ser Asp Met Thr Ser Arg His Ser Ser
                265                 270                 275

ACC CAG CTG TGG TTA ATT ACA CAT TAT CAT GAA ATG GGA TCG TTG TAC      979
Thr Gln Leu Trp Leu Ile Thr His Tyr His Glu Met Gly Ser Leu Tyr
                280                 285                 290

GAC TAT CTT CAG CTT ACT ACT CTG GAT ACA GTT AGC TGC CTT CGA ATA     1027
Asp Tyr Leu Gln Leu Thr Thr Leu Asp Thr Val Ser Cys Leu Arg Ile
            295                 300                 305

GTG CTG TCC ATA GCT AGT GGT CTT GCA CAT TTG CAC ATA GAG ATA TTT     1075
Val Leu Ser Ile Ala Ser Gly Leu Ala His Leu His Ile Glu Ile Phe
        310                 315                 320

GGG ACC CAA GGG AAA CCA GCC ATT GCC CAT CGA GAT TTA AAG AGC AAA     1123
Gly Thr Gln Gly Lys Pro Ala Ile Ala His Arg Asp Leu Lys Ser Lys
325                 330                 335                 340

AAT ATT CTG GTT AAG AAG AAT GGA CAG TGT TGC ATA GCA GAT TTG GGC     1171
Asn Ile Leu Val Lys Lys Asn Gly Gln Cys Cys Ile Ala Asp Leu Gly
                345                 350                 355

CTG GCA GTC ATG CAT TCC CAG AGC ACC AAT CAG CTT GAT GTG GGG AAC     1219
Leu Ala Val Met His Ser Gln Ser Thr Asn Gln Leu Asp Val Gly Asn
                360                 365                 370

AAT CCC CGT GTG GGC ACC AAG CGC TAC ATG GCC CCC GAA GTT CTA GAT     1267
Asn Pro Arg Val Gly Thr Lys Arg Tyr Met Ala Pro Glu Val Leu Asp
            375                 380                 385

GAA ACC ATC CAG GTG GAT TGT TTC GAT TCT TAT AAA AGG GTC GAT ATT     1315
Glu Thr Ile Gln Val Asp Cys Phe Asp Ser Tyr Lys Arg Val Asp Ile
        390                 395                 400

TGG GCC TTT GGA CTT GTT TTG TGG GAA GTG GCC AGG CGG ATG GTG AGC     1363
Trp Ala Phe Gly Leu Val Leu Trp Glu Val Ala Arg Arg Met Val Ser
405                 410                 415                 420

AAT GGT ATA GTG GAG GAT TAC AAG CCA CCG TTC TAC GAT GTG GTT CCC     1411
Asn Gly Ile Val Glu Asp Tyr Lys Pro Pro Phe Tyr Asp Val Val Pro
                425                 430                 435

AAT GAC CCA AGT TTT GAA GAT ATG AGG AAG GTA GTC TGT GTG GAT CAA     1459
Asn Asp Pro Ser Phe Glu Asp Met Arg Lys Val Val Cys Val Asp Gln
                440                 445                 450

CAA AGG CCA AAC ATA CCC AAC AGA TGG TTC TCA GAC CCG ACA TTA ACC     1507
Gln Arg Pro Asn Ile Pro Asn Arg Trp Phe Ser Asp Pro Thr Leu Thr
            455                 460                 465

TCT CTG GCC AAG CTA ATG AAA GAA TGC TGG TAT CAA AAT CCA TCC GCA     1555
Ser Leu Ala Lys Leu Met Lys Glu Cys Trp Tyr Gln Asn Pro Ser Ala
        470                 475                 480

AGA CTC ACA GCA CTG CGT ATC AAA AAG ACT TTG ACC AAA ATT GAT AAT     1603
Arg Leu Thr Ala Leu Arg Ile Lys Lys Thr Leu Thr Lys Ile Asp Asn
485                 490                 495                 500

TCC CTC GAC AAA TTG AAA ACT GAC TGT TGACATTTTC ATAGTGTCAA           1650
Ser Leu Asp Lys Leu Lys Thr Asp Cys
                505

GAAGGAAGAT TGACGTTGT TGTCATTGTC CAGCTGGGAC CTAATGCTGG CCTGACTGGT    1710

TGTCAGAATG GAATCCATCT GTCTCCCTCC CCAAATGGCT GCTTTGACAA GGCAGACGTC   1770

GTACCCAGCC ATGTGTTGGG GAGACATCAA AACCACCCTA ACCTCGCTCG ATGACTGTGA   1830

ACTGGGCATT TCACGAACTG TTCACACTGC AGAGACTAAT GTTGGACAGA CACTGTTGCA   1890

AAGGTAGGGA CTGGAGGAAC ACAGAGAAAT CCTAAAAGAG ATCTGGGCAT TAAGTCAGTG   1950

GCTTTGCATA GCTTTCACAA GTCTCCTAGA CACTCCCCAC GGGAAACTCA AGGAGGTGGT   2010

GAATTTTTAA TCAGCAATAT TGCCTGTGCT TCTCTTCTTT ATTGCACTAG GAATTCTTTG   2070
```

-continued

```
CATTCCTTAC TTGCACTGTT ACTCTTAATT TTAAAGACCC AACTTGCCAA AATGTTGGCT    2130

GCGTACTCCA CTGGTCTGTC TTTGGATAAT AGGAATTCAA TTTGGCAAAA CAAAATGTAA    2190

TGTCAGACTT TGCTGCATTT TACACATGTG CTGATGTTTA CAATGATGCC GAACATTAGG    2250

AATTGTTTAT ACACAACTTT GCAAATTATT TATTACTTGT GCACTTAGTA GTTTTTACAA    2310

AACTGCTTTG TGCATATGTT AAAGCTTATT TTTATGTGGT CTTATGATTT TATTACAGAA    2370

ATGTTTTTAA CACTATACTC TAAAATGGAC ATTTTCTTTT ATTATCAGTT AAAATCACAT    2430

TTTAAGTGCT TCACATTTGT ATGTGTGTAG ACTGTAACTT TTTTTCAGTT CATATGCAGA    2490

ACGTATTTAG CCATTACCCA CGTGACACCA CCGAATATAT TATCGATTTA GAAGCAAAGA    2550

TTTCAGTAGA ATTTTAGTCC TGAACGCTAC GGGGAAAATG CATTTTCTTC AGAATTATCC    2610

ATTACGTGCA TTTAAACTCT GCCAGAAAAA AATAACTATT TTGTTTTAAT CTACTTTTTG    2670

TATTTAGTAG TTATTTGTAT AAATTAAATA AACTGTTTTC AAGTCAAAAA AAAA           2724
```

(2) INFORMATION FOR SEQ ID NO: 4:

(i) SEQUENCE CHARACTERISTICS:
        (A) LENGTH: 509 amino acids
        (B) TYPE: amino acid
        (D) TOPOLOGY: linear (ii) MOLECULE TYPE: protein (xi) SEQUENCE DESCRIPTION: SEQ ID NO: 4:

```
Met Val Asp Gly Val Met Ile Leu Pro Val Leu Ile Met Ile Ala Leu
 1               5                  10                  15

Pro Ser Pro Ser Met Glu Asp Glu Lys Pro Lys Val Asn Pro Lys Leu
            20                  25                  30

Tyr Met Cys Val Cys Glu Gly Leu Ser Cys Gly Asn Glu Asp His Cys
        35                  40                  45

Glu Gly Gln Gln Cys Phe Ser Ser Leu Ser Ile Asn Asp Gly Phe His
    50                  55                  60

Val Tyr Gln Lys Gly Cys Phe Gln Val Tyr Glu Gln Gly Lys Met Thr
65                  70                  75                  80

Cys Lys Thr Pro Pro Ser Pro Gly Gln Ala Val Glu Cys Cys Gln Gly
                85                  90                  95

Asp Trp Cys Asn Arg Asn Ile Thr Ala Gln Leu Pro Thr Lys Gly Lys
            100                 105                 110

Ser Phe Pro Gly Thr Gln Asn Phe His Leu Glu Val Gly Leu Ile Ile
        115                 120                 125

Leu Ser Val Val Phe Ala Val Cys Leu Leu Ala Cys Leu Leu Gly Val
    130                 135                 140

Ala Leu Arg Lys Phe Lys Arg Arg Asn Gln Glu Arg Leu Asn Pro Arg
145                 150                 155                 160

Asp Val Glu Tyr Gly Thr Ile Glu Gly Leu Ile Thr Thr Asn Val Gly
                165                 170                 175

Asp Ser Thr Leu Ala Asp Leu Leu Asp His Ser Cys Thr Ser Gly Ser
            180                 185                 190

Gly Ser Gly Leu Pro Phe Leu Val Gln Arg Thr Val Ala Arg Gln Ile
        195                 200                 205

Thr Leu Leu Glu Cys Val Gly Lys Gly Arg Tyr Gly Glu Val Trp Arg
    210                 215                 220

Gly Ser Trp Gln Gly Glu Asn Val Ala Val Lys Ile Phe Ser Ser Arg
225                 230                 235                 240
```

-continued

```
Asp Glu Lys Ser Trp Phe Arg Glu Thr Glu Leu Tyr Asn Thr Val Met
            245                 250                 255

Leu Arg His Glu Asn Ile Leu Gly Phe Ile Ala Ser Asp Met Thr Ser
        260                 265                 270

Arg His Ser Ser Thr Gln Leu Trp Leu Ile Thr His Tyr His Glu Met
            275                 280                 285

Gly Ser Leu Tyr Asp Tyr Leu Gln Leu Thr Thr Leu Asp Thr Val Ser
        290                 295                 300

Cys Leu Arg Ile Val Leu Ser Ile Ala Ser Gly Leu Ala His Leu His
305                 310                 315                 320

Ile Glu Ile Phe Gly Thr Gln Gly Lys Pro Ala Ile Ala His Arg Asp
            325                 330                 335

Leu Lys Ser Lys Asn Ile Leu Val Lys Lys Asn Gly Gln Cys Cys Ile
            340                 345                 350

Ala Asp Leu Gly Leu Ala Val Met His Ser Gln Ser Thr Asn Gln Leu
        355                 360                 365

Asp Val Gly Asn Asn Pro Arg Val Gly Thr Lys Arg Tyr Met Ala Pro
        370                 375                 380

Glu Val Leu Asp Glu Thr Ile Gln Val Asp Cys Phe Asp Ser Tyr Lys
385                 390                 395                 400

Arg Val Asp Ile Trp Ala Phe Gly Leu Val Leu Trp Glu Val Ala Arg
                405                 410                 415

Arg Met Val Ser Asn Gly Ile Val Glu Asp Tyr Lys Pro Pro Phe Tyr
            420                 425                 430

Asp Val Val Pro Asn Asp Pro Ser Phe Glu Asp Met Arg Lys Val Val
        435                 440                 445

Cys Val Asp Gln Gln Arg Pro Asn Ile Pro Asn Arg Trp Phe Ser Asp
450                 455                 460

Pro Thr Leu Thr Ser Leu Ala Lys Leu Met Lys Glu Cys Trp Tyr Gln
465                 470                 475                 480

Asn Pro Ser Ala Arg Leu Thr Ala Leu Arg Ile Lys Lys Thr Leu Thr
                485                 490                 495

Lys Ile Asp Asn Ser Leu Asp Lys Leu Lys Thr Asp Cys
                500                 505
```

(2) INFORMATION FOR SEQ ID NO: 5:

(i) SEQUENCE CHARACTERISTICS:
        (A) LENGTH: 2932 base pairs
        (B) TYPE: nucleic acid
        (C) STRANDEDNESS: unknown
        (D) TOPOLOGY: linear (ii) MOLECULE TYPE: cDNA (iii) HYPOTHETICAL: NO (iv) ANTI-SENSE: NO (v) FRAGMENT TYPE: internal (vi) ORIGINAL SOURCE:
        (A) ORGANISM: Homo sapiens (ix) FEATURE:
        (A) NAME/KEY: CDS
        (B) LOCATION: 310..1905

(xi) SEQUENCE DESCRIPTION: SEQ ID NO: 5:

```
GCTCCGCGCC GAGGGCTGGA GGATGCGTTC CCTGGGGTCC GGACTTATGA AAATATGCAT      60

CAGTTTAATA CTGTCTTGGA ATTCATGAGA TGGAAGCATA GGTCAAAGCT GTTTGGAGAA     120
```

```
AATCAGAAGT ACAGTTTTAT CTAGCCACAT CTTGGAGGAG TCGTAAGAAA GCAGTGGGAG      180

TTGAAGTCAT TGTCAAGTGC TTGCGATCTT TTACAAGAAA ATCTCACTGA ATGATAGTCA      240

TTTAAATTGG TGAAGTAGCA AGACCAATTA TTAAAGGTGA CAGTACACAG GAAACATTAC      300

AATTGAACA ATG ACT CAG CTA TAC ATT TAC ATC AGA TTA TTG GGA GCC          348
          Met Thr Gln Leu Tyr Ile Tyr Ile Arg Leu Leu Gly Ala
            1               5                  10

TAT TTG TTC ATC ATT TCT CGT GTT CAA GGA CAG AAT CTG GAT AGT ATG        396
Tyr Leu Phe Ile Ile Ser Arg Val Gln Gly Gln Asn Leu Asp Ser Met
 15                  20                  25

CTT CAT GGC ACT GGG ATG AAA TCA GAC TCC GAC CAG AAA AAG TCA GAA        444
Leu His Gly Thr Gly Met Lys Ser Asp Ser Asp Gln Lys Lys Ser Glu
 30                  35                  40                  45

AAT GGA GTA ACC TTA GCA CCA GAG GAT ACC TTG CCT TTT TTA AAG TGC        492
Asn Gly Val Thr Leu Ala Pro Glu Asp Thr Leu Pro Phe Leu Lys Cys
                 50                  55                  60

TAT TGC TCA GGG CAC TGT CCA GAT GAT GCT ATT AAT AAC ACA TGC ATA        540
Tyr Cys Ser Gly His Cys Pro Asp Asp Ala Ile Asn Asn Thr Cys Ile
                 65                  70                  75

ACT AAT GGA CAT TGC TTT GCC ATC ATA GAA GAA GAT GAC CAG GGA GAA        588
Thr Asn Gly His Cys Phe Ala Ile Ile Glu Glu Asp Asp Gln Gly Glu
             80                  85                  90

ACC ACA TTA GCT TCA GGG TGT ATG AAA TAT GAA GGA TCT GAT TTT CAG        636
Thr Thr Leu Ala Ser Gly Cys Met Lys Tyr Glu Gly Ser Asp Phe Gln
 95                 100                 105

TGC AAA GAT TCT CCA AAA GCC CAG CTA CGC CGG ACA ATA GAA TGT TGT        684
Cys Lys Asp Ser Pro Lys Ala Gln Leu Arg Arg Thr Ile Glu Cys Cys
110                 115                 120                 125

CGG ACC AAT TTA TGT AAC CAG TAT TTG CAA CCC ACA CTG CCC CCT GTT        732
Arg Thr Asn Leu Cys Asn Gln Tyr Leu Gln Pro Thr Leu Pro Pro Val
                130                 135                 140

GTC ATA GGT CCG TTT TTT GAT GGC AGC ATT CGA TGG CTG GTT TTG CTC        780
Val Ile Gly Pro Phe Phe Asp Gly Ser Ile Arg Trp Leu Val Leu Leu
                145                 150                 155

ATT TCT ATG GCT GTC TGC ATA ATT GCT ATG ATC ATC TTC TCC AGC TGC        828
Ile Ser Met Ala Val Cys Ile Ile Ala Met Ile Ile Phe Ser Ser Cys
            160                 165                 170

TTT TGT TAC AAA CAT TAT TGC AAG AGC ATC TCA AGC AGA CGT CGT TAC        876
Phe Cys Tyr Lys His Tyr Cys Lys Ser Ile Ser Ser Arg Arg Arg Tyr
175                 180                 185

AAT CGT GAT TTG GAA CAG GAT GAA GCA TTT ATT CCA GTT GGA GAA TCA        924
Asn Arg Asp Leu Glu Gln Asp Glu Ala Phe Ile Pro Val Gly Glu Ser
190                 195                 200                 205

CTA AAA GAC CTT ATT GAC CAG TCA CAA AGT TCT GGT AGT GGG TCT GGA        972
Leu Lys Asp Leu Ile Asp Gln Ser Gln Ser Ser Gly Ser Gly Ser Gly
                210                 215                 220

CTA CCT TTA TTG GTT CAG CGA ACT ATT GCC AAA CAG ATT CAG ATG GTC       1020
Leu Pro Leu Leu Val Gln Arg Thr Ile Ala Lys Gln Ile Gln Met Val
            225                 230                 235

CGG CAA GTT GGT AAA GGC CGA TAT GGA GAA GTA TGG ATG GGC AAA TGG       1068
Arg Gln Val Gly Lys Gly Arg Tyr Gly Glu Val Trp Met Gly Lys Trp
            240                 245                 250

CGT GGC GAA AAA GTG GCG GTG AAA GTA TTC TTT ACC ACT GAA GAA GCC       1116
Arg Gly Glu Lys Val Ala Val Lys Val Phe Phe Thr Thr Glu Glu Ala
255                 260                 265

AGC TGG TTT CGA GAA ACA GAA ATC TAC CAA ACT GTG CTA ATG CGC CAT       1164
Ser Trp Phe Arg Glu Thr Glu Ile Tyr Gln Thr Val Leu Met Arg His
270                 275                 280                 285

GAA AAC ATA CTT GGT TTC ATA GCG GCA GAC ATT AAA GGT ACA GGT TCC       1212
Glu Asn Ile Leu Gly Phe Ile Ala Ala Asp Ile Lys Gly Thr Gly Ser
```

-continued

```
Glu Asn Ile Leu Gly Phe Ile Ala Ala Asp Ile Lys Gly Thr Gly Ser
                290                 295                 300

TGG ACT CAG CTC TAT TTG ATT ACT GAT TAC CAT GAA AAT GGA TCT CTC         1260
Trp Thr Gln Leu Tyr Leu Ile Thr Asp Tyr His Glu Asn Gly Ser Leu
                305                 310                 315

TAT GAC TTC CTG AAA TGT GCT ACA CTG GAC ACC AGA GCC CTG CTT AAA         1308
Tyr Asp Phe Leu Lys Cys Ala Thr Leu Asp Thr Arg Ala Leu Leu Lys
            320                 325                 330

TTG GCT TAT TCA GCT GCC TGT GGT CTG TGC CAC CTG CAC ACA GAA ATT         1356
Leu Ala Tyr Ser Ala Ala Cys Gly Leu Cys His Leu His Thr Glu Ile
            335                 340                 345

TAT GGC ACC CAA GGA AAG CCC GCA ATT GCT CAT CGA GAC CTA AAG AGC         1404
Tyr Gly Thr Gln Gly Lys Pro Ala Ile Ala His Arg Asp Leu Lys Ser
350                 355                 360                 365

AAA AAC ATC CTC ATC AAG AAA AAT GGG AGT TGC TGC ATT GCT GAC CTG         1452
Lys Asn Ile Leu Ile Lys Lys Asn Gly Ser Cys Cys Ile Ala Asp Leu
                370                 375                 380

GGC CTT GCT GTT AAA TTC AAC AGT GAC ACA AAT GAA GTT GAT GTG CCC         1500
Gly Leu Ala Val Lys Phe Asn Ser Asp Thr Asn Glu Val Asp Val Pro
            385                 390                 395

TTG AAT ACC AGG GTG GGC ACC AAA CGC TAC ATG GCT CCC GAA GTG CTG         1548
Leu Asn Thr Arg Val Gly Thr Lys Arg Tyr Met Ala Pro Glu Val Leu
            400                 405                 410

GAC GAA AGC CTG AAC AAA AAC CAC TTC CAG CCC TAC ATC ATG GCT GAC         1596
Asp Glu Ser Leu Asn Lys Asn His Phe Gln Pro Tyr Ile Met Ala Asp
        415                 420                 425

ATC TAC AGC TTC GGC CTA ATC ATT TGG GAG ATG GCT CGT CGT TGT ATC         1644
Ile Tyr Ser Phe Gly Leu Ile Ile Trp Glu Met Ala Arg Arg Cys Ile
430                 435                 440                 445

ACA GGA GGG ATC GTG GAA GAA TAC CAA TTG CCA TAT TAC AAC ATG GTA         1692
Thr Gly Gly Ile Val Glu Glu Tyr Gln Leu Pro Tyr Tyr Asn Met Val
                450                 455                 460

CCG AGT GAT CCG TCA TAC GAA GAT ATG CGT GAG GTT GTG TGT GTC AAA         1740
Pro Ser Asp Pro Ser Tyr Glu Asp Met Arg Glu Val Val Cys Val Lys
            465                 470                 475

CGT TTG CGG CCA ATT GTG TCT AAT CGG TGG AAC AGT GAT GAA TGT CTA         1788
Arg Leu Arg Pro Ile Val Ser Asn Arg Trp Asn Ser Asp Glu Cys Leu
            480                 485                 490

CGA GCA GTT TTG AAG CTA ATG TCA GAA TGC TGG GCC CAC AAT CCA GCC         1836
Arg Ala Val Leu Lys Leu Met Ser Glu Cys Trp Ala His Asn Pro Ala
        495                 500                 505

TCC AGA CTC ACA GCA TTG AGA ATT AAG AAG ACG CTT GCC AAG ATG GTT         1884
Ser Arg Leu Thr Ala Leu Arg Ile Lys Lys Thr Leu Ala Lys Met Val
510                 515                 520                 525

GAA TCC CAA GAT GTA AAA ATC TGATGGTTAA ACCATCGGAG GAGAAACTCT            1935
Glu Ser Gln Asp Val Lys Ile
                530

AGACTGCAAG AACTGTTTTT ACCCATGGCA TGGGTGGAAT TAGAGTGGAA TAAGGATGTT       1995

AACTTGGTTC TCAGACTCTT TCTTCACTAC GTGTTCACAG GCTGCTAATA TTAAACCTTT       2055

CAGTACTCTT ATTAGGATAC AAGCTGGGAA CTTCTAAACA CTTCATTCTT TATATATGGA       2115

CAGCTTTATT TTAAATGTGG TTTTTGATGC CTTTTTTTAA GTGGGTTTTT ATGAACTGCA       2175

TCAAGACTTC AATCCTGATT AGTGTCTCCA GTCAAGCTCT GGGTACTGAA TTGCCTGTTC       2235

ATAAAACGGT GCTTTCTGTG AAAGCCTTAA GAAGATAAAT GAGCGCAGCA GAGATGGAGA       2295

AATAGACTTT GCCTTTTACC TGAGACATTC AGTTCGTTTG TATTCTACCT TTGTAAAACA       2355

GCCTATAGAT GATGATGTGT TTGGGATACT GCTTATTTTA TGATAGTTTG TCCTGTGTCC       2415

TTAGTGATGT GTGTGTGTCT CCATGCACAT GCACGCCGGG ATTCCTCTGC TGCCATTTGA       2475
```

```
ATTAGAAGAA AATAATTTAT ATGCATGCAC AGGAAGATAT TGGTGGCCGG TGGTTTTGTG   2535

CTTTAAAAAT GCAATATCTG ACCAAGATTC GCCAATCTCA TACAAGCCAT TTACTTTGCA   2595

AGTGAGATAG CTTCCCCACC AGCTTTATTT TTTAACATGA AAGCTGATGC CAAGGCCAAA   2655

AGAAGTTTAA AGCATCTGTA AATTTGGACT GTTTTCCTTC AACCACCATT TTTTTTGTGG   2715

TTATTATTTT TGTCACGGAA AGCATCCTCT CCAAAGTTGG AGCTTCTATT GCCATGAACC   2775

ATGCTTACAA AGAAAGCACT TCTTATTGAA GTGAATTCCT GCATTTGATA GCAATGTAAG   2835

TGCCTATAAC CATGTTCTAT ATTCTTTATT CTCAGTAACT TTTAAAAGGG AAGTTATTTA   2895

TATTTTGTGT ATAATGTGCT TTATTTGCAA ATCACCC                            2932
```

(2) INFORMATION FOR SEQ ID NO: 6:

(i) SEQUENCE CHARACTERISTICS:
        (A) LENGTH: 532 amino acids
        (B) TYPE: amino acid
        (D) TOPOLOGY: linear (ii) MOLECULE TYPE: protein (xi) SEQUENCE DESCRIPTION: SEQ ID NO: 6:

```
Met Thr Gln Leu Tyr Ile Tyr Ile Arg Leu Leu Gly Ala Tyr Leu Phe
 1               5                  10                  15

Ile Ile Ser Arg Val Gln Gly Gln Asn Leu Asp Ser Met Leu His Gly
            20                  25                  30

Thr Gly Met Lys Ser Asp Ser Asp Gln Lys Lys Ser Glu Asn Gly Val
        35                  40                  45

Thr Leu Ala Pro Glu Asp Thr Leu Pro Phe Leu Lys Cys Tyr Cys Ser
    50                  55                  60

Gly His Cys Pro Asp Asp Ala Ile Asn Asn Thr Cys Ile Thr Asn Gly
65                  70                  75                  80

His Cys Phe Ala Ile Ile Glu Glu Asp Asp Gln Gly Glu Thr Thr Leu
                85                  90                  95

Ala Ser Gly Cys Met Lys Tyr Glu Gly Ser Asp Phe Gln Cys Lys Asp
            100                 105                 110

Ser Pro Lys Ala Gln Leu Arg Arg Thr Ile Glu Cys Cys Arg Thr Asn
        115                 120                 125

Leu Cys Asn Gln Tyr Leu Gln Pro Thr Leu Pro Val Val Ile Gly
    130                 135                 140

Pro Phe Phe Asp Gly Ser Ile Arg Trp Leu Val Leu Leu Ile Ser Met
145                 150                 155                 160

Ala Val Cys Ile Ile Ala Met Ile Ile Phe Ser Ser Cys Phe Cys Tyr
                165                 170                 175

Lys His Tyr Cys Lys Ser Ile Ser Ser Arg Arg Arg Tyr Asn Arg Asp
            180                 185                 190

Leu Glu Gln Asp Glu Ala Phe Ile Pro Val Gly Glu Ser Leu Lys Asp
        195                 200                 205

Leu Ile Asp Gln Ser Gln Ser Ser Gly Ser Gly Ser Gly Leu Pro Leu
    210                 215                 220

Leu Val Gln Arg Thr Ile Ala Lys Gln Ile Gln Met Val Arg Gln Val
225                 230                 235                 240

Gly Lys Gly Arg Tyr Gly Glu Val Trp Met Gly Lys Trp Arg Gly Glu
                245                 250                 255

Lys Val Ala Val Lys Val Phe Phe Thr Thr Glu Glu Ala Ser Trp Phe
            260                 265                 270
```

```
Arg Glu Thr Glu Ile Tyr Gln Thr Val Leu Met Arg His Glu Asn Ile
        275                 280                 285

Leu Gly Phe Ile Ala Ala Asp Ile Lys Gly Thr Gly Ser Trp Thr Gln
        290                 295                 300

Leu Tyr Leu Ile Thr Asp Tyr His Glu Asn Gly Ser Leu Tyr Asp Phe
305                 310                 315                 320

Leu Lys Cys Ala Thr Leu Asp Thr Arg Ala Leu Leu Lys Leu Ala Tyr
                325                 330                 335

Ser Ala Ala Cys Gly Leu Cys His Leu His Thr Glu Ile Tyr Gly Thr
                340                 345                 350

Gln Gly Lys Pro Ala Ile Ala His Arg Asp Leu Lys Ser Lys Asn Ile
                355                 360                 365

Leu Ile Lys Lys Asn Gly Ser Cys Cys Ile Ala Asp Leu Gly Leu Ala
370                 375                 380

Val Lys Phe Asn Ser Asp Thr Asn Glu Val Asp Val Pro Leu Asn Thr
385                 390                 395                 400

Arg Val Gly Thr Lys Arg Tyr Met Ala Pro Glu Val Leu Asp Glu Ser
                405                 410                 415

Leu Asn Lys Asn His Phe Gln Pro Tyr Ile Met Ala Asp Ile Tyr Ser
                420                 425                 430

Phe Gly Leu Ile Ile Trp Glu Met Ala Arg Arg Cys Ile Thr Gly Gly
        435                 440                 445

Ile Val Glu Glu Tyr Gln Leu Pro Tyr Tyr Asn Met Val Pro Ser Asp
450                 455                 460

Pro Ser Tyr Glu Asp Met Arg Glu Val Val Cys Val Lys Arg Leu Arg
465                 470                 475                 480

Pro Ile Val Ser Asn Arg Trp Asn Ser Asp Glu Cys Leu Arg Ala Val
                485                 490                 495

Leu Lys Leu Met Ser Glu Cys Trp Ala His Asn Pro Ala Ser Arg Leu
                500                 505                 510

Thr Ala Leu Arg Ile Lys Lys Thr Leu Ala Lys Met Val Glu Ser Gln
                515                 520                 525

Asp Val Lys Ile
        530

(2) INFORMATION FOR SEQ ID NO: 7:

(i) SEQUENCE CHARACTERISTICS:
        (A) LENGTH: 2333 base pairs
        (B) TYPE: nucleic acid
        (C) STRANDEDNESS: unknown
        (D) TOPOLOGY: linear (ii) MOLECULE TYPE: cDNA (iii) HYPOTHETICAL: NO (iv) ANTI-SENSE: NO (v) FRAGMENT TYPE: internal (vi) ORIGINAL SOURCE:
        (A) ORGANISM: Homo sapiens (ix) FEATURE:
        (A) NAME/KEY: CDS
        (B) LOCATION: 1..1515

(xi) SEQUENCE DESCRIPTION: SEQ ID NO: 7:

ATG GCG GAG TCG GCC GGA GCC TCC TCC TTC TTC CCC CTT GTT GTC CTC      48
Met Ala Glu Ser Ala Gly Ala Ser Ser Phe Phe Pro Leu Val Val Leu
 1               5                  10                  15
```

| | | | | | | | | | | | | | | | | |
|---|---|---|---|---|---|---|---|---|---|---|---|---|---|---|---|---|
| CTG | CTC | GCC | GGC | AGC | GGC | GGG | TCC | GGG | CCC | CGG | GGG | GTC | CAG | GCT | CTG | 96 |
| Leu | Leu | Ala | Gly | Ser | Gly | Gly | Ser | Gly | Pro | Arg | Gly | Val | Gln | Ala | Leu | |
| | | 20 | | | | | 25 | | | | | 30 | | | | |
| CTG | TGT | GCG | TGC | ACC | AGC | TGC | CTC | CAG | GCC | AAC | TAC | ACG | TGT | GAG | ACA | 144 |
| Leu | Cys | Ala | Cys | Thr | Ser | Cys | Leu | Gln | Ala | Asn | Tyr | Thr | Cys | Glu | Thr | |
| | | 35 | | | | | 40 | | | | | 45 | | | | |
| GAT | GGG | GCC | TGC | ATG | GTT | TCC | TTT | TTC | AAT | CTG | GAT | GGG | ATG | GAG | CAC | 192 |
| Asp | Gly | Ala | Cys | Met | Val | Ser | Phe | Phe | Asn | Leu | Asp | Gly | Met | Glu | His | |
| | 50 | | | | | 55 | | | | | 60 | | | | | |
| CAT | GTG | CGC | ACC | TGC | ATC | CCC | AAA | GTG | GAG | CTG | GTC | CCT | GCC | GGG | AAG | 240 |
| His | Val | Arg | Thr | Cys | Ile | Pro | Lys | Val | Glu | Leu | Val | Pro | Ala | Gly | Lys | |
| 65 | | | | 70 | | | | | 75 | | | | | 80 | | |
| CCC | TTC | TAC | TGC | CTG | AGC | TCG | GAG | GAC | CTG | CGC | AAC | ACC | CAC | TGC | TGC | 288 |
| Pro | Phe | Tyr | Cys | Leu | Ser | Ser | Glu | Asp | Leu | Arg | Asn | Thr | His | Cys | Cys | |
| | | | | 85 | | | | | 90 | | | | | 95 | | |
| TAC | ACT | GAC | TAC | TGC | AAC | AGG | ATC | GAC | TTG | AGG | GTG | CCC | AGT | GGT | CAC | 336 |
| Tyr | Thr | Asp | Tyr | Cys | Asn | Arg | Ile | Asp | Leu | Arg | Val | Pro | Ser | Gly | His | |
| | | | | 100 | | | | | 105 | | | | | 110 | | |
| CTC | AAG | GAG | CCT | GAG | CAC | CCG | TCC | ATG | TGG | GGC | CCG | GTG | GAG | CTG | GTA | 384 |
| Leu | Lys | Glu | Pro | Glu | His | Pro | Ser | Met | Trp | Gly | Pro | Val | Glu | Leu | Val | |
| | | | | 115 | | | | | 120 | | | | | 125 | | |
| GGC | ATC | ATC | GCC | GGC | CCG | GTG | TTC | CTC | CTG | TTC | CTC | ATC | ATC | ATC | ATT | 432 |
| Gly | Ile | Ile | Ala | Gly | Pro | Val | Phe | Leu | Leu | Phe | Leu | Ile | Ile | Ile | Ile | |
| | 130 | | | | | 135 | | | | | 140 | | | | | |
| GTT | TTC | CTT | GTC | ATT | AAC | TAT | CAT | CAG | CGT | GTC | TAT | CAC | AAC | CGC | CAG | 480 |
| Val | Phe | Leu | Val | Ile | Asn | Tyr | His | Gln | Arg | Val | Tyr | His | Asn | Arg | Gln | |
| 145 | | | | | 150 | | | | | 155 | | | | | 160 | |
| AGA | CTG | GAC | ATG | GAA | GAT | CCC | TCA | TGT | GAG | ATG | TGT | CTC | TCC | AAA | GAC | 528 |
| Arg | Leu | Asp | Met | Glu | Asp | Pro | Ser | Cys | Glu | Met | Cys | Leu | Ser | Lys | Asp | |
| | | | | 165 | | | | | 170 | | | | | 175 | | |
| AAG | ACG | CTC | CAG | GAT | CTT | GTC | TAC | GAT | CTC | TCC | ACC | TCA | GGG | TCT | GGC | 576 |
| Lys | Thr | Leu | Gln | Asp | Leu | Val | Tyr | Asp | Leu | Ser | Thr | Ser | Gly | Ser | Gly | |
| | | | 180 | | | | | 185 | | | | | 190 | | | |
| TCA | GGG | TTA | CCC | CTC | TTT | GTC | CAG | CGC | ACA | GTG | GCC | CGA | ACC | ATC | GTT | 624 |
| Ser | Gly | Leu | Pro | Leu | Phe | Val | Gln | Arg | Thr | Val | Ala | Arg | Thr | Ile | Val | |
| | | 195 | | | | | 200 | | | | | 205 | | | | |
| TTA | CAA | GAG | ATT | ATT | GGC | AAG | GGT | CGG | TTT | GGG | GAA | GTA | TGG | CGG | GGC | 672 |
| Leu | Gln | Glu | Ile | Ile | Gly | Lys | Gly | Arg | Phe | Gly | Glu | Val | Trp | Arg | Gly | |
| | 210 | | | | | 215 | | | | | 220 | | | | | |
| CGC | TGG | AGG | GGT | GGT | GAT | GTG | GCT | GTG | AAA | ATA | TTC | TCT | TCT | CGT | GAA | 720 |
| Arg | Trp | Arg | Gly | Gly | Asp | Val | Ala | Val | Lys | Ile | Phe | Ser | Ser | Arg | Glu | |
| 225 | | | | | 230 | | | | | 235 | | | | | 240 | |
| GAA | CGG | TCT | TGG | TTC | AGG | GAA | GCA | GAG | ATA | TAC | CAG | ACG | GTC | ATG | CTG | 768 |
| Glu | Arg | Ser | Trp | Phe | Arg | Glu | Ala | Glu | Ile | Tyr | Gln | Thr | Val | Met | Leu | |
| | | | | 245 | | | | | 250 | | | | | 255 | | |
| CGC | CAT | GAA | AAC | ATC | CTT | GGA | TTT | ATT | GCT | GCT | GAC | AAT | AAA | GAT | AAT | 816 |
| Arg | His | Glu | Asn | Ile | Leu | Gly | Phe | Ile | Ala | Ala | Asp | Asn | Lys | Asp | Asn | |
| | | | 260 | | | | | 265 | | | | | 270 | | | |
| GGC | ACC | TGG | ACA | CAG | CTG | TGG | CTT | GTT | TCT | GAC | TAT | CAT | GAG | CAC | GGG | 864 |
| Gly | Thr | Trp | Thr | Gln | Leu | Trp | Leu | Val | Ser | Asp | Tyr | His | Glu | His | Gly | |
| | | 275 | | | | | 280 | | | | | 285 | | | | |
| TCC | CTG | TTT | GAT | TAT | CTG | AAC | CGG | TAC | ACA | GTG | ACA | ATT | GAG | GGG | ATG | 912 |
| Ser | Leu | Phe | Asp | Tyr | Leu | Asn | Arg | Tyr | Thr | Val | Thr | Ile | Glu | Gly | Met | |
| | 290 | | | | | 295 | | | | | 300 | | | | | |
| ATT | AAG | CTG | GCC | TTG | TCT | GCT | GCT | AGT | GGG | CTG | GCA | CAC | CTG | CAC | ATG | 960 |
| Ile | Lys | Leu | Ala | Leu | Ser | Ala | Ala | Ser | Gly | Leu | Ala | His | Leu | His | Met | |
| 305 | | | | | 310 | | | | | 315 | | | | | 320 | |
| GAG | ATC | GTG | GGC | ACC | CAA | GGG | AAG | CCT | GGA | ATT | GCT | CAT | CGA | GAC | TTA | 1008 |
| Glu | Ile | Val | Gly | Thr | Gln | Gly | Lys | Pro | Gly | Ile | Ala | His | Arg | Asp | Leu | |
| | | | | 325 | | | | | 330 | | | | | 335 | | |

```
AAG TCA AAG AAC ATT CTG GTG AAG AAA AAT GGC ATG TGT GCC ATA GCA       1056
Lys Ser Lys Asn Ile Leu Val Lys Lys Asn Gly Met Cys Ala Ile Ala
        340                 345                 350

GAC CTG GGC CTG GCT GTC CGT CAT GAT GCA GTC ACT GAC ACC ATT GAC       1104
Asp Leu Gly Leu Ala Val Arg His Asp Ala Val Thr Asp Thr Ile Asp
                355                 360                 365

ATT GCC CCG AAT CAG AGG GTG GGG ACC AAA CGA TAC ATG GCC CCT GAA       1152
Ile Ala Pro Asn Gln Arg Val Gly Thr Lys Arg Tyr Met Ala Pro Glu
370                 375                 380

GTA CTT GAT GAA ACC ATT AAT ATG AAA CAC TTT GAC TCC TTT AAA TGT       1200
Val Leu Asp Glu Thr Ile Asn Met Lys His Phe Asp Ser Phe Lys Cys
385                 390                 395                 400

GCT GAT ATT TAT GCC CTC GGG CTT GTA TAT TGG GAG ATT GCT CGA AGA       1248
Ala Asp Ile Tyr Ala Leu Gly Leu Val Tyr Trp Glu Ile Ala Arg Arg
                405                 410                 415

TGC AAT TCT GGA GGA GTC CAT GAA GAA TAT CAG CTG CCA TAT TAC GAC       1296
Cys Asn Ser Gly Gly Val His Glu Glu Tyr Gln Leu Pro Tyr Tyr Asp
                420                 425                 430

TTA GTG CCC TCT GAC CCT TCC ATT GAG GAA ATG CGA AAG GTT GTA TGT       1344
Leu Val Pro Ser Asp Pro Ser Ile Glu Glu Met Arg Lys Val Val Cys
                435                 440                 445

GAT CAG AAG CTG CGT CCC AAC ATC CCC AAC TGG TGG CAG AGT TAT GAG       1392
Asp Gln Lys Leu Arg Pro Asn Ile Pro Asn Trp Trp Gln Ser Tyr Glu
450                 455                 460

GCA CTG CGG GTG ATG GGG AAG ATG ATG CGA GAG TGT TGG TAT GCC AAC       1440
Ala Leu Arg Val Met Gly Lys Met Met Arg Glu Cys Trp Tyr Ala Asn
465                 470                 475                 480

GGC GCA GCC CGC CTG ACG GCC CTG CGC ATC AAG AAG ACC CTC TCC CAG       1488
Gly Ala Ala Arg Leu Thr Ala Leu Arg Ile Lys Lys Thr Leu Ser Gln
                485                 490                 495

CTC AGC GTG CAG GAA GAC GTG AAG ATC TAACTGCTCC CTCTCTCCAC             1535
Leu Ser Val Gln Glu Asp Val Lys Ile
                500                 505

ACGGAGCTCC TGGCAGCGAG AACTACGCAC AGCTGCCGCG TTGAGCGTAC GATGGAGGCC     1595

TACCTCTCGT TTCTGCCCAG CCCTCTGTGG CCAGGAGCCC TGGCCCGCAA GAGGGACAGA     1655

GCCCGGGAGA GACTCGCTCA CTCCCATGTT GGGTTTGAGA CAGACACCTT TTCTATTTAC     1715

CTCCTAATGG CATGGAGACT CTGAGAGCGA ATTGTGTGGA GAACTCAGTG CCACACCTCG     1775

AACTGGTTGT AGTGGGAAGT CCCGCGAAAC CCGGTGCATC TGGCACGTGG CCAGGAGCCA     1835

TGACAGGGGC GCTTGGGAGG GGCCGGAGGA ACCGAGGTGT TGCCAGTGCT AAGCTGCCCT     1895

GAGGGTTTCC TTCGGGGACC AGCCCACAGC ACACCAAGGT GGCCCGGAAG AACCAGAAGT     1955

GCAGCCCCTC TCACAGGCAG CTCTGAGCCG CGCTTTCCCC TCCTCCCTGG GATGGACGCT     2015

GCCGGGAGAC TGCCAGTGGA GACGGAATCT GCCGCTTTGT CTGTCCAGCC GTGTGTGCAT     2075

GTGCCGAGGT GCGTCCCCCG TTGTGCCTGG TTCGTGCCAT GCCCTTACAC GTGCGTGTGA     2135

GTGTGTGTGT GTGTCTGTAG GTGCGCACTT ACCTGCTTGA GCTTTCTGTG CATGTGCAGG     2195

TCGGGGGTGT GGTCGTCATG CTGTCCGTGC TTGCTGGTGC CTCTTTTCAG TAGTGAGCAG     2255

CATCTAGTTT CCCTGGTGCC CTTCCCTGGA GGTCTCTCCC TCCCCCAGAG CCCCTCATGC     2315

CACAGTGGTA CTCTGTGT                                                   2333

(2) INFORMATION FOR SEQ ID NO: 8:

(i) SEQUENCE CHARACTERISTICS:
          (A) LENGTH: 505 amino acids
          (B) TYPE: amino acid
          (D) TOPOLOGY: linear
```

(ii) MOLECULE TYPE: protein (xi) SEQUENCE DESCRIPTION: SEQ ID NO: 8:

```
Met Ala Glu Ser Ala Gly Ala Ser Ser Phe Phe Pro Leu Val Val Leu
 1               5                  10                  15

Leu Leu Ala Gly Ser Gly Gly Ser Gly Pro Arg Gly Val Gln Ala Leu
            20                  25                  30

Leu Cys Ala Cys Thr Ser Cys Leu Gln Ala Asn Tyr Thr Cys Glu Thr
            35                  40                  45

Asp Gly Ala Cys Met Val Ser Phe Phe Asn Leu Asp Gly Met Glu His
        50                  55                  60

His Val Arg Thr Cys Ile Pro Lys Val Glu Leu Val Pro Ala Gly Lys
65                  70                  75                  80

Pro Phe Tyr Cys Leu Ser Ser Glu Asp Leu Arg Asn Thr His Cys Cys
                85                  90                  95

Tyr Thr Asp Tyr Cys Asn Arg Ile Asp Leu Arg Val Pro Ser Gly His
            100                 105                 110

Leu Lys Glu Pro Glu His Pro Ser Met Trp Gly Pro Val Glu Leu Val
        115                 120                 125

Gly Ile Ile Ala Gly Pro Val Phe Leu Leu Phe Leu Ile Ile Ile Ile
130                 135                 140

Val Phe Leu Val Ile Asn Tyr His Gln Arg Val Tyr His Asn Arg Gln
145                 150                 155                 160

Arg Leu Asp Met Glu Asp Pro Ser Cys Glu Met Cys Leu Ser Lys Asp
                165                 170                 175

Lys Thr Leu Gln Asp Leu Val Tyr Asp Leu Ser Thr Ser Gly Ser Gly
            180                 185                 190

Ser Gly Leu Pro Leu Phe Val Gln Arg Thr Val Ala Arg Thr Ile Val
        195                 200                 205

Leu Gln Glu Ile Ile Gly Lys Gly Arg Phe Gly Glu Val Trp Arg Gly
210                 215                 220

Arg Trp Arg Gly Gly Asp Val Ala Val Lys Ile Phe Ser Ser Arg Glu
225                 230                 235                 240

Glu Arg Ser Trp Phe Arg Glu Ala Glu Ile Tyr Gln Thr Val Met Leu
                245                 250                 255

Arg His Glu Asn Ile Leu Gly Phe Ile Ala Ala Asp Asn Lys Asp Asn
            260                 265                 270

Gly Thr Trp Thr Gln Leu Trp Leu Val Ser Asp Tyr His Glu His Gly
        275                 280                 285

Ser Leu Phe Asp Tyr Leu Asn Arg Tyr Thr Val Thr Ile Glu Gly Met
290                 295                 300

Ile Lys Leu Ala Leu Ser Ala Ala Ser Gly Leu Ala His Leu His Met
305                 310                 315                 320

Glu Ile Val Gly Thr Gln Gly Lys Pro Gly Ile Ala His Arg Asp Leu
                325                 330                 335

Lys Ser Lys Asn Ile Leu Val Lys Lys Asn Gly Met Cys Ala Ile Ala
            340                 345                 350

Asp Leu Gly Leu Ala Val Arg His Asp Ala Val Thr Asp Thr Ile Asp
        355                 360                 365

Ile Ala Pro Asn Gln Arg Val Gly Thr Lys Arg Tyr Met Ala Pro Glu
370                 375                 380

Val Leu Asp Glu Thr Ile Asn Met Lys His Phe Asp Ser Phe Lys Cys
385                 390                 395                 400
```

```
Ala Asp Ile Tyr Ala Leu Gly Leu Val Tyr Trp Glu Ile Ala Arg Arg
            405                 410                 415

Cys Asn Ser Gly Gly Val His Glu Glu Tyr Gln Leu Pro Tyr Tyr Asp
        420                 425                 430

Leu Val Pro Ser Asp Pro Ser Ile Glu Glu Met Arg Lys Val Val Cys
        435                 440                 445

Asp Gln Lys Leu Arg Pro Asn Ile Pro Asn Trp Trp Gln Ser Tyr Glu
450                 455                 460

Ala Leu Arg Val Met Gly Lys Met Met Arg Glu Cys Trp Tyr Ala Asn
465                 470                 475                 480

Gly Ala Ala Arg Leu Thr Ala Leu Arg Ile Lys Lys Thr Leu Ser Gln
                485                 490                 495

Leu Ser Val Gln Glu Asp Val Lys Ile
                500                 505
```

(2) INFORMATION FOR SEQ ID NO: 9:

(i) SEQUENCE CHARACTERISTICS:
       (A) LENGTH: 2308 base pairs
       (B) TYPE: nucleic acid
       (C) STRANDEDNESS: unknown
       (D) TOPOLOGY: linear (ii) MOLECULE TYPE: cDNA (iii) HYPOTHETICAL: NO (iv) ANTI-SENSE: NO (v) FRAGMENT TYPE: internal (vi) ORIGINAL SOURCE:
       (A) ORGANISM: Mouse (ix) FEATURE:
       (A) NAME/KEY: CDS
       (B) LOCATION: 77..1585

(xi) SEQUENCE DESCRIPTION: SEQ ID NO: 9:

```
GGCGAGGCGA GGTTTGCTGG GGTGAGGCAG CGGCGCGGCC GGGCCGGGCC GGGCCACAGG      60

CGGTGGCGGC GGGACC ATG GAG GCG GCG GTC GCT GCT CCG CGT CCC CGG        109
                  Met Glu Ala Ala Val Ala Ala Pro Arg Pro Arg
                    1               5                  10

CTG CTC CTC CTC GTG CTG GCG GCG GCG GCG GCG GCG GCG GCG GCG CTG     157
Leu Leu Leu Leu Val Leu Ala Ala Ala Ala Ala Ala Ala Ala Ala Leu
                 15                  20                  25

CTC CCG GGG GCG ACG GCG TTA CAG TGT TTC TGC CAC CTC TGT ACA AAA     205
Leu Pro Gly Ala Thr Ala Leu Gln Cys Phe Cys His Leu Cys Thr Lys
            30                  35                  40

GAC AAT TTT ACT TGT GTG ACA GAT GGG CTC TGC TTT GTC TCT GTC ACA     253
Asp Asn Phe Thr Cys Val Thr Asp Gly Leu Cys Phe Val Ser Val Thr
        45                  50                  55

GAG ACC ACA GAC AAA GTT ATA CAC AAC AGC ATG TGT ATA GCT GAA ATT     301
Glu Thr Thr Asp Lys Val Ile His Asn Ser Met Cys Ile Ala Glu Ile
 60                  65                  70                  75

GAC TTA ATT CCT CGA GAT AGG CCG TTT GTA TGT GCA CCC TCT TCA AAA     349
Asp Leu Ile Pro Arg Asp Arg Pro Phe Val Cys Ala Pro Ser Ser Lys
                80                  85                  90

ACT GGG TCT GTG ACT ACA ACA TAT TGC TGC AAT CAG GAC CAT TGC AAT     397
Thr Gly Ser Val Thr Thr Thr Tyr Cys Cys Asn Gln Asp His Cys Asn
            95                 100                 105

AAA ATA GAA CTT CCA ACT ACT GTA AAG TCA TCA CCT GGC CTT GGT CCT     445
Lys Ile Glu Leu Pro Thr Thr Val Lys Ser Ser Pro Gly Leu Gly Pro
       110                 115                 120
```

-continued

```
GTG GAA CTG GCA GCT GTC ATT GCT GGA CCA GTG TGC TTC GTC TGC ATC      493
Val Glu Leu Ala Ala Val Ile Ala Gly Pro Val Cys Phe Val Cys Ile
    125                 130                 135

TCA CTC ATG TTG ATG GTC TAT ATC TGC CAC AAC CGC ACT GTC ATT CAC      541
Ser Leu Met Leu Met Val Tyr Ile Cys His Asn Arg Thr Val Ile His
140                 145                 150                 155

CAT CGA GTG CCA AAT GAA GAG GAC CCT TCA TTA GAT CGC CCT TTT ATT      589
His Arg Val Pro Asn Glu Glu Asp Pro Ser Leu Asp Arg Pro Phe Ile
                160                 165                 170

TCA GAG GGT ACT ACG TTG AAA GAC TTA ATT TAT GAT ATG ACA ACG TCA      637
Ser Glu Gly Thr Thr Leu Lys Asp Leu Ile Tyr Asp Met Thr Thr Ser
            175                 180                 185

GGT TCT GGC TCA GGT TTA CCA TTG CTT GTT CAG AGA ACA ATT GCG AGA      685
Gly Ser Gly Ser Gly Leu Pro Leu Leu Val Gln Arg Thr Ile Ala Arg
        190                 195                 200

ACT ATT GTG TTA CAA GAA AGC ATT GGC AAA GGT CGA TTT GGA GAA GTT      733
Thr Ile Val Leu Gln Glu Ser Ile Gly Lys Gly Arg Phe Gly Glu Val
    205                 210                 215

TGG AGA GGA AAG TGG CGG GGA GAA GAA GTT GCT GTT AAG ATA TTC TCC      781
Trp Arg Gly Lys Trp Arg Gly Glu Glu Val Ala Val Lys Ile Phe Ser
220                 225                 230                 235

TCT AGA GAA GAA CGT TCG TGG TTC CGT GAG GCA GAG ATT TAT CAA ACT      829
Ser Arg Glu Glu Arg Ser Trp Phe Arg Glu Ala Glu Ile Tyr Gln Thr
                240                 245                 250

GTA ATG TTA CGT CAT GAA AAC ATC CTG GGA TTT ATA GCA GCA GAC AAT      877
Val Met Leu Arg His Glu Asn Ile Leu Gly Phe Ile Ala Ala Asp Asn
            255                 260                 265

AAA GAC AAT GGT ACT TGG ACT CAG CTC TGG TTG GTG TCA GAT TAT CAT      925
Lys Asp Asn Gly Thr Trp Thr Gln Leu Trp Leu Val Ser Asp Tyr His
        270                 275                 280

GAG CAT GGA TCC CTT TTT GAT TAC TTA AAC AGA TAC ACA GTT ACT GTG      973
Glu His Gly Ser Leu Phe Asp Tyr Leu Asn Arg Tyr Thr Val Thr Val
    285                 290                 295

GAA GGA ATG ATA AAA CTT GCT CTG TCC ACG GCG AGC GGT CTT GCC CAT     1021
Glu Gly Met Ile Lys Leu Ala Leu Ser Thr Ala Ser Gly Leu Ala His
300                 305                 310                 315

CTT CAC ATG GAG ATT GTT GGT ACC CAA GGA AAG CCA GCC ATT GCT CAT     1069
Leu His Met Glu Ile Val Gly Thr Gln Gly Lys Pro Ala Ile Ala His
                320                 325                 330

AGA GAT TTG AAA TCA AAG AAT ATC TTG GTA AAG AAG AAT GGA ACT TGC     1117
Arg Asp Leu Lys Ser Lys Asn Ile Leu Val Lys Lys Asn Gly Thr Cys
            335                 340                 345

TGT ATT GCA GAC TTA GGA CTG GCA GTA AGA CAT GAT TCA GCC ACA GAT     1165
Cys Ile Ala Asp Leu Gly Leu Ala Val Arg His Asp Ser Ala Thr Asp
        350                 355                 360

ACC ATT GAT ATT GCT CCA AAC CAC AGA GTG GGA ACA AAA AGG TAC ATG     1213
Thr Ile Asp Ile Ala Pro Asn His Arg Val Gly Thr Lys Arg Tyr Met
    365                 370                 375

GCC CCT GAA GTT CTC GAT GAT TCC ATA AAT ATG AAA CAT TTT GAA TCC     1261
Ala Pro Glu Val Leu Asp Asp Ser Ile Asn Met Lys His Phe Glu Ser
380                 385                 390                 395

TTC AAA CGT GCT GAC ATC TAT GCA ATG GGC TTA GTA TTC TGG GAA ATT     1309
Phe Lys Arg Ala Asp Ile Tyr Ala Met Gly Leu Val Phe Trp Glu Ile
                400                 405                 410

GCT CGA CGA TGT TCC ATT GGT GGA ATT CAT GAA GAT TAC CAA CTG CCT     1357
Ala Arg Arg Cys Ser Ile Gly Gly Ile His Glu Asp Tyr Gln Leu Pro
            415                 420                 425

TAT TAT GAT CTT GTA CCT TCT GAC CCA TCA GTT GAA GAA ATG AGA AAA     1405
Tyr Tyr Asp Leu Val Pro Ser Asp Pro Ser Val Glu Glu Met Arg Lys
        430                 435                 440
```

-continued

```
GTT GTT TGT GAA CAG AAG TTA AGG CCA AAT ATC CCA AAC AGA TGG CAG        1453
Val Val Cys Glu Gln Lys Leu Arg Pro Asn Ile Pro Asn Arg Trp Gln
445                 450                 455

AGC TGT GAA GCC TTG AGA GTA ATG GCT AAA ATT ATG AGA GAA TGT TGG        1501
Ser Cys Glu Ala Leu Arg Val Met Ala Lys Ile Met Arg Glu Cys Trp
460                 465                 470                 475

TAT GCC AAT GGA GCA GCT AGG CTT ACA GCA TTG CGG ATT AAG AAA ACA        1549
Tyr Ala Asn Gly Ala Ala Arg Leu Thr Ala Leu Arg Ile Lys Lys Thr
                480                 485                 490

TTA TCG CAA CTC AGT CAA CAG GAA GGC ATC AAA ATG TAATTCTACA             1595
Leu Ser Gln Leu Ser Gln Gln Glu Gly Ile Lys Met
            495                 500

GCTTTGCCTG AACTCCCTT TTTTCTTCAG ATCTGCTCCT GGGTTTTAAT TTGGGAGGTC       1655

AGTTGTTCTA CCTCACTGAG AGGGAACAGA AGGATATTGC TTCCTTTTGC AGCAGTGTAA      1715

TAAAGTCAAT TAAAAACTTC CCAGGATTTC TTTGGACCCA GGAAACAGCC ATGTGGGTCC      1775

TTTCTGTGCA CTATGAACGC TTCTTTCCCA GGACAGAAAA TGTGTAGTCT ACCTTTATTT      1835

TTTATTAACA AAACTTGTTT TTTAAAAAGA TGATTGCTGG TCTTAACTTT AGGTAACTCT      1895

GCTGTGCTGG AGATCATCTT TAAGGGCAAA GGAGTTGGAT TGCTGAATTA CAATGAAACA      1955

TGTCTTATTA CTAAAGAAAG TGATTTACTC CTGGTTAGTA CATTCTCAGA GGATTCTGAA      2015

CCACTAGAGT TTCCTTGATT CAGACTTTGA ATGTACTGTT CTATAGTTTT TCAGGATCTT      2075

AAAACTAACA CTTATAAAAC TCTTATCTTG AGTCTAAAAA TGACCTCATA TAGTAGTGAG      2135

GAACATAATT CATGCAATTG TATTTGTAT ACTATTATTG TTCTTTCACT TATTCAGAAC       2195

ATTACATGCC TTCAAAATGG GATTGTACTA TACCAGTAAG TGCCACTTCT GTGTCTTTCT      2255

AATGGAAATG AGTAGAATTG CTGAAAGTCT CTATGTTAAA ACCTATAGTG TTT             2308
```

(2) INFORMATION FOR SEQ ID NO: 10:

(i) SEQUENCE CHARACTERISTICS:
        (A) LENGTH: 503 amino acids
        (B) TYPE: amino acid
        (D) TOPOLOGY: linear (ii) MOLECULE TYPE: protein (xi) SEQUENCE DESCRIPTION: SEQ ID NO: 10:

```
Met Glu Ala Ala Val Ala Ala Pro Arg Pro Arg Leu Leu Leu Leu Val
1                   5                   10                  15

Leu Ala Ala Ala Ala Ala Ala Ala Ala Leu Leu Pro Gly Ala Thr
                20                  25                  30

Ala Leu Gln Cys Phe Cys His Leu Cys Thr Lys Asp Asn Phe Thr Cys
            35                  40                  45

Val Thr Asp Gly Leu Cys Phe Val Ser Val Thr Glu Thr Thr Asp Lys
        50                  55                  60

Val Ile His Asn Ser Met Cys Ile Ala Glu Ile Asp Leu Ile Pro Arg
65                  70                  75                  80

Asp Arg Pro Phe Val Cys Ala Pro Ser Ser Lys Thr Gly Ser Val Thr
                85                  90                  95

Thr Thr Tyr Cys Cys Asn Gln Asp His Cys Asn Lys Ile Glu Leu Pro
            100                 105                 110

Thr Thr Val Lys Ser Ser Pro Gly Leu Gly Pro Val Glu Leu Ala Ala
        115                 120                 125

Val Ile Ala Gly Pro Val Cys Phe Val Cys Ile Ser Leu Met Leu Met
130                 135                 140
```

-continued

| | | | | | | | | | | | |
|---|---|---|---|---|---|---|---|---|---|---|---|
|Val|Tyr|Ile|Cys|His|Asn|Arg|Thr|Val|Ile|His|His|
|145| | | | |150| | | | |155| |
|Arg|Val|Pro|Asn| | | | | | | | |
| | | |160| | | | | | | | |
|Glu|Glu|Asp|Pro|Ser|Leu|Asp|Arg|Pro|Phe|Ile|Ser|
| | | | |165| | | | |170| | |
|Glu|Gly|Thr|Thr| | | | | | | | |
| | |175| | | | | | | | | |
|Leu|Lys|Asp|Leu|Ile|Tyr|Asp|Met|Thr|Thr|Ser|Gly|
| | | |180| | | | |185| | | |
|Ser|Gly|Ser|Gly| | | | | | | | |
| |190| | | | | | | | | | |
|Leu|Pro|Leu|Leu|Val|Gln|Arg|Thr|Ile|Ala|Arg|Thr|
| | | |195| | | | |200| | | |
|Ile|Val|Leu|Gln| | | | | | | | |
| |205| | | | | | | | | | |
|Glu|Ser|Ile|Gly|Lys|Gly|Arg|Phe|Gly|Val|Trp|Arg|
| | | |210| | | | |215| | | |
|Gly|Lys|Trp| | | | | | | | | |
| |220| | | | | | | | | | |
|Arg|Gly|Glu|Glu|Val|Ala|Val|Lys|Ile|Phe|Ser|Ser|
|225| | | | |230| | | | |235| |
|Arg|Glu|Glu|Arg| | | | | | | | |
| | | |240| | | | | | | | |
|Ser|Trp|Phe|Arg|Glu|Ala|Glu|Ile|Tyr|Gln|Thr|Val|
| | | |245| | | | |250| | | |
|Met|Leu|Arg|His| | | | | | | | |
| | |255| | | | | | | | | |
|Glu|Asn|Ile|Leu|Gly|Phe|Ile|Ala|Ala|Asp|Asn|Lys|
| | | |260| | | | |265| | | |
|Asp|Asn|Gly|Thr| | | | | | | | |
| |270| | | | | | | | | | |
|Trp|Thr|Gln|Leu|Trp|Leu|Val|Ser|Asp|Tyr|His|Glu|
| | |275| | | | |280| | | | |
|His|Gly|Ser|Leu| | | | | | | | |
|285| | | | | | | | | | | |
|Phe|Asp|Tyr|Leu|Asn|Arg|Tyr|Thr|Val|Thr|Val|Glu|
|290| | | | |295| | | | |300| |
|Gly|Met|Ile|Lys| | | | | | | | |
| | | | | | | | | | | | |
|Leu|Ala|Leu|Ser|Thr|Ala|Ser|Gly|Leu|Ala|His|Leu|
|305| | | | |310| | | | |315| |
|His|Met|Glu|Ile| | | | | | | | |
| | | |320| | | | | | | | |
|Val|Gly|Thr|Gln|Gly|Lys|Pro|Ala|Ile|Ala|His|Arg|
| | | |325| | | | |330| | | |
|Asp|Leu|Lys|Ser| | | | | | | | |
| | |335| | | | | | | | | |
|Lys|Asn|Ile|Leu|Val|Lys|Lys|Asn|Gly|Thr|Cys|Cys|
| | | |340| | | | |345| | | |
|Ile|Ala|Asp|Leu| | | | | | | | |
| |350| | | | | | | | | | |
|Gly|Leu|Ala|Val|Arg|His|Asp|Ser|Ala|Thr|Asp|Thr|
| | |355| | | | |360| | | | |
|Ile|Asp|Ile|Ala| | | | | | | | |
|365| | | | | | | | | | | |
|Pro|Asn|His|Arg|Val|Gly|Thr|Lys|Arg|Tyr|Met|Ala|
|370| | | | |375| | | | |380| |
|Pro|Glu|Val|Leu| | | | | | | | |
| | | | | | | | | | | | |
|Asp|Asp|Ser|Ile|Asn|Met|Lys|His|Phe|Glu|Ser|Phe|
|385| | | | |390| | | | |395| |
|Lys|Arg|Ala|Asp| | | | | | | | |
| | | |400| | | | | | | | |
|Ile|Tyr|Ala|Met|Gly|Leu|Val|Phe|Trp|Glu|Ile|Ala|
| | | |405| | | | |410| | | |
|Arg|Arg|Cys|Ser| | | | | | | | |
| | |415| | | | | | | | | |
|Ile|Gly|Gly|Ile|His|Glu|Asp|Tyr|Gln|Leu|Pro|Tyr|
| | | |420| | | | |425| | | |
|Tyr|Asp|Leu|Val| | | | | | | | |
| |430| | | | | | | | | | |
|Pro|Ser|Asp|Pro|Ser|Val|Glu|Glu|Met|Arg|Lys|Val|
| | | |435| | | | |440| | | |
|Val|Cys|Glu|Gln| | | | | | | | |
|445| | | | | | | | | | | |
|Lys|Leu|Arg|Pro|Asn|Ile|Pro|Asn|Arg|Trp|Gln|Ser|
|450| | | | |455| | | | |460| |
|Cys|Glu|Ala|Leu| | | | | | | | |
| | | | | | | | | | | | |
|Arg|Val|Met|Ala|Lys|Ile|Met|Arg|Glu|Cys|Trp|Tyr|
|465| | | | |470| | | | |475| |
|Ala|Asn|Gly|Ala| | | | | | | | |
| | | |480| | | | | | | | |
|Ala|Arg|Leu|Thr|Ala|Leu|Arg|Ile|Lys|Lys|Thr|Leu|
| | | |485| | | | |490| | | |
|Ser|Gln|Leu|Ser| | | | | | | | |
| |495| | | | | | | | | | |
|Gln|Gln|Glu|Gly|Ile|Lys|Met| | | | | |
| | | |500| | | | | | | | |

(2) INFORMATION FOR SEQ ID NO: 11:

(i) SEQUENCE CHARACTERISTICS:
        (A) LENGTH: 1922 base pairs
        (B) TYPE: nucleic acid
        (C) STRANDEDNESS: unknown
        (D) TOPOLOGY: linear (ii) MOLECULE TYPE: cDNA -continued

```
    (iii) HYPOTHETICAL: NO (iv) ANTI-SENSE: NO (v) FRAGMENT TYPE: internal (vi) ORIGINAL SOURCE:
          (A) ORGANISM: Mouse (ix) FEATURE:
          (A) NAME/KEY: CDS
          (B) LOCATION: 241..1746

(xi) SEQUENCE DESCRIPTION: SEQ ID NO: 11:
```

| | |
|---|---:|
| GAGAGCACAG CCCTTCCCAG TCCCCGGAGC CGCCGCGCCA CGCGCGCATG ATCAAGACCT | 60 |
| TTTCCCCGGC CCCACAGGGC CTCTGGACGT GAGACCCCGG CCGCCTCCGC AAGGAGAGGC | 120 |
| GGGGGTCGAG TCGCCCTGTC CAAAGGCCTC AATCTAAACA ATCTTGATTC CTGTTGCCGG | 180 |
| CTGGCGGGAC CCTGAATGGC AGGAAATCTC ACCACATCTC TTCTCCTATC TCCAAGGACC | 240 |

| | | | | | | | | | | | | | | | | |
|---|---|---|---|---|---|---|---|---|---|---|---|---|---|---|---|---:|
| ATG | ACC | TTG | GGG | AGC | TTC | AGA | AGG | GGC | CTT | TTG | ATG | CTG | TCG | GTG | GCC | 288 |
| Met | Thr | Leu | Gly | Ser | Phe | Arg | Arg | Gly | Leu | Leu | Met | Leu | Ser | Val | Ala | |
| 1 | | | | 5 | | | | | 10 | | | | | 15 | | |

| | | | | | | | | | | | | | | | | |
|---|---|---|---|---|---|---|---|---|---|---|---|---|---|---|---|---:|
| TTG | GGC | CTA | ACC | CAG | GGG | AGA | CTT | GCG | AAG | CCT | TCC | AAG | CTG | GTG | AAC | 336 |
| Leu | Gly | Leu | Thr | Gln | Gly | Arg | Leu | Ala | Lys | Pro | Ser | Lys | Leu | Val | Asn | |
| | | | 20 | | | | | 25 | | | | | 30 | | | |

| | | | | | | | | | | | | | | | | |
|---|---|---|---|---|---|---|---|---|---|---|---|---|---|---|---|---:|
| TGC | ACT | TGT | GAG | AGC | CCA | CAC | TGC | AAG | AGA | CCA | TTC | TGC | CAG | GGG | TCA | 384 |
| Cys | Thr | Cys | Glu | Ser | Pro | His | Cys | Lys | Arg | Pro | Phe | Cys | Gln | Gly | Ser | |
| | | 35 | | | | | 40 | | | | | 45 | | | | |

| | | | | | | | | | | | | | | | | |
|---|---|---|---|---|---|---|---|---|---|---|---|---|---|---|---|---:|
| TGG | TGC | ACA | GTG | GTG | CTG | GTT | CGA | GAG | CAG | GGC | AGG | CAC | CCC | CAG | GTC | 432 |
| Trp | Cys | Thr | Val | Val | Leu | Val | Arg | Glu | Gln | Gly | Arg | His | Pro | Gln | Val | |
| 50 | | | | | 55 | | | | | 60 | | | | | | |

| | | | | | | | | | | | | | | | | |
|---|---|---|---|---|---|---|---|---|---|---|---|---|---|---|---|---:|
| TAT | CGG | GGC | TGT | GGG | AGC | CTG | AAC | CAG | GAG | CTC | TGC | TTG | GGA | CGT | CCC | 480 |
| Tyr | Arg | Gly | Cys | Gly | Ser | Leu | Asn | Gln | Glu | Leu | Cys | Leu | Gly | Arg | Pro | |
| 65 | | | | 70 | | | | | 75 | | | | | 80 | | |

| | | | | | | | | | | | | | | | | |
|---|---|---|---|---|---|---|---|---|---|---|---|---|---|---|---|---:|
| ACG | GAG | TTT | CTG | AAC | CAT | CAC | TGC | TGC | TAT | AGA | TCC | TTC | TGC | AAC | CAC | 528 |
| Thr | Glu | Phe | Leu | Asn | His | His | Cys | Cys | Tyr | Arg | Ser | Phe | Cys | Asn | His | |
| | | | 85 | | | | | 90 | | | | | 95 | | | |

| | | | | | | | | | | | | | | | | |
|---|---|---|---|---|---|---|---|---|---|---|---|---|---|---|---|---:|
| AAC | GTG | TCT | CTG | ATG | CTG | GAG | GCC | ACC | CAA | ACT | CCT | TCG | GAG | GAG | CCA | 576 |
| Asn | Val | Ser | Leu | Met | Leu | Glu | Ala | Thr | Gln | Thr | Pro | Ser | Glu | Glu | Pro | |
| | | 100 | | | | | 105 | | | | | 110 | | | | |

| | | | | | | | | | | | | | | | | |
|---|---|---|---|---|---|---|---|---|---|---|---|---|---|---|---|---:|
| GAA | GTT | GAT | GCC | CAT | CTG | CCT | CTG | ATC | CTG | GGT | CCT | GTG | CTG | GCC | TTG | 624 |
| Glu | Val | Asp | Ala | His | Leu | Pro | Leu | Ile | Leu | Gly | Pro | Val | Leu | Ala | Leu | |
| | | | 115 | | | | | 120 | | | | | 125 | | | |

| | | | | | | | | | | | | | | | | |
|---|---|---|---|---|---|---|---|---|---|---|---|---|---|---|---|---:|
| CCG | GTC | CTG | GTG | GCC | CTG | GGT | GCT | CTG | GGC | TTG | TGG | CGT | GTC | CGG | CGG | 672 |
| Pro | Val | Leu | Val | Ala | Leu | Gly | Ala | Leu | Gly | Leu | Trp | Arg | Val | Arg | Arg | |
| | 130 | | | | | 135 | | | | | 140 | | | | | |

| | | | | | | | | | | | | | | | | |
|---|---|---|---|---|---|---|---|---|---|---|---|---|---|---|---|---:|
| AGG | CAG | GAG | AAG | CAG | CGG | GAT | TTG | CAC | AGT | GAC | CTG | GGC | GAG | TCC | AGT | 720 |
| Arg | Gln | Glu | Lys | Gln | Arg | Asp | Leu | His | Ser | Asp | Leu | Gly | Glu | Ser | Ser | |
| 145 | | | | | 150 | | | | | 155 | | | | | 160 | |

| | | | | | | | | | | | | | | | | |
|---|---|---|---|---|---|---|---|---|---|---|---|---|---|---|---|---:|
| CTC | ATC | CTG | AAG | GCA | TCT | GAA | CAG | GCA | GAC | AGC | ATG | TTG | GGG | GAC | TTC | 768 |
| Leu | Ile | Leu | Lys | Ala | Ser | Glu | Gln | Ala | Asp | Ser | Met | Leu | Gly | Asp | Phe | |
| | | | | 165 | | | | | 170 | | | | | 175 | | |

| | | | | | | | | | | | | | | | | |
|---|---|---|---|---|---|---|---|---|---|---|---|---|---|---|---|---:|
| CTG | GAC | AGC | GAC | TGT | ACC | ACG | GGC | AGC | GGC | TCG | GGG | CTC | CCC | TTC | TTG | 816 |
| Leu | Asp | Ser | Asp | Cys | Thr | Thr | Gly | Ser | Gly | Ser | Gly | Leu | Pro | Phe | Leu | |
| | | | 180 | | | | | 185 | | | | | 190 | | | |

| | | | | | | | | | | | | | | | | |
|---|---|---|---|---|---|---|---|---|---|---|---|---|---|---|---|---:|
| GTG | CAG | AGG | ACG | GTA | GCT | CGG | CAG | GTT | GCG | CTG | GTA | GAG | TGT | GTG | GGA | 864 |
| Val | Gln | Arg | Thr | Val | Ala | Arg | Gln | Val | Ala | Leu | Val | Glu | Cys | Val | Gly | |
| | | 195 | | | | | 200 | | | | | 205 | | | | |

| | | | | | | | | | | | | | | | | |
|---|---|---|---|---|---|---|---|---|---|---|---|---|---|---|---|---:|
| AAG | GGC | CGA | TAT | GGC | GAG | GTG | TGG | CGC | GGT | TCG | TGG | CAT | GGC | GAA | AGC | 912 |
| Lys | Gly | Arg | Tyr | Gly | Glu | Val | Trp | Arg | Gly | Ser | Trp | His | Gly | Glu | Ser | |
| | 210 | | | | | 215 | | | | | 220 | | | | | |

| | | | | | | | | | | | | | | | | |
|---|---|---|---|---|---|---|---|---|---|---|---|---|---|---|---|---:|
| GTG | GCG | GTC | AAG | ATT | TTC | TCC | TCA | CGA | GAT | GAG | CAG | TCC | TGG | TTC | CGG | 960 |

```
Val Ala Val Lys Ile Phe Ser Ser Arg Asp Glu Gln Ser Trp Phe Arg
225                 230                 235                 240

GAG ACG GAG ATC TAC AAC ACA GTT CTG CTT AGA CAC GAC AAC ATC CTA        1008
Glu Thr Glu Ile Tyr Asn Thr Val Leu Leu Arg His Asp Asn Ile Leu
                    245                 250                 255

GGC TTC ATC GCC TCC GAC ATG ACT TCG CGG AAC TCG AGC ACG CAG CTG        1056
Gly Phe Ile Ala Ser Asp Met Thr Ser Arg Asn Ser Ser Thr Gln Leu
                260                 265                 270

TGG CTC ATC ACC CAC TAC CAT GAA CAC GGC TCC CTC TAT GAC TTT CTG        1104
Trp Leu Ile Thr His Tyr His Glu His Gly Ser Leu Tyr Asp Phe Leu
            275                 280                 285

CAG AGG CAG ACG CTG GAG CCC CAG TTG GCC CTG AGG CTA GCT GTG TCC        1152
Gln Arg Gln Thr Leu Glu Pro Gln Leu Ala Leu Arg Leu Ala Val Ser
        290                 295                 300

CCG GCC TGC GGC CTG GCG CAC CTA CAT GTG GAG ATC TTT GGC ACT CAA        1200
Pro Ala Cys Gly Leu Ala His Leu His Val Glu Ile Phe Gly Thr Gln
305                 310                 315                 320

GGC AAA CCA GCC ATT GCC CAT CGT GAC CTC AAG AGT CGC AAT GTG CTG        1248
Gly Lys Pro Ala Ile Ala His Arg Asp Leu Lys Ser Arg Asn Val Leu
                    325                 330                 335

GTC AAG AGT AAC TTG CAG TGT TGC ATT GCA GAC CTG GGA CTG GCT GTG        1296
Val Lys Ser Asn Leu Gln Cys Cys Ile Ala Asp Leu Gly Leu Ala Val
                340                 345                 350

ATG CAC TCA CAA AGC AAC GAG TAC CTG GAT ATC GGC AAC ACA CCC CGA        1344
Met His Ser Gln Ser Asn Glu Tyr Leu Asp Ile Gly Asn Thr Pro Arg
            355                 360                 365

GTG GGT ACC AAA AGA TAC ATG GCA CCC GAG GTG CTG GAT GAG CAC ATC        1392
Val Gly Thr Lys Arg Tyr Met Ala Pro Glu Val Leu Asp Glu His Ile
        370                 375                 380

CGC ACA GAC TGC TTT GAG TCG TAC AAG TGG ACA GAC ATC TGG GCC TTT        1440
Arg Thr Asp Cys Phe Glu Ser Tyr Lys Trp Thr Asp Ile Trp Ala Phe
385                 390                 395                 400

GGC CTA GTG CTA TGG GAG ATC GCC CGG CGG ACC ATC ATC AAT GGC ATT        1488
Gly Leu Val Leu Trp Glu Ile Ala Arg Arg Thr Ile Ile Asn Gly Ile
                    405                 410                 415

GTG GAG GAT TAC AGG CCA CCT TTC TAT GAC ATG GTA CCC AAT GAC CCC        1536
Val Glu Asp Tyr Arg Pro Pro Phe Tyr Asp Met Val Pro Asn Asp Pro
                420                 425                 430

AGT TTT GAG GAC ATG AAA AAG GTG GTG TGC GTT GAC CAG CAG ACA CCC        1584
Ser Phe Glu Asp Met Lys Lys Val Val Cys Val Asp Gln Gln Thr Pro
            435                 440                 445

ACC ATC CCT AAC CGG CTG GCT GCA GAT CCG GTC CTC TCC GGG CTG GCC        1632
Thr Ile Pro Asn Arg Leu Ala Ala Asp Pro Val Leu Ser Gly Leu Ala
        450                 455                 460

CAG ATG ATG AGA GAG TGC TGG TAC CCC AAC CCC TCT GCT CGC CTC ACC        1680
Gln Met Met Arg Glu Cys Trp Tyr Pro Asn Pro Ser Ala Arg Leu Thr
465                 470                 475                 480

GCA CTG CGC ATA AAG AAG ACA TTG CAG AAG CTC AGT CAC AAT CCA GAG        1728
Ala Leu Arg Ile Lys Lys Thr Leu Gln Lys Leu Ser His Asn Pro Glu
                    485                 490                 495

AAG CCC AAA GTG ATT CAC TAGCCCAGGG CCACCAGGCT TCCTCTGCCT              1776
Lys Pro Lys Val Ile His
                500

AAAGTGTGTG CTGGGGAAGA AGACATAGCC TGTCTGGGTA GAGGGAGTGA AGAGAGTGTG      1836

CACGCTGCCC TGTGTGTGCC TGCTCAGCTT GCTCCCAGCC CATCCAGCCA AAATACAGC       1896

TGAGCTGAAA TTCAAAAAAA AAAAAA                                            1922

(2) INFORMATION FOR SEQ ID NO: 12:
```

```
    (i) SEQUENCE CHARACTERISTICS:
         (A) LENGTH: 502 amino acids
         (B) TYPE: amino acid
         (D) TOPOLOGY: linear (ii) MOLECULE TYPE: protein (xi) SEQUENCE DESCRIPTION: SEQ ID NO: 12:

Met Thr Leu Gly Ser Phe Arg Arg Gly Leu Leu Met Leu Ser Val Ala
  1               5                  10                  15

Leu Gly Leu Thr Gln Gly Arg Leu Ala Lys Pro Ser Lys Leu Val Asn
             20                  25                  30

Cys Thr Cys Glu Ser Pro His Cys Lys Arg Pro Phe Cys Gln Gly Ser
         35                  40                  45

Trp Cys Thr Val Val Leu Val Arg Glu Gln Gly Arg His Pro Gln Val
     50                  55                  60

Tyr Arg Gly Cys Gly Ser Leu Asn Gln Glu Leu Cys Leu Gly Arg Pro
 65                  70                  75                  80

Thr Glu Phe Leu Asn His His Cys Cys Tyr Arg Ser Phe Cys Asn His
                 85                  90                  95

Asn Val Ser Leu Met Leu Glu Ala Thr Gln Thr Pro Ser Glu Glu Pro
            100                 105                 110

Glu Val Asp Ala His Leu Pro Leu Ile Leu Gly Pro Val Leu Ala Leu
        115                 120                 125

Pro Val Leu Val Ala Leu Gly Ala Leu Gly Leu Trp Arg Val Arg Arg
130                 135                 140

Arg Gln Glu Lys Gln Arg Asp Leu His Ser Leu Gly Glu Ser Ser
145                 150                 155                 160

Leu Ile Leu Lys Ala Ser Glu Gln Ala Asp Ser Met Leu Gly Asp Phe
                165                 170                 175

Leu Asp Ser Asp Cys Thr Thr Gly Ser Gly Ser Gly Leu Pro Phe Leu
            180                 185                 190

Val Gln Arg Thr Val Ala Arg Gln Val Ala Leu Val Glu Cys Val Gly
        195                 200                 205

Lys Gly Arg Tyr Gly Glu Val Trp Arg Gly Ser Trp His Gly Glu Ser
210                 215                 220

Val Ala Val Lys Ile Phe Ser Ser Arg Asp Glu Gln Ser Trp Phe Arg
225                 230                 235                 240

Glu Thr Glu Ile Tyr Asn Thr Val Leu Leu Arg His Asp Asn Ile Leu
                245                 250                 255

Gly Phe Ile Ala Ser Asp Met Thr Ser Arg Asn Ser Ser Thr Gln Leu
            260                 265                 270

Trp Leu Ile Thr His Tyr His Glu His Gly Ser Leu Tyr Asp Phe Leu
        275                 280                 285

Gln Arg Gln Thr Leu Glu Pro Gln Leu Ala Leu Arg Leu Ala Val Ser
290                 295                 300

Pro Ala Cys Gly Leu Ala His Leu His Val Glu Ile Phe Gly Thr Gln
305                 310                 315                 320

Gly Lys Pro Ala Ile Ala His Arg Asp Leu Lys Ser Arg Asn Val Leu
                325                 330                 335

Val Lys Ser Asn Leu Gln Cys Cys Ile Ala Asp Leu Gly Leu Ala Val
            340                 345                 350

Met His Ser Gln Ser Asn Glu Tyr Leu Asp Ile Gly Asn Thr Pro Arg
        355                 360                 365

Val Gly Thr Lys Arg Tyr Met Ala Pro Glu Val Leu Asp Glu His Ile
370                 375                 380
```

```
Arg Thr Asp Cys Phe Glu Ser Tyr Lys Trp Thr Asp Ile Trp Ala Phe
385                 390                 395                 400

Gly Leu Val Leu Trp Glu Ile Ala Arg Arg Thr Ile Ile Asn Gly Ile
                405                 410                 415

Val Glu Asp Tyr Arg Pro Pro Phe Tyr Asp Met Val Pro Asn Asp Pro
            420                 425                 430

Ser Phe Glu Asp Met Lys Lys Val Val Cys Val Asp Gln Gln Thr Pro
        435                 440                 445

Thr Ile Pro Asn Arg Leu Ala Ala Asp Pro Val Leu Ser Gly Leu Ala
    450                 455                 460

Gln Met Met Arg Glu Cys Trp Tyr Pro Asn Pro Ser Ala Arg Leu Thr
465                 470                 475                 480

Ala Leu Arg Ile Lys Lys Thr Leu Gln Lys Leu Ser His Asn Pro Glu
                485                 490                 495

Lys Pro Lys Val Ile His
            500

(2) INFORMATION FOR SEQ ID NO: 13:

(i) SEQUENCE CHARACTERISTICS:
        (A) LENGTH: 2070 base pairs
        (B) TYPE: nucleic acid
        (C) STRANDEDNESS: unknown
        (D) TOPOLOGY: linear (ii) MOLECULE TYPE: cDNA (iii) HYPOTHETICAL: NO (iv) ANTI-SENSE: NO (v) FRAGMENT TYPE: internal (vi) ORIGINAL SOURCE:
        (A) ORGANISM: Mouse (ix) FEATURE:
        (A) NAME/KEY: CDS
        (B) LOCATION: 217..1812

(xi) SEQUENCE DESCRIPTION: SEQ ID NO: 13:

ATTCATGAGA TGGAAGCATA GGTCAAAGCT GTTCGGAGAA ATTGGAACTA CAGTTTTATC      60

TAGCCACATC TCTGAGAATT CTGAAGAAAG CAGCAGGTGA AAGTCATTGC CAAGTGATTT    120

TGTTCTGTAA GGAAGCCTCC CTCATTCACT TACACCAGTG AGACAGCAGG ACCAGTCATT    180

CAAAGGGCCG TGTACAGGAC GCGTGGCAAT CAGACA ATG ACT CAG CTA TAC ACT      234
                                        Met Thr Gln Leu Tyr Thr
                                          1               5

TAC ATC AGA TTA CTG GGA GCC TGT CTG TTC ATC ATT TCT CAT GTT CAA      282
Tyr Ile Arg Leu Leu Gly Ala Cys Leu Phe Ile Ile Ser His Val Gln
         10                  15                  20

GGG CAG AAT CTA GAT AGT ATG CTC CAT GGC ACT GGT ATG AAA TCA GAC      330
Gly Gln Asn Leu Asp Ser Met Leu His Gly Thr Gly Met Lys Ser Asp
     25                  30                  35

TTG GAC CAG AAG AAG CCA GAA AAT GGA GTG ACT TTA GCA CCA GAG GAT      378
Leu Asp Gln Lys Lys Pro Glu Asn Gly Val Thr Leu Ala Pro Glu Asp
 40                  45                  50

ACC TTG CCT TTC TTA AAG TGT TAT TGC TCA GGA CAC TGC CCA GAT GAT      426
Thr Leu Pro Phe Leu Lys Cys Tyr Cys Ser Gly His Cys Pro Asp Asp
55                   60                  65                  70

GCT ATT AAT AAC ACA TGC ATA ACT AAT GGC CAT TGC TTT GCC ATT ATA      474
Ala Ile Asn Asn Thr Cys Ile Thr Asn Gly His Cys Phe Ala Ile Ile
                 75                  80                  85
```

-continued

| | |
|---|---|
| GAA GAA GAT GAT CAG GGA GAA ACC ACA TTA ACT TCT GGG TGT ATG AAG<br>Glu Glu Asp Asp Gln Gly Glu Thr Thr Leu Thr Ser Gly Cys Met Lys<br>              90                    95                   100 | 522 |
| TAT GAA GGC TCT GAT TTT CAA TGC AAG GAT TCA CCG AAA GCC CAG CTA<br>Tyr Glu Gly Ser Asp Phe Gln Cys Lys Asp Ser Pro Lys Ala Gln Leu<br>     105                    110                   115 | 570 |
| CGC AGG ACA ATA GAA TGT TGT CGG ACC AAT TTG TGC AAC CAG TAT TTG<br>Arg Arg Thr Ile Glu Cys Cys Arg Thr Asn Leu Cys Asn Gln Tyr Leu<br>120                    125                   130 | 618 |
| CAG CCT ACA CTG CCC CCT GTT GTT ATA GGT CCG TTC TTT GAT GGC AGC<br>Gln Pro Thr Leu Pro Pro Val Val Ile Gly Pro Phe Phe Asp Gly Ser<br>135                    140                   145                   150 | 666 |
| ATC CGA TGG CTG GTT GTG CTC ATT TCC ATG GCT GTC TGT ATA GTT GCT<br>Ile Arg Trp Leu Val Val Leu Ile Ser Met Ala Val Cys Ile Val Ala<br>              155                   160                   165 | 714 |
| ATG ATC ATC TTC TCC AGC TGC TTT TGC TAT AAG CAT TAT TGT AAG AGT<br>Met Ile Ile Phe Ser Ser Cys Phe Cys Tyr Lys His Tyr Cys Lys Ser<br>                170                   175                   180 | 762 |
| ATC TCA AGC AGG GGT CGT TAC AAC CGT GAT TTG GAA CAG GAT GAA GCA<br>Ile Ser Ser Arg Gly Arg Tyr Asn Arg Asp Leu Glu Gln Asp Glu Ala<br>            185                   190                   195 | 810 |
| TTT ATT CCA GTA GGA GAA TCA TTG AAA GAC CTG ATT GAC CAG TCC CAA<br>Phe Ile Pro Val Gly Glu Ser Leu Lys Asp Leu Ile Asp Gln Ser Gln<br>200                    205                   210 | 858 |
| AGC TCT GGG AGT GGA TCT GGA TTG CCT TTA TTG GTT CAG CGA ACT ATT<br>Ser Ser Gly Ser Gly Ser Gly Leu Pro Leu Leu Val Gln Arg Thr Ile<br>215                    220                   225                   230 | 906 |
| GCC AAA CAG ATT CAG ATG GTT CGG CAG GTT GGT AAA GGC CGC TAT GGA<br>Ala Lys Gln Ile Gln Met Val Arg Gln Val Gly Lys Gly Arg Tyr Gly<br>                235                   240                   245 | 954 |
| GAA GTA TGG ATG GGT AAA TGG CGT GGT GAA AAA GTG GCT GTC AAA GTG<br>Glu Val Trp Met Gly Lys Trp Arg Gly Glu Lys Val Ala Val Lys Val<br>                250                   255                   260 | 1002 |
| TTT TTT ACC ACT GAA GAA GCT AGC TGG TTT AGA GAA ACA GAA ATC TAC<br>Phe Phe Thr Thr Glu Glu Ala Ser Trp Phe Arg Glu Thr Glu Ile Tyr<br>     265                    270                   275 | 1050 |
| CAG ACG GTG TTA ATG CGT CAT GAA AAT ATA CTT GGT TTT ATA GCT GCA<br>Gln Thr Val Leu Met Arg His Glu Asn Ile Leu Gly Phe Ile Ala Ala<br>280                    285                   290 | 1098 |
| GAC ATT AAA GGC ACT GGT TCC TGG ACT CAG CTG TAT TTG ATT ACT GAT<br>Asp Ile Lys Gly Thr Gly Ser Trp Thr Gln Leu Tyr Leu Ile Thr Asp<br>295                    300                   305                   310 | 1146 |
| TAC CAT GAA AAT GGA TCT CTC TAT GAC TTC CTG AAA TGT GCC ACA CTA<br>Tyr His Glu Asn Gly Ser Leu Tyr Asp Phe Leu Lys Cys Ala Thr Leu<br>              315                   320                   325 | 1194 |
| GAC ACC AGA GCC CTA CTC AAG TTA GCT TAT TCT GCT GCT TGT GGT CTG<br>Asp Thr Arg Ala Leu Leu Lys Leu Ala Tyr Ser Ala Ala Cys Gly Leu<br>            330                   335                   340 | 1242 |
| TGC CAC CTC CAC ACA GAA ATT TAT GGT ACC CAA GGG AAG CCT GCA ATT<br>Cys His Leu His Thr Glu Ile Tyr Gly Thr Gln Gly Lys Pro Ala Ile<br>              345                   350                   355 | 1290 |
| GCT CAT CGA GAC CTG AAG AGC AAA AAC ATC CTT ATT AAG AAA AAT GGA<br>Ala His Arg Asp Leu Lys Ser Lys Asn Ile Leu Ile Lys Lys Asn Gly<br>360                    365                   370 | 1338 |
| AGT TGC TGT ATT GCT GAC CTG GGC CTA GCT GTT AAA TTC AAC AGT GAT<br>Ser Cys Cys Ile Ala Asp Leu Gly Leu Ala Val Lys Phe Asn Ser Asp<br>375                    380                   385                   390 | 1386 |
| ACA AAT GAA GTT GAC ATA CCC TTG AAT ACC AGG GTG GGC ACC AAG CGG<br>Thr Asn Glu Val Asp Ile Pro Leu Asn Thr Arg Val Gly Thr Lys Arg<br>              395                   400                   405 | 1434 |

```
TAC ATG GCT CCA GAA GTG CTG GAT GAA AGC CTG AAT AAA AAC CAT TTC      1482
Tyr Met Ala Pro Glu Val Leu Asp Glu Ser Leu Asn Lys Asn His Phe
        410                 415                 420

CAG CCC TAC ATC ATG GCT GAC ATC TAT AGC TTT GGT TTG ATC ATT TGG      1530
Gln Pro Tyr Ile Met Ala Asp Ile Tyr Ser Phe Gly Leu Ile Ile Trp
                425                 430                 435

GAA ATG GCT CGT CGT TGT ATT ACA GGA GGA ATC GTG GAG GAA TAT CAA      1578
Glu Met Ala Arg Arg Cys Ile Thr Gly Gly Ile Val Glu Glu Tyr Gln
440                 445                 450

TTA CCA TAT TAC AAC ATG GTG CCC AGT GAC CCA TCC TAT GAG GAC ATG      1626
Leu Pro Tyr Tyr Asn Met Val Pro Ser Asp Pro Ser Tyr Glu Asp Met
455                 460                 465                 470

CGT GAG GTT GTG TGT GTG AAA CGC TTG CGG CCA ATC GTG TCT AAC CGC      1674
Arg Glu Val Val Cys Val Lys Arg Leu Arg Pro Ile Val Ser Asn Arg
                475                 480                 485

TGG AAC AGC GAT GAA TGT CTT CGA GCA GTT TTG AAG CTA ATG TCA GAA      1722
Trp Asn Ser Asp Glu Cys Leu Arg Ala Val Leu Lys Leu Met Ser Glu
                490                 495                 500

TGT TGG GCC CAT AAT CCA GCC TCC AGA CTC ACA GCT TTG AGA ATC AAG      1770
Cys Trp Ala His Asn Pro Ala Ser Arg Leu Thr Ala Leu Arg Ile Lys
        505                 510                 515

AAG ACA CTT GCA AAA ATG GTT GAA TCC CAG GAT GTA AAG ATT              1812
Lys Thr Leu Ala Lys Met Val Glu Ser Gln Asp Val Lys Ile
                520                 525                 530

TGACAATTAA ACAATTTTGA GGGAGAATTT AGACTGCAAG AACTTCTTCA CCCAAGGAAT    1872

GGGTGGGATT AGCATGGAAT AGGATGTTGA CTTGGTTTCC AGACTCCTTC CTCTACATCT    1932

TCACAGGCTG CTAACAGTAA ACCTTACCGT ACTCTACAGA ATACAAGATT GGAACTTGGA    1992

ACTTCAAACA TGTCATTCTT TATATATGAC AGCTTTGTTT AATGTGGGG TTTTTTTGTT     2052

TGCTTTTTTT GTTTTGTT                                                  2070

(2) INFORMATION FOR SEQ ID NO: 14:

(i) SEQUENCE CHARACTERISTICS:
        (A) LENGTH: 532 amino acids
        (B) TYPE: amino acid
        (D) TOPOLOGY: linear (ii) MOLECULE TYPE: protein (xi) SEQUENCE DESCRIPTION: SEQ ID NO: 14:

Met Thr Gln Leu Tyr Thr Tyr Ile Arg Leu Leu Gly Ala Cys Leu Phe
 1               5                  10                  15

Ile Ile Ser His Val Gln Gly Gln Asn Leu Asp Ser Met Leu His Gly
                20                  25                  30

Thr Gly Met Lys Ser Asp Leu Asp Gln Lys Lys Pro Glu Asn Gly Val
            35                  40                  45

Thr Leu Ala Pro Glu Asp Thr Leu Pro Phe Leu Lys Cys Tyr Cys Ser
        50                  55                  60

Gly His Cys Pro Asp Asp Ala Ile Asn Asn Thr Cys Ile Thr Asn Gly
65                  70                  75                  80

His Cys Phe Ala Ile Ile Glu Glu Asp Asp Gln Gly Glu Thr Thr Leu
                85                  90                  95

Thr Ser Gly Cys Met Lys Tyr Glu Gly Ser Asp Phe Gln Cys Lys Asp
            100                 105                 110

Ser Pro Lys Ala Gln Leu Arg Arg Thr Ile Glu Cys Cys Arg Thr Asn
        115                 120                 125

Leu Cys Asn Gln Tyr Leu Gln Pro Thr Leu Pro Pro Val Val Ile Gly
```

```
            130                 135                 140
Pro Phe Phe Asp Gly Ser Ile Arg Trp Leu Val Leu Ile Ser Met
145                 150                 155                 160

Ala Val Cys Ile Val Ala Met Ile Ile Phe Ser Ser Cys Phe Cys Tyr
                165                 170                 175

Lys His Tyr Cys Lys Ser Ile Ser Ser Arg Gly Arg Tyr Asn Arg Asp
                180                 185                 190

Leu Glu Gln Asp Glu Ala Phe Ile Pro Val Gly Glu Ser Leu Lys Asp
                195                 200                 205

Leu Ile Asp Gln Ser Gln Ser Ser Gly Ser Gly Ser Gly Leu Pro Leu
210                 215                 220

Leu Val Gln Arg Thr Ile Ala Lys Gln Ile Gln Met Val Arg Gln Val
225                 230                 235                 240

Gly Lys Gly Arg Tyr Gly Glu Val Trp Met Gly Lys Trp Arg Gly Glu
                245                 250                 255

Lys Val Ala Val Lys Val Phe Phe Thr Thr Glu Glu Ala Ser Trp Phe
                260                 265                 270

Arg Glu Thr Glu Ile Tyr Gln Thr Val Leu Met Arg His Glu Asn Ile
                275                 280                 285

Leu Gly Phe Ile Ala Ala Asp Ile Lys Gly Thr Gly Ser Trp Thr Gln
                290                 295                 300

Leu Tyr Leu Ile Thr Asp Tyr His Glu Asn Gly Ser Leu Tyr Asp Phe
305                 310                 315                 320

Leu Lys Cys Ala Thr Leu Asp Thr Arg Ala Leu Leu Lys Leu Ala Tyr
                325                 330                 335

Ser Ala Ala Cys Gly Leu Cys His Leu His Thr Glu Ile Tyr Gly Thr
                340                 345                 350

Gln Gly Lys Pro Ala Ile Ala His Arg Asp Leu Lys Ser Lys Asn Ile
                355                 360                 365

Leu Ile Lys Lys Asn Gly Ser Cys Cys Ile Ala Asp Leu Gly Leu Ala
                370                 375                 380

Val Lys Phe Asn Ser Asp Thr Asn Glu Val Asp Ile Pro Leu Asn Thr
385                 390                 395                 400

Arg Val Gly Thr Lys Arg Tyr Met Ala Pro Glu Val Leu Asp Glu Ser
                405                 410                 415

Leu Asn Lys Asn His Phe Gln Pro Tyr Ile Met Ala Asp Ile Tyr Ser
                420                 425                 430

Phe Gly Leu Ile Ile Trp Glu Met Ala Arg Arg Cys Ile Thr Gly Gly
                435                 440                 445

Ile Val Glu Glu Tyr Gln Leu Pro Tyr Tyr Asn Met Val Pro Ser Asp
450                 455                 460

Pro Ser Tyr Glu Asp Met Arg Glu Val Val Cys Val Lys Arg Leu Arg
465                 470                 475                 480

Pro Ile Val Ser Asn Arg Trp Asn Ser Asp Glu Cys Leu Arg Ala Val
                485                 490                 495

Leu Lys Leu Met Ser Glu Cys Trp Ala His Asn Pro Ala Ser Arg Leu
                500                 505                 510

Thr Ala Leu Arg Ile Lys Lys Thr Leu Ala Lys Met Val Glu Ser Gln
                515                 520                 525

Asp Val Lys Ile
                530

(2) INFORMATION FOR SEQ ID NO: 15:
```

(i) SEQUENCE CHARACTERISTICS:
    (A) LENGTH: 2160 base pairs
    (B) TYPE: nucleic acid
    (C) STRANDEDNESS: unknown
    (D) TOPOLOGY: linear (ii) MOLECULE TYPE: cDNA (iii) HYPOTHETICAL: NO (iv) ANTI-SENSE: NO (v) FRAGMENT TYPE: internal (vi) ORIGINAL SOURCE:
    (A) ORGANISM: Mouse (ix) FEATURE:
    (A) NAME/KEY: CDS
    (B) LOCATION: 10..1524

(xi) SEQUENCE DESCRIPTION: SEQ ID NO: 15:

```
CGCGGTTAC ATG GCG GAG TCG GCC GGA GCC TCC TCC TTC TTC CCC CTT            48
          Met Ala Glu Ser Ala Gly Ala Ser Ser Phe Phe Pro Leu
            1               5                  10

GTT GTC CTC CTG CTC GCC GGC AGC GGC GGG TCC GGG CCC CGG GGG ATC          96
Val Val Leu Leu Leu Ala Gly Ser Gly Gly Ser Gly Pro Arg Gly Ile
     15                  20                  25

CAG GCT CTG CTG TGT GCG TGC ACC AGC TGC CTA CAG ACC AAC TAC ACC          144
Gln Ala Leu Leu Cys Ala Cys Thr Ser Cys Leu Gln Thr Asn Tyr Thr
 30                  35                  40                  45

TGT GAG ACA GAT GGG GCT TGC ATG GTC TCC ATC TTT AAC CTG GAT GGC          192
Cys Glu Thr Asp Gly Ala Cys Met Val Ser Ile Phe Asn Leu Asp Gly
                 50                  55                  60

GTG GAG CAC CAT GTA CGT ACC TGC ATC CCC AAG GTG GAG CTG GTT CCT          240
Val Glu His His Val Arg Thr Cys Ile Pro Lys Val Glu Leu Val Pro
             65                  70                  75

GCT GGA AAG CCC TTC TAC TGC CTG AGT TCA GAG GAT CTG CGC AAC ACA          288
Ala Gly Lys Pro Phe Tyr Cys Leu Ser Ser Glu Asp Leu Arg Asn Thr
         80                  85                  90

CAC TGC TGC TAT ATT GAC TTC TGC AAC AAG ATT GAC CTC AGG GTC CCC          336
His Cys Cys Tyr Ile Asp Phe Cys Asn Lys Ile Asp Leu Arg Val Pro
     95                  100                 105

AGC GGA CAC CTC AAG GAG CCT GCG CAC CCC TCC ATG TGG GGC CCT GTG          384
Ser Gly His Leu Lys Glu Pro Ala His Pro Ser Met Trp Gly Pro Val
110                  115                 120                 125

GAG CTG GTC GGC ATC ATC GCC GGC CCC GTC TTC CTC CTC TTC CTT ATC          432
Glu Leu Val Gly Ile Ile Ala Gly Pro Val Phe Leu Leu Phe Leu Ile
                 130                 135                 140

ATT ATC ATC GTC TTC CTG GTC ATC AAC TAT CAC CAG CGT GTC TAC CAT          480
Ile Ile Ile Val Phe Leu Val Ile Asn Tyr His Gln Arg Val Tyr His
             145                 150                 155

AAC CGC CAG AGG TTG GAC ATG GAG GAC CCC TCT TGC GAG ATG TGT CTC          528
Asn Arg Gln Arg Leu Asp Met Glu Asp Pro Ser Cys Glu Met Cys Leu
         160                 165                 170

TCC AAA GAC AAG ACG CTC CAG GAT CTC GTC TAC GAC CTC TCC ACG TCA          576
Ser Lys Asp Lys Thr Leu Gln Asp Leu Val Tyr Asp Leu Ser Thr Ser
175                  180                 185

GGG TCT GGC TCA GGG TTA CCC CTT TTT GTC CAG CGC ACA GTG GCC CGA          624
Gly Ser Gly Ser Gly Leu Pro Leu Phe Val Gln Arg Thr Val Ala Arg
190                  195                 200                 205

ACC ATT GTT TTA CAA GAG ATT ATC GGC AAG GGC CGG TTC GGG GAA GTA          672
Thr Ile Val Leu Gln Glu Ile Ile Gly Lys Gly Arg Phe Gly Glu Val
                 210                 215                 220

TGG CGT GGT CGC TGG AGG GGT GGT GAC GTG GCT GTG AAA ATC TTC TCT          720
```

-continued

```
            Trp Arg Gly Arg Trp Arg Gly Gly Asp Val Ala Val Lys Ile Phe Ser
                    225                 230                 235
TCT CGT GAA GAA CGG TCT TGG TTC CGT GAA GCA GAG ATC TAC CAG ACC             768
Ser Arg Glu Glu Arg Ser Trp Phe Arg Glu Ala Glu Ile Tyr Gln Thr
        240                 245                 250

GTC ATG CTG CGC CAT GAA AAC ATC CTT GGC TTT ATT GCT GCT GAC AAT             816
Val Met Leu Arg His Glu Asn Ile Leu Gly Phe Ile Ala Ala Asp Asn
        255                 260                 265

AAA GAT AAT GGC ACC TGG ACC CAG CTG TGG CTT GTC TCT GAC TAT CAC             864
Lys Asp Asn Gly Thr Trp Thr Gln Leu Trp Leu Val Ser Asp Tyr His
270                 275                 280                 285

GAG CAT GGC TCA CTG TTT GAT TAT CTG AAC CGC TAC ACA GTG ACC ATT             912
Glu His Gly Ser Leu Phe Asp Tyr Leu Asn Arg Tyr Thr Val Thr Ile
                290                 295                 300

GAG GGA ATG ATT AAG CTA GCC TTG TCT GCA GCC AGT GGT TTG GCA CAC             960
Glu Gly Met Ile Lys Leu Ala Leu Ser Ala Ala Ser Gly Leu Ala His
            305                 310                 315

CTG CAT ATG GAG ATT GTG GGC ACT CAA GGG AAG CCG GGA ATT GCT CAT            1008
Leu His Met Glu Ile Val Gly Thr Gln Gly Lys Pro Gly Ile Ala His
        320                 325                 330

CGA GAC TTG AAG TCA AAG AAC ATC CTG GTG AAA AAA AAT GGC ATG TGT            1056
Arg Asp Leu Lys Ser Lys Asn Ile Leu Val Lys Lys Asn Gly Met Cys
335                 340                 345

GCC ATT GCA GAC CTG GGC CTG GCT GTC CGT CAT GAT GCG GTC ACT GAC            1104
Ala Ile Ala Asp Leu Gly Leu Ala Val Arg His Asp Ala Val Thr Asp
350                 355                 360                 365

ACC ATA GAC ATT GCT CCA AAT CAG AGG GTG GGG ACC AAA CGA TAC ATG            1152
Thr Ile Asp Ile Ala Pro Asn Gln Arg Val Gly Thr Lys Arg Tyr Met
                370                 375                 380

GCT CCT GAA GTC CTT GAC GAG ACA ATC AAC ATG AAG CAC TTT GAC TCC            1200
Ala Pro Glu Val Leu Asp Glu Thr Ile Asn Met Lys His Phe Asp Ser
            385                 390                 395

TTC AAA TGT GCC GAC ATC TAT GCC CTC GGG CTT GTC TAC TGG GAG ATT            1248
Phe Lys Cys Ala Asp Ile Tyr Ala Leu Gly Leu Val Tyr Trp Glu Ile
        400                 405                 410

GCA CGA AGA TGC AAT TCT GGA GGA GTC CAT GAA GAC TAT CAA CTG CCG            1296
Ala Arg Arg Cys Asn Ser Gly Gly Val His Glu Asp Tyr Gln Leu Pro
    415                 420                 425

TAT TAC GAC TTA GTG CCC TCC GAC CCT TCC ATT GAG GAG ATG CGA AAG            1344
Tyr Tyr Asp Leu Val Pro Ser Asp Pro Ser Ile Glu Glu Met Arg Lys
430                 435                 440                 445

GTT GTA TGT GAC CAG AAG CTA CGG CCC AAT GTC CCC AAC TGG TGG CAG            1392
Val Val Cys Asp Gln Lys Leu Arg Pro Asn Val Pro Asn Trp Trp Gln
                450                 455                 460

AGT TAT GAG GCC TTG CGA GTG ATG GGA AAG ATG ATG CGG GAG TGC TGG            1440
Ser Tyr Glu Ala Leu Arg Val Met Gly Lys Met Met Arg Glu Cys Trp
            465                 470                 475

TAC GCC AAT GGT GCT GCC CGT CTG ACA GCT CTG CGC ATC AAG AAG ACT            1488
Tyr Ala Asn Gly Ala Ala Arg Leu Thr Ala Leu Arg Ile Lys Lys Thr
        480                 485                 490

CTG TCC CAG CTA AGC GTG CAG GAA GAT GTG AAG ATT TAAGCTGTTC                 1534
Leu Ser Gln Leu Ser Val Gln Glu Asp Val Lys Ile
    495                 500                 505

CTCTGCCTAC ACAAAGAACC TGGGCAGTGA GGATGACTGC AGCCACCGTG CAAGCGTCGT          1594

GGAGGCCTAT CCTCTTGTTT CTGCCCGGCC CTCTGGCAGA GCCCTGGCCT GCAAGAGGGA          1654

CAGAGCCTGG GAGACGCGCG CACTCCCGTT GGGTTTGAGA CAGACACTTT TTATATTTAC          1714

CTCCTGATGG CATGGAGACC TGAGCAAATC ATGTAGTCAC TCAATGCCAC AACTCAAACT          1774

GCTTCAGTGG GAAGTACAGA GACCCAGTGC ATTGCGTGTG CAGGAGCGTG AGGTGCTGGG          1834
```

```
CTCGCCAGGA GCGGCCCCCA TACCTTGTGG TCCACTGGGC TGCAGGTTTT CCTCCAGGGA    1894

CCAGTCAACT GGCATCAAGA TATTGAGAGG AACCGGAAGT TTCTCCCTCC TTCCCGTAGC    1954

AGTCCTGAGC CACACCATCC TTCTCATGGA CATCCGGAGG ACTGCCCCTA GAGACACAAC    2014

CTGCTGCCTG TCTGTCCAGC CAAGTGCGCA TGTGCCGAGG TGTGTCCCAC ATTGTGCCTG    2074

GTCTGTGCCA CGCCCGTGTG TGTGTGTGTG TGTGTGAGTG AGTGTGTGTG TGTACACTTA    2134

ACCTGCTTGA GCTTCTGTGC ATGTGT                                         2160
```

(2) INFORMATION FOR SEQ ID NO: 16:

(i) SEQUENCE CHARACTERISTICS:
        (A) LENGTH: 505 amino acids
        (B) TYPE: amino acid
        (D) TOPOLOGY: linear (ii) MOLECULE TYPE: protein (xi) SEQUENCE DESCRIPTION: SEQ ID NO: 16:

```
Met Ala Glu Ser Ala Gly Ala Ser Ser Phe Phe Pro Leu Val Val Leu
 1               5                  10                  15

Leu Leu Ala Gly Ser Gly Gly Ser Gly Pro Arg Gly Ile Gln Ala Leu
             20                  25                  30

Leu Cys Ala Cys Thr Ser Cys Leu Gln Thr Asn Tyr Thr Cys Glu Thr
         35                  40                  45

Asp Gly Ala Cys Met Val Ser Ile Phe Asn Leu Asp Gly Val Glu His
     50                  55                  60

His Val Arg Thr Cys Ile Pro Lys Val Glu Leu Val Pro Ala Gly Lys
 65                  70                  75                  80

Pro Phe Tyr Cys Leu Ser Ser Glu Asp Leu Arg Asn Thr His Cys Cys
                 85                  90                  95

Tyr Ile Asp Phe Cys Asn Lys Ile Asp Leu Arg Val Pro Ser Gly His
            100                 105                 110

Leu Lys Glu Pro Ala His Pro Ser Met Trp Gly Pro Val Glu Leu Val
        115                 120                 125

Gly Ile Ile Ala Gly Pro Val Phe Leu Leu Phe Leu Ile Ile Ile Ile
    130                 135                 140

Val Phe Leu Val Ile Asn Tyr His Gln Arg Val Tyr His Asn Arg Gln
145                 150                 155                 160

Arg Leu Asp Met Glu Asp Pro Ser Cys Glu Met Cys Leu Ser Lys Asp
                165                 170                 175

Lys Thr Leu Gln Asp Leu Val Tyr Asp Leu Ser Thr Ser Gly Ser Gly
            180                 185                 190

Ser Gly Leu Pro Leu Phe Val Gln Arg Thr Val Ala Arg Thr Ile Val
        195                 200                 205

Leu Gln Glu Ile Ile Gly Lys Gly Arg Phe Gly Glu Val Trp Arg Gly
    210                 215                 220

Arg Trp Arg Gly Gly Asp Val Ala Val Lys Ile Phe Ser Ser Arg Glu
225                 230                 235                 240

Glu Arg Ser Trp Phe Arg Glu Ala Glu Ile Tyr Gln Thr Val Met Leu
                245                 250                 255

Arg His Glu Asn Ile Leu Gly Phe Ile Ala Ala Asp Asn Lys Asp Asn
            260                 265                 270

Gly Thr Trp Thr Gln Leu Trp Leu Val Ser Asp Tyr His Glu His Gly
        275                 280                 285

Ser Leu Phe Asp Tyr Leu Asn Arg Tyr Thr Val Thr Ile Glu Gly Met
```

-continued

```
                290                 295                 300
Ile Lys Leu Ala Leu Ser Ala Ala Ser Gly Leu Ala His Leu His Met
305                 310                 315                 320

Glu Ile Val Gly Thr Gln Gly Lys Pro Gly Ile Ala His Arg Asp Leu
                325                 330                 335

Lys Ser Lys Asn Ile Leu Val Lys Lys Asn Gly Met Cys Ala Ile Ala
                340                 345                 350

Asp Leu Gly Leu Ala Val Arg His Asp Ala Val Thr Asp Thr Ile Asp
                355                 360                 365

Ile Ala Pro Asn Gln Arg Val Gly Thr Lys Arg Tyr Met Ala Pro Glu
                370                 375                 380

Val Leu Asp Glu Thr Ile Asn Met Lys His Phe Asp Ser Phe Lys Cys
385                 390                 395                 400

Ala Asp Ile Tyr Ala Leu Gly Leu Val Tyr Trp Glu Ile Ala Arg Arg
                405                 410                 415

Cys Asn Ser Gly Gly Val His Glu Asp Tyr Gln Leu Pro Tyr Tyr Asp
                420                 425                 430

Leu Val Pro Ser Asp Pro Ser Ile Glu Glu Met Arg Lys Val Val Cys
                435                 440                 445

Asp Gln Lys Leu Arg Pro Asn Val Pro Asn Trp Trp Gln Ser Tyr Glu
                450                 455                 460

Ala Leu Arg Val Met Gly Lys Met Met Arg Glu Cys Trp Tyr Ala Asn
465                 470                 475                 480

Gly Ala Ala Arg Leu Thr Ala Leu Arg Ile Lys Lys Thr Leu Ser Gln
                485                 490                 495

Leu Ser Val Gln Glu Asp Val Lys Ile
                500                 505
```

(2) INFORMATION FOR SEQ ID NO: 17:

(i) SEQUENCE CHARACTERISTICS:
        (A) LENGTH: 1952 base pairs
        (B) TYPE: nucleic acid
        (C) STRANDEDNESS: unknown
        (D) TOPOLOGY: unknown (ii) MOLECULE TYPE: cDNA (iii) HYPOTHETICAL: NO (iv) ANTI-SENSE: NO (v) FRAGMENT TYPE: internal (vi) ORIGINAL SOURCE:
        (A) ORGANISM: Mouse (ix) FEATURE:
        (A) NAME/KEY: CDS
        (B) LOCATION: 187..1692

(xi) SEQUENCE DESCRIPTION: SEQ ID NO: 17:

```
AAGCGGCGGC AGAAGTTGCC GGCGTGGTGC TCGTAGTGAG GGCGCGGAGG ACCCGGGACC      60

TGGGAAGCGG CGGCGGGTTA ACTTCGGCTG AATCACAACC ATTTGGCGCT GAGCTATGAC     120

AAGAGAGCAA ACAAAAAGTT AAGGAGCAA CCCGGCCATA AGTGAAGAGA GAAGTTTATT     180

GATAAC ATG CTC TTA CGA AGC TCT GGA AAA TTA AAT GTG GGC ACC AAG       228
       Met Leu Leu Arg Ser Ser Gly Lys Leu Asn Val Gly Thr Lys
         1               5                  10

AAG GAG GAT GGA GAG AGT ACA GCC CCC ACC CCT CGG CCC AAG ATC CTA      276
Lys Glu Asp Gly Glu Ser Thr Ala Pro Thr Pro Arg Pro Lys Ile Leu
 15                  20                  25                  30
```

-continued

| | | |
|---|---|---|
| CGT TGT AAA TGC CAC CAC CAC TGT CCG GAA GAC TCA GTC AAC AAT ATC<br>Arg Cys Lys Cys His His His Cys Pro Glu Asp Ser Val Asn Asn Ile<br>                  35                  40                  45 | 324 |
| TGC AGC ACA GAT GGG TAC TGC TTC ACG ATG ATA GAA GAA GAT GAC TCT<br>Cys Ser Thr Asp Gly Tyr Cys Phe Thr Met Ile Glu Glu Asp Asp Ser<br>                  50                  55                  60 | 372 |
| GGA ATG CCT GTT GTC ACC TCT GGA TGT CTA GGA CTA GAA GGG TCA GAT<br>Gly Met Pro Val Val Thr Ser Gly Cys Leu Gly Leu Glu Gly Ser Asp<br>              65                  70                  75 | 420 |
| TTT CAA TGT CGT GAC ACT CCC ATT CCT CAT CAA AGA AGA TCA ATT GAA<br>Phe Gln Cys Arg Asp Thr Pro Ile Pro His Gln Arg Arg Ser Ile Glu<br>80                        85                  90 | 468 |
| TGC TGC ACA GAA AGG AAT GAG TGT AAT AAA GAC CTC CAC CCC ACT CTG<br>Cys Cys Thr Glu Arg Asn Glu Cys Asn Lys Asp Leu His Pro Thr Leu<br>95                   100              105              110 | 516 |
| CCT CCT CTC AAG GAC AGA GAT TTT GTT GAT GGG CCC ATA CAC CAC AAG<br>Pro Pro Leu Lys Asp Arg Asp Phe Val Asp Gly Pro Ile His His Lys<br>                115                 120              125 | 564 |
| GCC TTG CTT ATC TCT GTG ACT GTC TGT AGT TTA CTC TTG GTC CTC ATT<br>Ala Leu Leu Ile Ser Val Thr Val Cys Ser Leu Leu Leu Val Leu Ile<br>              130                 135              140 | 612 |
| ATT TTA TTC TGT TAC TTC AGG TAT AAA AGA CAA GAA GCC CGA CCT CGG<br>Ile Leu Phe Cys Tyr Phe Arg Tyr Lys Arg Gln Glu Ala Arg Pro Arg<br>                 145                 150              155 | 660 |
| TAC AGC ATT GGG CTG GAG CAG GAC GAG ACA TAC ATT CCT CCT GGA GAG<br>Tyr Ser Ile Gly Leu Glu Gln Asp Glu Thr Tyr Ile Pro Pro Gly Glu<br>         160                 165              170 | 708 |
| TCC CTG AGA GAC TTG ATC GAG CAG TCT CAG AGC TCG GGA AGT GGA TCA<br>Ser Leu Arg Asp Leu Ile Glu Gln Ser Gln Ser Ser Gly Ser Gly Ser<br>175                    180                 185              190 | 756 |
| GGC CTC CCT CTG CTG GTC CAA AGG ACA ATA GCT AAG CAA ATT CAG ATG<br>Gly Leu Pro Leu Leu Val Gln Arg Thr Ile Ala Lys Gln Ile Gln Met<br>              195                 200              205 | 804 |
| GTG AAG CAG ATT GGA AAA GGC CGC TAT GGC GAG GTG TGG ATG GGA AAG<br>Val Lys Gln Ile Gly Lys Gly Arg Tyr Gly Glu Val Trp Met Gly Lys<br>              210                 215              220 | 852 |
| TGG CGT GGA GAA AAG GTG GCT GTG AAA GTG TTC TTC ACC ACG GAG GAA<br>Trp Arg Gly Glu Lys Val Ala Val Lys Val Phe Phe Thr Thr Glu Glu<br>         225                 230              235 | 900 |
| GCC AGC TGG TTC CGA GAG ACT GAG ATA TAT CAG ACG GTC CTG ATG CGG<br>Ala Ser Trp Phe Arg Glu Thr Glu Ile Tyr Gln Thr Val Leu Met Arg<br>240                      245                 250 | 948 |
| CAT GAG AAT ATT CTG GGG TTC ATT GCT GCA GAT ATC AAA GGG ACT GGG<br>His Glu Asn Ile Leu Gly Phe Ile Ala Ala Asp Ile Lys Gly Thr Gly<br>255                      260               265              270 | 996 |
| TCC TGG ACT CAG TTG TAC CTC ATC ACA GAC TAT CAT GAA AAC GGC TCC<br>Ser Trp Thr Gln Leu Tyr Leu Ile Thr Asp Tyr His Glu Asn Gly Ser<br>              275                 280              285 | 1044 |
| CTT TAT GAC TAT CTG AAA TCC ACC ACC TTA GAC GCA AAG TCC ATG CTG<br>Leu Tyr Asp Tyr Leu Lys Ser Thr Thr Leu Asp Ala Lys Ser Met Leu<br>         290                 295              300 | 1092 |
| AAG CTA GCC TAC TCC TCT GTC AGC GGC CTA TGC CAT TTA CAC ACG GAA<br>Lys Leu Ala Tyr Ser Ser Val Ser Gly Leu Cys His Leu His Thr Glu<br>              305                 310              315 | 1140 |
| ATC TTT AGC ACT CAA GGC AAG CCA GCA ATC GCC CAT CGA GAC TTG AAA<br>Ile Phe Ser Thr Gln Gly Lys Pro Ala Ile Ala His Arg Asp Leu Lys<br>320                      325               330 | 1188 |
| AGT AAA AAC ATC CTG GTG AAG AAA AAT GGA ACT TGC TGC ATA GCA GAC<br>Ser Lys Asn Ile Leu Val Lys Lys Asn Gly Thr Cys Cys Ile Ala Asp<br>335                      340               345              350 | 1236 |

```
CTG GGC TTG GCT GTC AAG TTC ATT AGT GAC ACA AAT GAG GTT GAC ATC     1284
Leu Gly Leu Ala Val Lys Phe Ile Ser Asp Thr Asn Glu Val Asp Ile
                355                 360                 365

CCA CCC AAC ACC CGG GTT GGC ACC AAG CGC TAT ATG CCT CCA GAA GTG     1332
Pro Pro Asn Thr Arg Val Gly Thr Lys Arg Tyr Met Pro Pro Glu Val
            370                 375                 380

CTG GAC GAG AGC TTG AAT AGA AAC CAT TTC CAG TCC TAC ATT ATG GCT     1380
Leu Asp Glu Ser Leu Asn Arg Asn His Phe Gln Ser Tyr Ile Met Ala
        385                 390                 395

GAC ATG TAC AGC TTT GGA CTC ATC CTC TGG GAG ATT GCA AGG AGA TGT     1428
Asp Met Tyr Ser Phe Gly Leu Ile Leu Trp Glu Ile Ala Arg Arg Cys
    400                 405                 410

GTT TCT GGA GGT ATA GTG GAA GAA TAC CAG CTT CCC TAT CAC GAC CTG     1476
Val Ser Gly Gly Ile Val Glu Glu Tyr Gln Leu Pro Tyr His Asp Leu
415                 420                 425                 430

GTG CCC AGT GAC CCT TCT TAT GAG GAC ATG AGA GAA ATT GTG TGC ATG     1524
Val Pro Ser Asp Pro Ser Tyr Glu Asp Met Arg Glu Ile Val Cys Met
            435                 440                 445

AAG AAG TTA CGG CCT TCA TTC CCC AAT CGA TGG AGC AGT GAT GAG TGT     1572
Lys Lys Leu Arg Pro Ser Phe Pro Asn Arg Trp Ser Ser Asp Glu Cys
        450                 455                 460

CTC AGG CAG ATG GGG AAG CTT ATG ACA GAG TGC TGG GCG CAG AAT CCT     1620
Leu Arg Gln Met Gly Lys Leu Met Thr Glu Cys Trp Ala Gln Asn Pro
    465                 470                 475

GCC TCC AGG CTG ACG GCC CTG AGA GTT AAG AAA ACC CTT GCC AAA ATG     1668
Ala Ser Arg Leu Thr Ala Leu Arg Val Lys Lys Thr Leu Ala Lys Met
480                 485                 490

TCA GAG TCC CAG GAC ATT AAA CTC TGACGTCAGA TACTTGTGGA CAGAGCAAGA    1722
Ser Glu Ser Gln Asp Ile Lys Leu
495                 500

ATTTCACAGA AGCATCGTTA GCCCAAGCCT TGAACGTTAG CCTACTGCCC AGTGAGTTCA   1782

GACTTTCCTG GAAGAGAGCA CGGTGGGCAG ACACAGAGGA ACCCAGAAAC ACGGATTCAT   1842

CATGGCTTTC TGAGGAGGAG AAACTGTTTG GGTAACTTGT TCAAGATATG ATGCATGTTG   1902

CTTTCTAAGA AAGCCCTGTA TTTTGAATTA CCATTTTTTT ATAAAAAAAA              1952

(2) INFORMATION FOR SEQ ID NO: 18:

(i) SEQUENCE CHARACTERISTICS:
        (A) LENGTH: 502 amino acids
        (B) TYPE: amino acid
        (D) TOPOLOGY: linear (ii) MOLECULE TYPE: protein (xi) SEQUENCE DESCRIPTION: SEQ ID NO: 18:

Met Leu Leu Arg Ser Ser Gly Lys Leu Asn Val Gly Thr Lys Lys Glu
  1               5                  10                  15

Asp Gly Glu Ser Thr Ala Pro Thr Pro Arg Pro Lys Ile Leu Arg Cys
                 20                  25                  30

Lys Cys His His His Cys Pro Glu Asp Ser Val Asn Asn Ile Cys Ser
             35                  40                  45

Thr Asp Gly Tyr Cys Phe Thr Met Ile Glu Glu Asp Asp Ser Gly Met
         50                  55                  60

Pro Val Val Thr Ser Gly Cys Leu Gly Leu Glu Gly Ser Asp Phe Gln
 65                  70                  75                  80

Cys Arg Asp Thr Pro Ile Pro His Gln Arg Arg Ser Ile Glu Cys Cys
                 85                  90                  95

Thr Glu Arg Asn Glu Cys Asn Lys Asp Leu His Pro Thr Leu Pro Pro
```

```
                    100                 105                  110
Leu Lys Asp Arg Asp Phe Val Asp Gly Pro Ile His His Lys Ala Leu
            115                 120                 125
Leu Ile Ser Val Thr Val Cys Ser Leu Leu Val Leu Ile Ile Leu
        130                 135                 140
Phe Cys Tyr Phe Arg Tyr Lys Arg Gln Glu Ala Arg Pro Arg Tyr Ser
145                 150                 155                 160
Ile Gly Leu Glu Gln Asp Glu Thr Tyr Ile Pro Pro Gly Glu Ser Leu
                165                 170                 175
Arg Asp Leu Ile Glu Gln Ser Gln Ser Ser Gly Ser Gly Ser Gly Leu
            180                 185                 190
Pro Leu Leu Val Gln Arg Thr Ile Ala Lys Gln Ile Gln Met Val Lys
        195                 200                 205
Gln Ile Gly Lys Gly Arg Tyr Gly Glu Val Trp Met Gly Lys Trp Arg
    210                 215                 220
Gly Glu Lys Val Ala Val Lys Val Phe Phe Thr Thr Glu Glu Ala Ser
225                 230                 235                 240
Trp Phe Arg Glu Thr Glu Ile Tyr Gln Thr Val Leu Met Arg His Glu
                245                 250                 255
Asn Ile Leu Gly Phe Ile Ala Ala Asp Ile Lys Gly Thr Gly Ser Trp
            260                 265                 270
Thr Gln Leu Tyr Leu Ile Thr Asp Tyr His Glu Asn Gly Ser Leu Tyr
        275                 280                 285
Asp Tyr Leu Lys Ser Thr Thr Leu Asp Ala Lys Ser Met Leu Lys Leu
    290                 295                 300
Ala Tyr Ser Ser Val Ser Gly Leu Cys His Leu His Thr Glu Ile Phe
305                 310                 315                 320
Ser Thr Gln Gly Lys Pro Ala Ile Ala His Arg Asp Leu Lys Ser Lys
                325                 330                 335
Asn Ile Leu Val Lys Lys Asn Gly Thr Cys Cys Ile Ala Asp Leu Gly
            340                 345                 350
Leu Ala Val Lys Phe Ile Ser Asp Thr Asn Glu Val Asp Ile Pro Pro
        355                 360                 365
Asn Thr Arg Val Gly Thr Lys Arg Tyr Met Pro Pro Glu Val Leu Asp
370                 375                 380
Glu Ser Leu Asn Arg Asn His Phe Gln Ser Tyr Ile Met Ala Asp Met
385                 390                 395                 400
Tyr Ser Phe Gly Leu Ile Leu Trp Glu Ile Ala Arg Arg Cys Val Ser
                405                 410                 415
Gly Gly Ile Val Glu Glu Tyr Gln Leu Pro Tyr His Asp Leu Val Pro
            420                 425                 430
Ser Asp Pro Ser Tyr Glu Asp Met Arg Glu Ile Val Cys Met Lys Lys
        435                 440                 445
Leu Arg Pro Ser Phe Pro Asn Arg Trp Ser Ser Asp Glu Cys Leu Arg
    450                 455                 460
Gln Met Gly Lys Leu Met Thr Glu Cys Trp Ala Gln Asn Pro Ala Ser
465                 470                 475                 480
Arg Leu Thr Ala Leu Arg Val Lys Lys Thr Leu Ala Lys Met Ser Glu
                485                 490                 495
Ser Gln Asp Ile Lys Leu
                500

(2) INFORMATION FOR SEQ ID NO: 19:
```

```
        (i) SEQUENCE CHARACTERISTICS:
            (A) LENGTH: 28 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 19:

GCGGATCCTG TTGTGAAGGN AATATGTG                                               28

(2) INFORMATION FOR SEQ ID NO: 20:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 20:

GCGATCCGTC GCAGTCAAAA TTTT                                                   24

(2) INFORMATION FOR SEQ ID NO: 21:

(i) SEQUENCE CHARACTERISTICS:
            (A) LENGTH: 26 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 21:

GCGGATCCGC GATATATTAA AAGCAA                                                 26

(2) INFORMATION FOR SEQ ID NO: 22:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: YES (xi) SEQUENCE DESCRIPTION: SEQ ID NO: 22:

CGGAATTCTG GTGCCATATA                                                        20

(2) INFORMATION FOR SEQ ID NO: 23:

(i) SEQUENCE CHARACTERISTICS:
            (A) LENGTH: 37 base pairs
            (B) TYPE: nucleic acid
            (C) STRANDEDNESS: single
```

(D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 23:

ATTCAAGGGC ACATCAACTT CATTTGTGTC ACTGTTG                                37

(2) INFORMATION FOR SEQ ID NO: 24:

(i) SEQUENCE CHARACTERISTICS:
            (A) LENGTH: 26 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 24:

GCGGATCCAC CATGGCGGAG TCGGCC                                             26

(2) INFORMATION FOR SEQ ID NO: 25:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 25:

AACACCGGGC CGGCGATGAT                                                    20

(2) INFORMATION FOR SEQ ID NO: 26:

(i) SEQUENCE CHARACTERISTICS:
            (A) LENGTH: 6 amino acids
            (B) TYPE: amino acid
            (D) TOPOLOGY: linear (ii) MOLECULE TYPE: peptide (v) FRAGMENT TYPE: internal (xi) SEQUENCE DESCRIPTION: SEQ ID NO: 26:

Gly Xaa Gly Xaa Xaa Gly
1               5

(2) INFORMATION FOR SEQ ID NO: 27:

(i) SEQUENCE CHARACTERISTICS:
            (A) LENGTH: 6 amino acids
            (B) TYPE: amino acid
            (D) TOPOLOGY: linear (ii) MOLECULE TYPE: peptide (xi) SEQUENCE DESCRIPTION: SEQ ID NO: 27:

Asp Phe Lys Ser Arg Asn

```
1               5

(2) INFORMATION FOR SEQ ID NO: 28:

(i) SEQUENCE CHARACTERISTICS:
        (A) LENGTH: 6 amino acids
        (B) TYPE: amino acid
        (D) TOPOLOGY: linear (ii) MOLECULE TYPE: peptide (xi) SEQUENCE DESCRIPTION: SEQ ID NO: 28:

Asp Leu Lys Ser Lys Asn
1               5

(2) INFORMATION FOR SEQ ID NO: 29:

(i) SEQUENCE CHARACTERISTICS:
        (A) LENGTH: 6 amino acids
        (B) TYPE: amino acid
        (D) TOPOLOGY: linear (ii) MOLECULE TYPE: peptide (xi) SEQUENCE DESCRIPTION: SEQ ID NO: 29:

Gly Thr Lys Arg Tyr Met
1               5

(2) INFORMATION FOR SEQ ID NO: 30:

(i) SEQUENCE CHARACTERISTICS:
        (A) LENGTH: 513 amino acids
        (B) TYPE: amino acid
        (D) TOPOLOGY: linear (ii) MOLECULE TYPE: peptide (xi) SEQUENCE DESCRIPTION: SEQ ID NO: 30:

Met Gly Ala Ala Ala Lys Leu Ala Phe Ala Val Phe Leu Ile Ser Cys
1               5                   10                  15

Ser Ser Gly Ala Ile Leu Gly Arg Ser Glu Thr Gln Glu Cys Leu Phe
                20                  25                  30

Phe Asn Ala Asn Trp Glu Lys Asp Arg Thr Asn Gln Thr Gly Val Glu
            35                  40                  45

Pro Cys Tyr Gly Asp Lys Asp Lys Arg Arg His Cys Phe Ala Thr Trp
        50                  55                  60

Lys Asn Ile Ser Gly Ser Ile Glu Ile Val Lys Gln Gly Cys Trp Leu
65                  70                  75                  80

Asp Asp Ile Asn Cys Tyr Asp Arg Thr Asp Cys Val Glu Lys Lys Asp
                85                  90                  95

Ser Pro Glu Val Tyr Phe Cys Cys Cys Glu Gly Asn Met Cys Asn Glu
            100                 105                 110

Lys Phe Ser Tyr Phe Pro Glu Met Glu Val Thr Gln Pro Thr Ser Asn
        115                 120                 125

Pro Val Thr Pro Lys Pro Pro Tyr Tyr Asn Ile Leu Leu Tyr Ser Leu
    130                 135                 140

Val Pro Leu Met Leu Ile Ala Gly Ile Val Ile Cys Ala Phe Trp Val
145                 150                 155                 160

Tyr Arg His His Lys Met Ala Tyr Pro Pro Val Leu Val Pro Thr Gln
                165                 170                 175

Asp Pro Gly Pro Pro Pro Pro Ser Pro Leu Leu Gly Leu Lys Pro Leu
            180                 185                 190
```

-continued

```
Gln Leu Leu Glu Val Lys Ala Arg Gly Arg Phe Gly Cys Val Trp Lys
        195                 200                 205

Ala Gln Leu Leu Asn Glu Tyr Val Ala Val Lys Ile Phe Pro Ile Gln
    210                 215                 220

Asp Lys Gln Ser Trp Gln Asn Glu Tyr Glu Val Tyr Ser Leu Pro Gly
225                 230                 235                 240

Met Lys His Glu Asn Ile Leu Gln Phe Ile Gly Ala Glu Lys Arg Gly
                245                 250                 255

Thr Ser Val Asp Val Asp Leu Trp Leu Ile Thr Ala Phe His Glu Lys
            260                 265                 270

Gly Ser Leu Ser Asp Phe Leu Lys Ala Asn Val Val Ser Trp Asn Glu
        275                 280                 285

Leu Cys His Ile Ala Glu Thr Met Ala Arg Gly Leu Ala Tyr Leu His
    290                 295                 300

Glu Asp Ile Pro Gly Leu Lys Asp Gly His Lys Pro Ala Ile Ser His
305                 310                 315                 320

Arg Asp Ile Lys Ser Lys Asn Val Leu Leu Lys Asn Asn Leu Thr Ala
                325                 330                 335

Cys Ile Ala Asp Phe Gly Leu Ala Leu Lys Phe Glu Ala Gly Lys Ser
            340                 345                 350

Ala Gly Asp Thr His Gly Gln Val Gly Thr Arg Arg Tyr Met Ala Pro
        355                 360                 365

Glu Val Leu Glu Gly Ala Ile Asn Phe Gln Arg Asp Ala Phe Leu Arg
    370                 375                 380

Ile Asp Met Tyr Ala Met Gly Leu Val Leu Trp Glu Leu Ala Ser Arg
385                 390                 395                 400

Cys Thr Ala Ala Asp Gly Pro Val Asp Glu Tyr Met Leu Pro Phe Glu
                405                 410                 415

Glu Glu Ile Gly Gln His Pro Ser Leu Glu Asp Met Gln Glu Val Val
            420                 425                 430

Val His Lys Lys Lys Arg Pro Val Leu Arg Asp Tyr Trp Gln Lys His
        435                 440                 445

Ala Gly Met Ala Met Leu Cys Glu Thr Ile Glu Glu Cys Trp Asp His
    450                 455                 460

Asp Ala Glu Ala Arg Leu Ser Ala Gly Cys Val Gly Glu Arg Ile Thr
465                 470                 475                 480

Gln Met Gln Arg Leu Thr Asn Ile Ile Thr Thr Glu Asp Ile Val Thr
                485                 490                 495

Val Val Thr Met Val Thr Asn Val Asp Phe Pro Pro Lys Glu Ser Ser
            500                 505                 510

Leu
```

(2) INFORMATION FOR SEQ ID NO: 31:

(i) SEQUENCE CHARACTERISTICS:
        (A) LENGTH: 536 amino acids
        (B) TYPE: amino acid
        (D) TOPOLOGY: linear (ii) MOLECULE TYPE: peptide (xi) SEQUENCE DESCRIPTION: SEQ ID NO: 31:

```
Met Thr Ala Pro Trp Ala Ala Leu Ala Leu Leu Trp Gly Ser Leu Cys
1               5                   10                  15

Ala Gly Ser Gly Arg Gly Glu Ala Glu Thr Arg Glu Cys Ile Tyr Tyr
            20                  25                  30
```

-continued

```
Asn Ala Asn Trp Glu Leu Glu Arg Thr Asn Gln Ser Gly Leu Glu Arg
     35                  40                  45

Cys Glu Gly Glu Gln Asp Lys Arg Leu His Cys Tyr Ala Ser Trp Arg
 50                  55                  60

Asn Ser Ser Gly Thr Ile Glu Leu Val Lys Lys Gly Cys Trp Leu Asp
 65                  70                  75                  80

Asp Phe Asn Cys Tyr Asp Arg Gln Glu Cys Val Ala Thr Glu Glu Asn
                 85                  90                  95

Pro Gln Val Tyr Phe Cys Cys Cys Glu Gly Asn Phe Cys Asn Glu Arg
                100                 105                 110

Phe Thr His Leu Pro Glu Pro Gly Gly Pro Glu Val Thr Tyr Glu Pro
            115                 120                 125

Pro Pro Thr Ala Pro Thr Leu Leu Thr Val Leu Ala Tyr Ser Leu Leu
130                 135                 140

Pro Ile Gly Gly Leu Ser Leu Ile Val Leu Leu Ala Phe Trp Met Tyr
145                 150                 155                 160

Arg His Arg Lys Pro Pro Tyr Gly His Val Asp Ile His Glu Val Arg
                165                 170                 175

Gln Cys Gln Arg Trp Ala Gly Arg Arg Asp Gly Cys Ala Asp Ser Phe
            180                 185                 190

Lys Pro Leu Pro Phe Gln Asp Pro Gly Pro Pro Pro Ser Pro Leu
            195                 200                 205

Val Gly Leu Lys Pro Leu Gln Leu Leu Glu Ile Lys Ala Arg Gly Arg
210                 215                 220

Phe Gly Cys Val Trp Lys Ala Gln Leu Met Asn Asp Phe Val Ala Val
225                 230                 235                 240

Lys Ile Phe Pro Leu Gln Asp Lys Gln Ser Trp Gln Ser Glu Arg Glu
                245                 250                 255

Ile Phe Ser Thr Pro Gly Met Lys His Glu Asn Leu Leu Gln Phe Ile
            260                 265                 270

Ala Ala Glu Lys Arg Gly Ser Asn Leu Glu Val Glu Leu Trp Leu Ile
        275                 280                 285

Thr Ala Phe His Asp Lys Gly Ser Leu Thr Asp Tyr Leu Lys Gly Asn
290                 295                 300

Ile Ile Thr Trp Asn Glu Leu Cys His Val Ala Glu Thr Met Ser Arg
305                 310                 315                 320

Gly Leu Ser Tyr Leu His Glu Asp Val Pro Trp Cys Arg Gly Glu Gly
                325                 330                 335

His Lys Pro Ser Ile Ala His Arg Asp Phe Lys Ser Lys Asn Val Leu
            340                 345                 350

Leu Lys Ser Asp Leu Thr Ala Val Leu Ala Asp Phe Gly Leu Ala Val
        355                 360                 365

Arg Phe Glu Pro Gly Lys Pro Pro Gly Asp Thr His Gly Gln Val Gly
370                 375                 380

Thr Arg Arg Tyr Met Ala Pro Glu Val Leu Glu Gly Ala Ile Asn Phe
385                 390                 395                 400

Gln Arg Asp Ala Phe Leu Arg Ile Asp Met Tyr Ala Met Gly Leu Val
                405                 410                 415

Leu Trp Glu Leu Val Ser Arg Cys Lys Ala Ala Asp Gly Pro Val Asp
            420                 425                 430

Glu Tyr Met Leu Pro Phe Glu Glu Ile Gly Gln His Pro Ser Leu
            435                 440                 445

Glu Glu Leu Gln Glu Val Val Val His Lys Lys Met Arg Pro Thr Ile
450                 455                 460
```

```
Lys Asp His Trp Leu Lys His Pro Gly Leu Ala Gln Leu Cys Val Thr
465                 470                 475                 480

Ile Glu Glu Cys Trp Asp His Asp Ala Glu Ala Arg Leu Ser Ala Gly
            485                 490                 495

Cys Val Glu Glu Arg Val Ser Leu Ile Arg Arg Ser Val Asn Gly Thr
        500                 505                 510

Thr Ser Asp Cys Leu Val Ser Leu Val Thr Ser Val Thr Asn Val Asp
        515                 520                 525

Leu Leu Pro Lys Glu Ser Ser Ile
        530             535
```

(2) INFORMATION FOR SEQ ID NO: 32:

(i) SEQUENCE CHARACTERISTICS:
        (A) LENGTH: 567 amino acids
        (B) TYPE: amino acid
        (D) TOPOLOGY: linear (ii) MOLECULE TYPE: peptide (xi) SEQUENCE DESCRIPTION: SEQ ID NO: 32:

```
Met Gly Arg Gly Leu Leu Arg Gly Leu Trp Pro Leu His Ile Val Leu
1               5                   10                  15

Trp Thr Arg Ile Ala Ser Thr Ile Pro Pro His Val Gln Lys Ser Val
            20                  25                  30

Asn Asn Asp Met Ile Val Thr Asp Asn Asn Gly Ala Val Lys Phe Pro
            35                  40                  45

Gln Leu Cys Lys Phe Cys Asp Val Arg Phe Ser Thr Cys Asp Asn Gln
50                  55                  60

Lys Ser Cys Met Ser Asn Cys Ser Ile Thr Ser Ile Cys Glu Lys Pro
65                  70                  75                  80

Gln Glu Val Cys Val Ala Val Trp Arg Lys Asn Asp Glu Asn Ile Thr
                85                  90                  95

Leu Glu Thr Val Cys His Asp Pro Lys Leu Pro Tyr His Asp Phe Ile
                100                 105                 110

Leu Glu Asp Ala Ala Ser Pro Lys Cys Ile Met Lys Glu Lys Lys Lys
            115                 120                 125

Pro Gly Glu Thr Phe Phe Met Cys Ser Cys Ser Ser Asp Glu Cys Asn
130                 135                 140

Asp Asn Ile Ile Phe Ser Glu Glu Tyr Asn Thr Ser Asn Pro Asp Leu
145                 150                 155                 160

Leu Leu Val Ile Phe Gln Val Thr Gly Ile Ser Leu Leu Pro Pro Leu
                165                 170                 175

Gly Val Ala Ile Ser Val Ile Ile Ile Phe Tyr Cys Tyr Arg Val Asn
            180                 185                 190

Arg Gln Gln Lys Leu Ser Ser Thr Trp Glu Thr Gly Lys Thr Arg Lys
            195                 200                 205

Leu Met Glu Phe Ser Glu His Cys Ala Ile Ile Leu Glu Asp Asp Arg
            210                 215                 220

Ser Asp Ile Ser Ser Thr Cys Ala Asn Asn Ile Asn His Asn Thr Glu
225                 230                 235                 240

Leu Leu Pro Ile Glu Leu Asp Thr Leu Val Gly Lys Gly Arg Phe Ala
                245                 250                 255

Glu Val Tyr Lys Ala Lys Leu Lys Gln Asn Thr Ser Glu Gln Phe Glu
            260                 265                 270

Thr Val Ala Val Lys Ile Phe Pro Tyr Glu Glu Tyr Ala Ser Trp Lys
```

```
                    275                 280                 285
Thr Glu Lys Asp Ile Phe Ser Asp Ile Asn Leu Lys His Glu Asn Ile
290                 295                 300

Leu Gln Phe Leu Thr Ala Glu Arg Lys Thr Glu Leu Gly Lys Gln
305                 310                 315                 320

Tyr Trp Leu Ile Thr Ala Phe His Ala Lys Gly Asn Leu Gln Glu Tyr
                325                 330                 335

Leu Thr Arg His Val Ile Ser Trp Glu Asp Leu Arg Lys Leu Gly Ser
                340                 345                 350

Ser Leu Ala Arg Gly Ile Ala His Leu His Ser Asp His Thr Pro Cys
                355                 360                 365

Gly Arg Pro Lys Met Pro Ile Val His Arg Asp Leu Lys Ser Ser Asn
370                 375                 380

Ile Leu Val Lys Asn Asp Leu Thr Cys Cys Leu Cys Asp Phe Gly Leu
385                 390                 395                 400

Ser Leu Arg Leu Asp Pro Thr Leu Ser Val Asp Asp Leu Ala Asn Ser
                405                 410                 415

Gly Gln Val Gly Thr Ala Arg Tyr Met Ala Pro Glu Val Leu Glu Ser
                420                 425                 430

Arg Met Asn Leu Glu Asn Ala Glu Ser Phe Lys Gln Thr Asp Val Tyr
435                 440                 445

Ser Met Ala Leu Val Leu Trp Glu Met Thr Ser Arg Cys Asn Ala Val
450                 455                 460

Gly Glu Val Lys Asp Tyr Glu Pro Pro Phe Gly Ser Lys Val Arg Glu
465                 470                 475                 480

His Pro Cys Val Glu Ser Met Lys Asp Asn Val Leu Arg Asp Arg Gly
                485                 490                 495

Arg Pro Glu Ile Pro Ser Phe Trp Leu Asn His Gln Gly Ile Gln Met
                500                 505                 510

Val Cys Glu Thr Leu Thr Glu Cys Trp Asp His Asp Pro Glu Ala Arg
                515                 520                 525

Leu Thr Ala Gln Cys Val Ala Glu Arg Phe Ser Glu Leu Glu His Leu
                530                 535                 540

Asp Arg Leu Ser Gly Arg Ser Cys Ser Glu Glu Lys Ile Pro Glu Asp
545                 550                 555                 560

Gly Ser Leu Asn Thr Thr Lys
                565

(2) INFORMATION FOR SEQ ID NO: 33:

(i) SEQUENCE CHARACTERISTICS:
        (A) LENGTH: 178 amino acids
        (B) TYPE: amino acid
        (D) TOPOLOGY: linear (ii) MOLECULE TYPE: peptide (xi) SEQUENCE DESCRIPTION: SEQ ID NO: 33:

Leu Thr Gly Arg Val Gly Ser Gly Arg Phe Gly Asn Val Ser Arg Gly
1               5                   10                  15

Asp Tyr Arg Gly Glu Ala Val Ala Val Lys Val Phe Asn Ala Ile Asp
                20                  25                  30

Glu Pro Ala Phe His Lys Glu Ile Glu Ile Phe Glu Thr Arg Met Leu
                35                  40                  45

Arg His Pro Asn Val Leu Arg Tyr Ile Gly Ser Asp Arg Val Asp Thr
50                  55                  60
```

```
Gly Phe Val Thr Glu Leu Trp Leu Val Ile Glu Tyr His Pro Ser Gly
 65                  70                  75                  80

Ser Leu His Asp Phe Leu Leu Glu Asn Thr Val Asn Ile Glu Thr Tyr
                 85                  90                  95

Tyr Asn Leu Met Arg Ser Thr Ala Ser Gly Leu Ala Phe Leu His Asn
            100                 105                 110

Gln Ile Gly Gly Ser Lys Glu Ser Asn Lys Pro Ala Met Ala His Arg
                115                 120                 125

Asp Ile Lys Ser Lys Asn Ile Met Tyr Lys Asn Asp Leu Thr Cys Ala
            130                 135                 140

Ile Gly Asp Leu Gly Leu Ser Leu Ser Lys Pro Glu Asp Ala Ala Ser
145                 150                 155                 160

Asp Ile Ile Ala Asn Glu Asn Tyr Lys Cys Gly Thr Val Arg Tyr Leu
                165                 170                 175

Ala Pro
```

(2) INFORMATION FOR SEQ ID NO: 34:

(i) SEQUENCE CHARACTERISTICS:
        (A) LENGTH: 130 amino acids
        (B) TYPE: amino acid
        (D) TOPOLOGY: linear (ii) MOLECULE TYPE: peptide (xi) SEQUENCE DESCRIPTION: SEQ ID NO: 34

```
Thr Arg Leu His Leu Cys His Cys Ser Arg Glu Val Gly Cys Asn Ala
  1               5                  10                  15

Arg Thr Thr Gly Trp Val Pro Gly Ile Glu Phe Leu Asn Glu Thr Asp
                 20                  25                  30

Arg Ser Phe Tyr Glu Asn Thr Cys Tyr Thr Asp Gly Ser Cys Tyr Gln
                 35                  40                  45

Ser Ala Arg Pro Ser Pro Glu Ile Ser His Phe Gly Cys Met Asp Glu
            50                  55                  60

Lys Ser Val Thr Asp Glu Thr Glu Phe His Asp Thr Ala Ala Lys Val
 65                  70                  75                  80

Cys Thr Asn Asn Thr Lys Asp Pro His Ala Thr Val Trp Ile Cys Cys
                 85                  90                  95

Asp Lys Gly Asn Phe Cys Ala Asn Glu Thr Ile Ile His Leu Ala Pro
                100                 105                 110

Gly Pro Gln Gln Ser Ser Thr Trp Leu Ile Leu Thr Ile Leu Ala Leu
            115                 120                 125

Leu Thr
130
```

(2) INFORMATION FOR SEQ ID NO: 35:

(i) SEQUENCE CHARACTERISTICS:
        (A) LENGTH: 6 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO: 35:

```
Asp Leu Lys Pro Glu Asn
  1               5
```

(2) INFORMATION FOR SEQ ID NO: 36:

(i) SEQUENCE CHARACTERISTICS:
       (A) LENGTH: 6 amino acids
       (B) TYPE: amino acid
       (D) TOPOLOGY: linear (ii) MOLECULE TYPE: peptide (v) FRAGMENT TYPE: internal (xi) SEQUENCE DESCRIPTION: SEQ ID NO: 36:

Asp Leu Ala Ala Arg Asn
1               5

(2) INFORMATION FOR SEQ ID NO: 37:

(i) SEQUENCE CHARACTERISTICS:
       (A) LENGTH: 6 amino acids
       (B) TYPE: amino acid
       (D) TOPOLOGY: linear (ii) MOLECULE TYPE: peptide (v) FRAGMENT TYPE: internal (xi) SEQUENCE DESCRIPTION: SEQ ID NO: 37:

Gly Thr Xaa Xaa Tyr Xaa
1               5

(2) INFORMATION FOR SEQ ID NO: 38:

(i) SEQUENCE CHARACTERISTICS:
       (A) LENGTH: 6 amino acids
       (B) TYPE: amino acid
       (D) TOPOLOGY: linear (ii) MOLECULE TYPE: peptide (v) FRAGMENT TYPE: internal (xi) SEQUENCE DESCRIPTION: SEQ ID NO: 38:

Gly Thr Xaa Xaa Phe Xaa
1               5

(2) INFORMATION FOR SEQ ID NO: 39:

(i) SEQUENCE CHARACTERISTICS:
       (A) LENGTH: 6 amino acids
       (B) TYPE: amino acid
       (D) TOPOLOGY: linear (ii) MOLECULE TYPE: peptide (v) FRAGMENT TYPE: internal (xi) SEQUENCE DESCRIPTION: SEQ ID NO: 39:

Gly Ser Xaa Xaa Tyr Xaa
1               5

(2) INFORMATION FOR SEQ ID NO: 40:

(i) SEQUENCE CHARACTERISTICS:
       (A) LENGTH: 6 amino acids
       (B) TYPE: amino acid
       (D) TOPOLOGY: linear (ii) MOLECULE TYPE: peptide (v) FRAGMENT TYPE: internal (xi) SEQUENCE DESCRIPTION: SEQ ID NO: 40:

```
Gly Ser Xaa Xaa Phe Xaa
1               5

(2) INFORMATION FOR SEQ ID NO: 41:

(i) SEQUENCE CHARACTERISTICS:
        (A) LENGTH: 6 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO: 41:

Xaa Pro Ile Lys Trp Thr
1               5

(2) INFORMATION FOR SEQ ID NO: 42:

(i) SEQUENCE CHARACTERISTICS:
        (A) LENGTH: 6 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO: 42:

Xaa Pro Ile Lys Trp Met
1               5

(2) INFORMATION FOR SEQ ID NO: 43:

(i) SEQUENCE CHARACTERISTICS:
        (A) LENGTH: 6 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO: 43:

Xaa Pro Ile Arg Trp Thr
1               5

(2) INFORMATION FOR SEQ ID NO: 44:

(i) SEQUENCE CHARACTERISTICS:
        (A) LENGTH: 6 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO: 44:

Xaa Pro Ile Arg Trp Met
1               5

(2) INFORMATION FOR SEQ ID NO: 45:

(i) SEQUENCE CHARACTERISTICS:
        (A) LENGTH: 6 amino acids
        (B) TYPE: amino acid
        (D) TOPOLOGY: linear
```

```
        (ii) MOLECULE TYPE: peptide (v) FRAGMENT TYPE: internal (xi) SEQUENCE DESCRIPTION: SEQ ID NO: 45:

Xaa Pro Val Lys Trp Thr
1               5

(2) INFORMATION FOR SEQ ID NO: 46:

(i) SEQUENCE CHARACTERISTICS:
            (A) LENGTH: 6 amino acids
            (B) TYPE: amino acid
            (D) TOPOLOGY: linear (ii) MOLECULE TYPE: peptide (v) FRAGMENT TYPE: internal (xi) SEQUENCE DESCRIPTION: SEQ ID NO: 46:

Xaa Pro Val Lys Trp Met
1               5

(2) INFORMATION FOR SEQ ID NO: 47:

(i) SEQUENCE CHARACTERISTICS:
            (A) LENGTH: 6 amino acids
            (B) TYPE: amino acid
            (D) TOPOLOGY: linear (ii) MOLECULE TYPE: peptide (v) FRAGMENT TYPE: internal (xi) SEQUENCE DESCRIPTION: SEQ ID NO: 47:

Xaa Pro Val Arg Trp Thr
1               5

(2) INFORMATION FOR SEQ ID NO: 48:

(i) SEQUENCE CHARACTERISTICS:
            (A) LENGTH: 6 amino acids
            (B) TYPE: amino acid
            (D) TOPOLOGY: linear (ii) MOLECULE TYPE: peptide (v) FRAGMENT TYPE: internal (xi) SEQUENCE DESCRIPTION: SEQ ID NO: 48:

Xaa Pro Val Arg Trp Met
1               5
```

ANTIBODIES WHICH BIND SPECIFICALLY TO ACTIVIN RECEPTOR LIKE KINASE 3

RELATED APPLICATIONS

This application is a continuation application of application Ser. No. 11/656,720, filed Jan. 23, 2007, now U.S. Pat. No. 7,932,351 which is a divisional of application Ser. No. 10/630,555, filed Jul. 30, 2003, now U.S. Pat. No. 7,592,428 which is a divisional of application Ser. No. 09/903,068, filed Jul. 11, 2001, now U.S. Pat. No. 6,982,319, which is a divisional application of application Ser. No. 09/679,187, filed Oct. 3, 2000, now U.S. Pat. No. 6,331,621, which is a divisional application of application Ser. No. 08/436,265, filed Oct. 30, 1995, now U.S. Pat. No. 6,316,217, which is a 35 U.S.C. §371 of PCT/GB93/02367, filed Nov. 17, 1993.

FIELD OF THE INVENTION

This invention relates to proteins having serine/threonine kinase domains, corresponding nucleic acid molecules, and their use.

BACKGROUND OF THE INVENTION

The transforming growth factor-$\beta$ (TGF-$\beta$) superfamily consists of a family of structurally-related proteins, including three different mammalian isoforms of TGF-$\beta$ (TGF-$\beta$1, $\beta$2 and $\beta$3), activins, inhibins, mullerian-inhibiting substance and bone morphogenic proteins (BMPs) (for reviews see Roberts and Sporn, (1990) Peptide Growth Factors and Their Receptors, Pt. 1, Sporn and Roberts, eds. (Berlin: Springer-Verlag) pp 419-472; Moses et al (1990) Cell 63, 245-247). The proteins of the TGF-$\beta$ superfamily have a wide variety of biological activities. TGF-$\beta$ acts as a growth inhibitor for many cell types and appears to play a central role in the regulation of embryonic development, tissue regeneration, immuno-regulation, as well as in fibrosis and carcinogenesis (Roberts and Sporn (199) see above).

Activins and inhibins were originally identified as factors which regulate secretion of follicle-stimulating hormone secretion (Vale et al (1990) Peptide Growth Factors and Their Receptors, Pt. 2, Sporn and Roberts, eds. (Berlin: Springer-Verlag) pp. 211-248). Activins were also shown to induce the differentiation of haematopoietic progenitor cells (Murata et al (1988) Proc. Natl. Acad. Sci. USA 85, 2434-2438; Eto et al (1987) Biochem. Biophys. Res. Commun. 142, 1095-1103) and induce mesoderm formation in *Xenopus* embryos (Smith et al (1990) Nature 345, 729-731; van den Eijnden-Van Raaij et al (1990) Nature 345, 732-734).

BMPs or osteogenic proteins which induce the formation of bone and cartilage when implanted subcutaneously (Wozney et al (1988) Science 242, 1528-1534), facilitate neuronal differentiation (Paralkar et al (1992) J. Cell Biol. 119, 1721-1728) and induce monocyte chemotaxis (Cunningham et al (1992) Proc. Natl. Acad. Sci. USA 89, 11740-11744). Müllerian-inhibiting substance induces regression of the Müllerian duct in the male reproductive system (Cate et al (1986) Cell 45, 685-698), and a glial cell line-derived neurotrophic factor enhances survival of midbrain dopaminergic neurons (Lin et al (1993) Science 260, 1130-1132). The action of these growth factors is mediated through binding to specific cell surface receptors.

Within this family, TGF-$\beta$ receptors have been most thoroughly characterized. By covalently cross-linking radio-labelled TGF-$\beta$ to cell surface molecules followed by polyacrylamide gel electrophoresis of the affinity-labelled complexes, three distinct size classes of cell surface proteins (in most cases) have been identified, denoted receptor type I (53 kd), type II (75 kd), type III or betaglycan (a 300 kd proteoglycan with a 120 kd core protein) (for a review see Massague (1992) Cell 69 1067-1070) and more recently endoglin (a homodimer of two 95 kd subunits) (Cheifetz et al (1992) J. Biol. Chem. 267 19027-19030). Current evidence suggests that type I and type II receptors are directly involved in receptor signal transduction (Seciarini et al (1989) Mol. Endo., 3, 261-272; Laiho et al (1991) J. Biol. Chem. 266, 9100-9112) and may form a heteromeric complex; the type II receptor is needed for the binding of TGF-$\beta$ to the type I receptor and the type I receptor is needed for the signal transduction induced by the type II receptor (Wrana et al (1992) Cell, 71, 1003-1004). The type III receptor and endoglin may have more indirect roles, possibly by facilitating the binding of ligand to type II receptors (Wang et al (1991) Cell, 67 797-805; Lopez-Casillas et al (1993) Cell, 73 1435-1444).

Binding analyses with activin A and BMP4 have led to the identification of two co-existing cross-linked affinity complexes of 50-60 kDa and 70-80 kDa on responsive cells (Hino et al (1989) J. Biol. Chem. 264, 10309-10314; Mathews and Vale (1991), Cell 68, 775-785; Paralker et al (1991) Proc. Natl. Acad. Sci. USA 87, 8913-8917). By analogy with TGF-$\beta$ receptors they are thought to be signalling receptors and have been named type I and type II receptors.

Among the type II receptors for the TGF-$\beta$ superfamily of proteins, the cDNA for the activin type II receptor (Act RII) was the first to be cloned (Mathews and Vale (1991) Cell 65, 973-982). The predicted structure of the receptor was shown to be a transmembrane protein with an intracellular serine/threonine kinase domain. The activin receptor is related to the *C. elegans* daf-1 gene product, but the ligand is currently unknown (Georgi et al (1990) Cell 61, 635-645). Thereafter, another form of the activin type II receptor (activin type IIB receptor), of which there are different splicing variants (Mathews et al (1992), Science 225, 1702-1705; Attisano et al (1992) Cell 68, 97-108), and the TGF-$\beta$ type II receptor (T$\beta$RII) (Lin et al (1992) Cell 68, 775-785) were cloned, both of which have putative serine/threonine kinase domains.

SUMMARY OF THE INVENTION

The present invention involves the discovery of related novel peptides, including peptides having the activity of those defined herein as SEQ ID Nos. 2, 4, 8, 10, 12, 14, 16 and 18. Their discovery is based on the realisation that receptor serine/threonine kinases form a new receptor family, which may include the type II receptors for other proteins in the TGF-$\beta$ superfamily. To ascertain whether there were other members of this family of receptors, a protocol was designed to clone ActRII/daf I related cDNAs. This approach made use of the polymerase chain reaction (PCR), using degenerate primers based upon the amino-acid sequence similarity between kinase domains of the mouse activin type II receptor and daf-I gene products.

This strategy resulted in the isolation of a new family of receptor kinases called Activin receptor like kinases (ALK's) 1-6. These cDNAs showed an overall 33-39% sequence similarity with ActRII and TGF-$\beta$ type II receptor and 40-92% sequence similarity towards each other in the kinase domains.

Soluble receptors according to the invention comprise at least predominantly the extracellular domain. These can be selected from the information provided herein, prepared in conventional manner, and used in any manner associated with the invention.

Antibodies to the peptides described herein may be raised in conventional manner. By selecting unique sequences of the peptides, antibodies having desired specificity can be obtained.

The antibodies may be monoclonal, prepared in known manner. In particular, monoclonal antibodies to the extracellular domain are of potential value in therapy.

Products of the invention are useful in diagnostic methods, e.g. to determine the presence in a sample for an analyte binding therewith, such as in an antagonist assay. Conventional techniques, e.g. an enzyme-linked immunosorbent assay, may be used.

Products of the invention having a specific receptor activity can be used in therapy, e.g. to modulate conditions associated with activin or TGF-β activity. Such conditions include fibrosis, e.g. liver cirrhosis and pulmonary fibrosis, cancer, rheumatoid arthritis and glomeronephritis.

BRIEF DESCRIPTION OF THE DRAWINGS

FIG. 1 shows the alignment of the serine/threonine (S/T) kinase domains (I-VIII) of related receptors from transmembrane proteins, including embodiments of the present invention. The nomenclature of the subdomains is accordingly to Hanks et al (1988). The amino acid sequences are set forth at amino acids 246-427 of SEQ ID NO: 32, 216-391 of SEQ ID NO: 31, 194-368 of SEQ ID NO: 30, and 1-178 of SEQ ID NO: 33.

FIGS. 2A to 2D shows the sequences and characteristics of the respective primers used in the initial PCR reactions. The nucleic acid sequences are also given as SEQ ID Nos. 19 to 22.

FIG. 3 is a comparison of the amino-acid sequences of human activin type II receptor (Act R-II), mouse activin type IIB receptor (Act R-IIB), human TGF-β type II receptor (TβR-II), human TGF-β type I receptor (ALK-5), human activin receptor type IA (ALK-2), and type IB (ALK-4), ALKs 1 & 3 and mouse ALK-6. See SEQ ID NOS: 30, 31, 32 10, 2, 4, 6, 8, and 18.

FIG. 4 shows, schematically, the structures for Daf-1, Act R-II, Act R-IIB, TβR-II, TβR-I/ALK-5, ALK's-1, -2 (Act RIA), -3, -4 (Act RIB) & -6.

FIG. 5 shows the sequence alignment of the cysteine-rich domains of the ALKs, TβR-II, Act R-II, Act R-IIB and daf-1 receptors. See positions 34-95 of SEQ ID NO: 2, 35-99 of SEQ ID NO: 4, 61-130 of SEQ ID NO: 6, 34-100 of SEQ ID NO: 8, 36-106 of SEQ ID NO: 10, 30-110 of SEQ ID NO: 30, 29-109 of SEQ ID NO: 31, 51-143 of SEQ ID NO: 32, and 5-101 of SEQ ID NO: 34.

FIG. 6 is a comparison of kinase domains of serine/threonine kinases, showing the percentage amino-acid identity of the kinase domains.

BRIEF DESCRIPTION OF THE SEQUENCE LISTINGS

Figure 7:
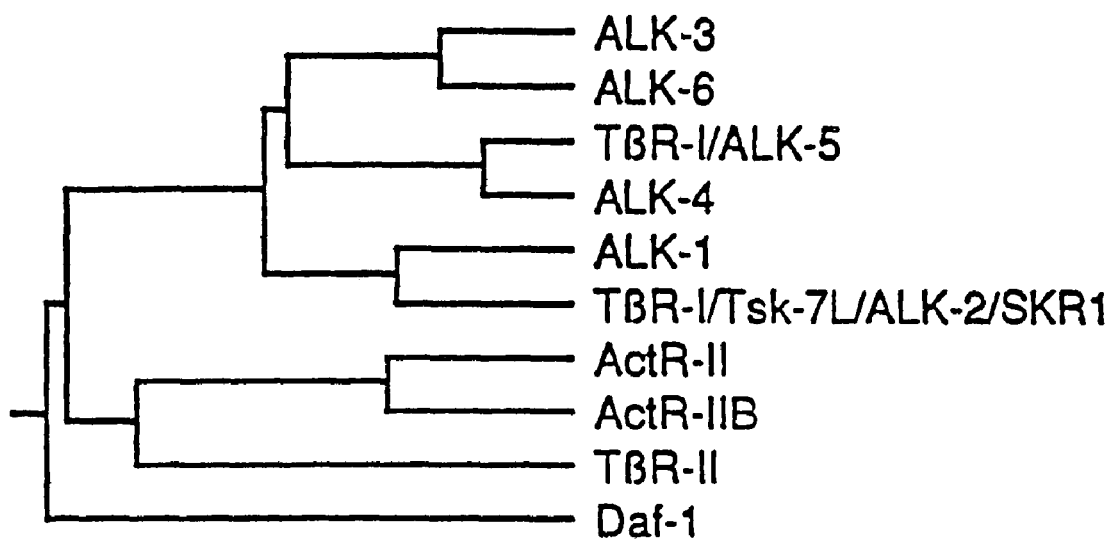
FIG. 7 shows the pairwise alignment relationship between the kinase domains of the receptor serine/threonine kinases. The dendrogram was generated using the Jotun-Hein alignment program (Hein (1990) Meth. Enzymol. 183, 626-645).

Sequences 1 and 2 are the nucleotide and deduced amino-acid sequences of cDNA for hALK-1 (clone HP57).

Sequences 3 and 4 are the nucleotide and deduced amino-acid sequences of cDNA for hALK-2 (clone HP53).

Sequences 5 and 6 are the nucleotide and deduced amino-acid sequences of cDNA for hALK-3 (clone ONF5).

Sequences 7 and 8 are the nucleotide and deduced amino-acid sequences of cDNA for hALK-4 (clone 11H8), complemented with PCR product encoding extracellular domain.

Sequences 9 and 10 are the nucleotide and deduced amino-acid sequences of cDNA for hALK-5 (clone EMBLA).

Sequences 11 and 12 are the nucleotide and deduced amino-acid sequences of cDNA for mALK-1 (clone AM6).

Sequences 13 and 14 are the nucleotide and deduced amino-acid sequences of cDNA for mALK-3 (clones ME-7 and ME-D).

Sequences 15 and 16 are the nucleotide and deduced amino-acid sequences of cDNA for mALK-4 (clone 8a1).

Sequences 17 and 18 are the nucleotide and deduced amino-acid sequences of cDNA for mALK-6 (clone ME-6).

Sequence 19 (B1-S) is a sense primer, extracellular domain, cysteine-rich region, BamHI site at 5' end, 28-mer, 64-fold degeneracy.

Sequence 20 (B3-S) is a sense primer, kinase domain II, BamHI site at 5' end, 25-mer, 162-fold degeneracy.

Sequence 21 (B7-S) is a sense primer, kinase domain VIB, S/T kinase specific residues, BamHI site at 5' end, 24-mer, 288-fold degeneracy.

Sequence 22 (E8-AS) is an anti-sense primer, kinase domain, S/T kinase-specific residues EcoRI site at 5' end, 20-mer, 18-fold degeneracy.

Sequence 23 is an oligonucleotide probe.

Sequence 24 is a 5' primer.

Sequence 25 is a 3' primer.

Sequence 26 is a consensus sequence in Subdomain I.

Sequences 27 and 28 are novel sequence motifs in Subdomain VIB.

Sequence 29 is a novel sequence motif in Subdomain VIII.

DESCRIPTION OF THE INVENTION

As described in more detail below, nucleic acid sequences have been isolated, coding for a new sub-family of serine/threonine receptor kinases. The term nucleic acid molecules as used herein refers to any sequence which codes for the murine, human or mammalian form, amino-acid sequences of which are presented herein. It is understood that the well known phenomenon of codon degeneracy provides for a great deal of sequence variation and all such varieties are included within the scope of this invention.

The nucleic acid sequences described herein may be used to clone the respective genomic DNA sequences in order to study the genes' structure and regulation. The murine and human cDNA or genomic sequences can also be used to isolate the homologous genes from other mammalian species. The mammalian DNA sequences can be used to study the receptors' functions in various in vitro and in vivo model systems.

As exemplified below for ALK-5 cDNA, it is also recognised that, given the sequence information provided herein, the artisan could easily combine the molecules with a pertinent promoter in a vector, so as to produce a cloning vehicle for expression of the molecule. The promoter and coding molecule must be operably linked via any of the well-recognized and easily-practised methodologies for so doing. The resulting vectors, as well as the isolated nucleic acid molecules themselves, may be used to transform prokaryotic cells (e.g. E. coli), or transfect eukaryotes such as yeast (S. cerevisiae), PAE, COS or CHO cell lines. Other appropriate expression systems will also be apparent to the skilled artisan.

Several methods may be used to isolate the ligands for the ALKs. As shown for ALK-5 cDNA, cDNA clones encoding the active open reading frames can be subcloned into expression vectors and transfected into eukaryotic cells, for example COS cells. The transfected cells which can express the receptor can be subjected to binding assays for radioactively-labelled members of the TGF-β superfamily (TGF-β, activins, inhibins, bone morphogenic proteins and mullerian-inhibiting substances), as it may be expected that the receptors will bind members of the TGF-β superfamily. Various biochemical or cell-based assays can be designed to identify the ligands, in tissue extracts or conditioned media, for receptors in which a ligand is not known. Antibodies raised to the receptors may also be used to identify the ligands, using the immunoprecipitation of the cross-linked complexes. Alternatively, purified receptor could be used to isolate the ligands using an affinity-based approach. The determination of the expression patterns of the receptors may also aid in the isolation of the ligand. These studies may be carried out using ALK DNA or RNA sequences as probes to perform in situ hybridisation studies.

The use of various model systems or structural studies should enable the rational development of specific agonists and antagonists useful in regulating receptor function. It may be envisaged that these can be peptides, mutated ligands, antibodies or other molecules able to interact with the receptors.

The foregoing provides examples of the invention Applicants intend to claim which includes, inter alia, isolated nucleic acid molecules coding for activin receptor-like kinases (ALKs), as defined herein. These include such sequences isolated from mammalian species such as mouse, human, rat, rabbit and monkey.

The following description relates to specific embodiments. It will be understood that the specification and examples are illustrative but not limitative of the present invention and that other embodiments within the spirit and scope of the invention will suggest themselves to those skilled in the art.

Preparation of mRNA and Construction of a cDNA Library

For construction of a cDNA library, poly (A)⁺ RNA was isolated from a human erythroleukemia cell line (HEL 92.1.7) obtained from the American Type Culture Collection (ATCC TIB 180). These cells were chosen as they have been shown to respond to both activin and TGF-β. Moreover leukaemic cells have proved to be rich sources for the cloning of novel receptor tyrosine kinases (Partanen et al (1990) Proc. Natl. Acad. Sci. USA 87, 8913-8917 and (1992) Mol. Cell. Biol. 12, 1698-1707). (Total) RNA was prepared by the guanidinium isothiocyanate method (Chirgwin et al (1979) Biochemistry 18, 5294-5299). mRNA was selected using the poly-A or poly AT tract mRNA isolation kit (Promega, Madison, Wis., U.S.A.) as described by the manufacturers, or purified through an oligo (dT)-cellulose column as described by Aviv and Leder (1972) Proc. Natl. Acad. Sci. USA 69, 1408-1412. The isolated mRNA was used for the synthesis of random primed (Amersham) cDNA, that was used to make a λgt10 library with 1×10⁵ independent cDNA clones using the Riboclone cDNA synthesis system (Promega) and λgt10 in vitro packaging kit (Amersham) according to the manufacturers' procedures. An amplified oligo (dT) primed human placenta λZAPII cDNA library of 5×10⁵ independent clones was used. Poly (A)⁺ RNA isolated from AG1518 human foreskin fibroblasts was used to prepare a primary random primed λZAPII cDNA library of 1.5×10⁶ independent clones using the RiboClone cDNA synthesis system and Gigapack Gold II packaging extract (Stratagene). In addition, a primary oligo (dT) primed human foreskin fibroblast λgt10 cDNA library (Claesson-Welsh et al (1989) Proc. Natl. Acad. Sci. USA. 86 4917-4912) was prepared. An amplified oligo (dT) primed HEL cell λgt11 cDNA library of 1.5×10⁶ independent clones (Poncz et al (1987) Blood 69 219-223) was used. A twelve-day mouse embryo λEXIox cDNA library was obtained from Novagen (Madison, Wis., U.S.A.); a mouse placenta λZAPII cDNA library was also used.

Generation of cDNA Probes by PCR

For the generation of cDNA probes by PCR (Lee et al (1988) Science 239, 1288-1291) degenerate PCR primers were constructed based upon the amino-acid sequence similarity between the mouse activin type II receptor (Mathews and Vale (1991) Cell 65, 973-982) and daf-1 (George et al (1990) Cell 61, 635-645) in the kinase domains II and VIII. FIG. 1 shows the aligned serine/threonine kinase domains (1-VIII), of four related receptors of the TGF-β superfamily, i.e. hTβR-II, mActR-IIB, mActR-II and the daf-1 gene product, using the nomenclature of the subdomains according to Hanks et al (1988) Science 241, 45-52.

Several considerations were applied in the design of the PCR primers. The sequences were taken from regions of homology between the activin type II receptor and the daf-1 gene product, with particular emphasis on residues that confer serine/threonine specificity (see Table 2) and on residues that are shared by transmembrane kinase proteins and not by cytoplasmic kinases. The primers were designed so that each primer of a PCR set had an approximately similar GC composition, and so that self complementarity and complementarity between the 3' ends of the primer sets were avoided. Degeneracy of the primers was kept as low as possible, in particular avoiding serine, leucine and arginine residues (6 possible codons), and human codon preference was applied. Degeneracy was particularly avoided at the 3' end as, unlike the 5' end, where mismatches are tolerated, mismatches at the 3' end dramatically reduce the efficiency of PCR.

In order to facilitate directional subcloning, restriction enzyme sites were included at the 5' end of the primers, with a GC clamp, which permits efficient restriction enzyme digestion. The primers utilised are shown in FIG. 2. Oligonucleotides were synthesized using Gene assembler plus (Pharmacia—LKB) according to the manufacturers instructions.

The mRNA prepared from HEL cells as described above was reverse-transcribed into cDNA in the presence of 50 mM Tris-HCl, pH 8.3, 8 mM $MgCl_2$, 30 mM KCl, 10 mM dithiothreitol, 2 mM nucleotide triphosphates, excess oligo (dT) primers and 34 units of AMV reverse transcriptase at 42° C. for 2 hours in 40 μl of reaction volume. Amplification by PCR was carried out with a 7.5% aliquot (3 μl) of the reverse-transcribed mRNA, in the presence of 10 mM Tris-HCl, pH 8.3, 50 mM KCl, 1.5 M $MgCl_2$, 0.01% gelatin, 0.2 mM nucleotide triphosphates, 1 μM of both sense and antisense primers and 2.5 units of Taq polymerase (Perkin Elmer Cetus) in 100 μl reaction volume. Amplifications were performed on a thermal cycler (Perkin Elmer Cetus) using the following program: first 5 thermal cycles with denaturation for 1 minute at 94° C., annealing for 1 minute at 50° C., a 2 minute ramp to 55° C. and elongation for 1 minute at 72° C., followed by 20 cycles of 1 minute at 94° C., 30 seconds at 55° C. and 1 minute at 72° C. A second round of PCR was performed with 3 μl of the first reaction as a template. This involved 25 thermal cycles, each composed of 94° C. (1 min), 55° C. (0.5 min), 72° C. (1 min).

General procedures such as purification of nucleic acids, restriction enzyme digestion, gel electrophoresis, transfer of nucleic acid to solid supports and subcloning were performed essentially according to established procedures as described by Sambrook et al, (1989), Molecular cloning: A Laboratory Manual, $2^{nd}$ Ed. Cold Spring Harbor Laboratory (Cold Spring Harbor, N.Y., USA).

Samples of the PCR products were digested with BamHI and EcoRI and subsequently fractionated by low melting point agarose gel electrophoresis. Bands corresponding to the approximate expected sizes, (see Table 1: ≈460 bp for primer pair B3-S and E8-AS and ≈140 bp for primer pair B7-S and E8-AS) were excised from the gel and the DNA was purified. Subsequently, these fragments were ligated into pUC19 (Yanisch-Perron et al (1985) Gene 33, 103-119), which had been previously linearised with BamHI and EcoRI and transformed into E. coli strain DH5α using standard protocols (Sambrook et al, supra). Individual clones were sequenced using standard double-stranded sequencing techniques and the dideoxynucleotide chain termination method as described by Sanger et al (1977) Proc. Natl. Acad. Sci. USA 74, 5463-5467, and T7 DNA polymerase.

Employing Reverse Transcriptase PCR on HEL mRNA with the primer pair B3-S and E8-AS, three PCR products were obtained, termed 11.1, 11.2 and 11.3, that corresponded to novel genes. Using the primer pair B7-S and E8-AS, an additional novel PCR product was obtained termed 5.2.

clones with approximate insert sizes of 1.7 kb, 2 kb & 3.5 kb were identified. The 2 kb clone, named HP57, was chosen as representative of this class and subjected to complete sequencing. Sequence analysis of ALK-1 revealed a sequence of 1984 nucleotides including a poly-A tail (SEQ ID No. 1). The longest open reading frame encodes a protein of 503 amino-acids, with high sequence similarity to receptor serine/threonine kinases (see below). The first methionine codon, the putative translation start site, is at nucleotide 283-285 and is preceded by an in-frame stop codon. This first ATG is in a more favourable context for translation initiation (Kozak (1987) Nucl. Acids Res., 15, 8125-8148) than the second and third in-frame ATG at nucleotides 316-318 and 325-327. The putative initiation codon is preceded by a 5' untranslated sequence of 282 nucleotides that is GC-rich (80% GC), which is not uncommon for growth factor receptors (Kozak (1991) J. Cell Biol., 115, 887-903). The 3' untranslated sequence comprises 193 nucleotides and ends with a poly-A tail. No bona fide poly-A addition signal is found, but there is a sequence (AATACA), 17-22 nucleotides upstream of the poly-A tail, which may serve as a poly-A addition signal.

TABLE 1

| NAME OF PCR PRODUCT | PRIMERS | INSERT SITE (bp) | SITE OF DNA FRAGMENT IN mActRII/hTBRII CLONES (bp) | SEQUENCE IDENTITY WITH SEQUENCE mActRII/hTBRII (%) | SEQUENCE IDENTITY BETWEEN mActRII and TBR-11 (%) |
|---|---|---|---|---|---|
| 11.1 | B3-S/E8-AS | 460 | 460 | 46/40 | 42 |
| 11.2 | B3-S/E8-AS | 460 | 460 | 49/44 | 47 |
| 11.3 | B3-S/E8-AS | 460 | 460 | 44/36 | 48 |
| 11.29 | B3-S/E8-AS | 460 | 460 | ND/100 | ND |
| 9.2 | B1-S/E8-AS | 800 | 795 | 100/ND | ND |
| 5.2 | B7-S/E8-AS | 140 | 143 | 40/38 | 60 |

Isolation of cDNA Clones

The PCR products obtained were used to screen various cDNA libraries described supra. Labelling of the inserts of PCR products was performed using random priming method (Feinberg and Vogelstein (1983) Anal. Biochem, 132 6-13) using the Megaprime DNA labelling system (Amersham). The oligonucleotide derived from the sequence of the PCR product 5.2 was labelled by phosphorylation with T4 polynucleotide kinase following standard protocols (Sambrook et al, supra). Hybridization and purification of positive bacteriophages were performed using standard molecular biological techniques.

The double-stranded DNA clones were all sequenced using the dideoxynucleotide chain-termination method as described by Sanger et al, supra, using T7 DNA polymerase (Pharmacia—LKB) or Sequenase (U.S. Biochemical Corporation, Cleveland, Ohio, U.S.A.). Compressions of nucleotides were resolved using 7-deaza-GTP (U.S. Biochemical Corp.) DNA sequences were analyzed using the DNA STAR computer program (DNA STAR Ltd. U.K.). Analyses of the sequences obtained revealed the existence of six distinct putative receptor serine/threonine kinases which have been named ALK 1-6.

To clone cDNA for ALK-1 the oligo (dT) primed human placenta cDNA library was screened with a radiolabelled insert derived from the PCR product 11.3; based upon their restriction enzyme digestion patterns, three different types of ALK-2 cDNA was cloned by screening an amplified oligo (dT) primed human placenta cDNA library with a radiolabelled insert derived from the PCR product 11.2. Two clones, termed HP53 and HP64, with insert sizes of 2.7 kb and 2.4 kb respectively, were identified and their sequences were determined. No sequence difference in the overlapping clones was found, suggesting they are both derived from transcripts of the same gene.

Sequence analysis of cDNA clone HP53 (SEQ ID No. 3) revealed a sequence of 2719 nucleotides with a poly-A tail. The longest open reading frame encodes a protein of 509 amino-acids. The first ATG at nucleotides 104-106 agrees favourably with Kozak's consensus sequence with an A at position 3. This ATG is preceded in-frame by a stop codon. There are four ATG codons in close proximity further downstream, which agree with the Kozak's consensus sequence (Kozak, supra), but according to Kozak's scanning model the first ATG is predicted to be the translation start site. The 5' untranslated sequence is 103 nucleotides. The 3' untranslated sequence of 1089 nucleotides contains a polyadenylation signal located 9-14 nucleotides upstream from the poly-A tail. The cDNA clone HP64 lacks 498 nucleotides from the 5' end compared to HP53, but the sequence extended at the 3' end with 190 nucleotides and poly-A tail is absent. This suggests that different polyadenylation sites occur for ALK-2. In Northern blots, however, only one transcript was detected (see below).

The cDNA for human ALK-3 was cloned by initially screening an oligo (dT) primed human foreskin fibroblast cDNA library with an oligonucleotide (SEQ ID No. 23) derived from the PCR product 5.2. One positive cDNA clone with an insert size of 3 kb, termed 0N11, was identified. However, upon partial sequencing, it appeared that this clone was incomplete; it encodes only part of the kinase domain and lacks the extracelluar domain. The most 5' sequence of ON11, a 540 nucleotide XbaI restriction fragment encoding a truncated kinase domain, was subsequently used to probe a random primed fibroblast cDNA library from which one cDNA clone with an insert size of 3 kb, termed 0NF5, was isolated (SEQ ID No. 5). Sequence analysis of ONF5 revealed a sequence of 2932 nucleotides without a poly-A tail, suggesting that this clone was derived by internal priming. The longest open reading frame codes for a protein of 532 amino-acids. The first ATG codon which is compatible with Kozak's consensus sequence (Kozak, supra), is at 310-312 nucleotides and is preceded by an in-frame stop codon. The 5' and 3' untranslated sequences are 309 and 1027 nucleotides long, respectively.

ALK-4 cDNA was identified by screening a human oligo (dT) primed human erythroleukemia cDNA library with the radiolabelled insert of the PCR product 11.1 as a probe. One cDNA clone, termed 11H8, was identified with an insert size of 2 kb (SEQ ID No. 7). An open reading frame was found encoding a protein sequence of 383 amino-acids encoding a truncated extracellular domain with high similarity to receptor serine/threonine kinases. The 3' untranslated sequence is 818 nucleotides and does not contain a poly-A tail, suggesting that the cDNA was internally primed. cDNA encoding the complete extracellular domain (nucleotides 1-366) was obtained from HEL cells by RT-PCR with 5' primer (SEQ ID No. 24) derived in part from sequence at translation start site of SKR-2 (a cDNA sequence deposited in GenBank data base, accesion number L10125, that is identical in part to ALK-4) and 3' primer (SEQ ID No. 25) derived from 11H8 cDNA clone.

ALK-5 was identified by screening the random primed HEL cell λgt 10 cDNA library with the PCR product 11.1 as a probe. This yielded one positive clone termed EMBLA (insert size of 5.3 kb with 2 internal EcoRI sites). Nucleotide sequencing revealed an open reading frame of 1509 bp, coding for 503 amino-acids. The open reading frame was flanked by a 5' untranslated sequence of 76 bp, and a 3' untranslated sequence of 3.7 kb which was not completely sequenced. The nucleotide and deduced amino-acid sequences of ALK-5 are shown in SEQ ID Nos. 9 and 10. In the 5' part of the open reading frame, only one ATG codon was found; this codon fulfils the rules of translation initiation (Kozak, supra). An in-frame stop codon was found at nucleotides (−54)-(−52) in the 5' untranslated region. The predicted ATG start codon is followed by a stretch of hydrophobic amino-acid residues which has characteristics of a cleavable signal sequence. Therefore, the first ATG codon is likely to be used as a translation initiation site. A preferred cleavage site for the signal peptidase, according to von Heijne (1986) Nucl. Acid. Res. 14, 4683-4690, is located between amino-acid residues 24 and 25. The calculated molecular mass of the primary translated product of the ALK-5 without signal sequence is 53,646 Da.

Screening of the mouse embryo λEX Iox cDNA library using PCR, product 11.1 as a probe yielded 20 positive clones. DNAs from the positive clones obtained from this library were digested with EcoRI and HindIII, electrophoretically separated on a 1.3% agarose gel and transferred to nitrocellulose filters according to established procedures as described by Sambrook et al, supra. The filters were then hybridized with specific probes for human ALK-1 (nucleotide 288-670), ALK-2 (nucleotide 1-581), ALK-3 (nucleotide 79-824) or ALK-4 nucleotide 1178-1967). Such analyses revealed that a clone termed ME-7 hybridised with the human ALK-3 probe. However, nucleotide sequencing revealed that this clone was incomplete, and lacked the 5' part of the translated region. Screening the same cDNA library with a probe corresponding to the extracelluar domain of human ALK-3 (nucleotides 79-824) revealed the clone ME-D. This clone was isolated and the sequence was analyzed. Although this clone was incomplete in the 3' end of the translated region, ME-7 and ME-D overlapped and together covered the complete sequence of mouse ALK-3. The predicted amino-acid sequence of mouse ALK-3 is very similar to the human sequence; only 8 amino-acid residues differ (98% identity; see SEQ ID No. 14) and the calculated molecular mass of the primary translated product without the putative signal sequence is 57,447 Da.

Of the clones obtained from the initial library screening with PCR product 11.1, four clones hybridized to the probe corresponding to the conserved kinase domain of ALK-4 but not to probes from more divergent parts of ALK-1 to -4. Analysis of these clones revealed that they have an identical sequence which differs from those of ALK-1 to -5 and was termed ALK-6. The longest clone ME6 with a 2.0 kb insert was completely sequenced yielding a 1952 bp fragment consisting of an open reading frame of 1506 bp (502 amino-acids), flanked by a 5' untranslated sequence of 186 bp, and a 3' untranslated sequence of 160 bp. The nucleotide and predicted amino-acid sequences of mouse ALK-6 are shown in SEQ ID Nos. 17 and 18. No polyadenylation signal was found in the 3' untranslated region of ME6, indicating that the cDNA was internally primed in the 3' end. Only one ATG codon was found in the 5' part of the open reading frame, which fulfils the rules for translation initiation (Kozak, supra), and was preceded by an in-frame stop codon at nucleotides 163-165. However, a typical hydrophobic leader sequence was not observed at the N terminus of the translated region. Since there is no ATG codon and putative hydrophobic leader sequence, this ATG codon is likely to be used as a translation initiation site. The calculated molecular mass of the primary translated product with the putative signal sequence is 55,576 Da.

Mouse ALK-1 (clone AM6 with 1.9 kb insert) was obtained from the mouse placenta λZAPII cDNA library using human ALK-1 cDNA as a probe (see SEQ ID No. 11). Mouse ALK-4 (clone 8a1 with 2.3 kb insert) was also obtained from this library using human ALK-4 cDNA library as a probe (SEQ ID No. 15).

To summarise, clones HP22, HP57, ONF1, ONF3, ONF4 and HP29 encode the same gene, ALK-1. Clone AM6 encodes mouse ALK-1. HP53, HP64 and HP84 encode the same gene, ALK-2. ONF5, ONF2 and ON11 encode the same gene ALK-3. ME-7 and ME-D encode the mouse counterpart of human ALK-3. 11H8 encodes a different gene ALK-4, whilst 8aI encodes the mouse equivalent. EMBLA encodes ALK-5, and ME-6 encodes ALK-6.

Figure 3:
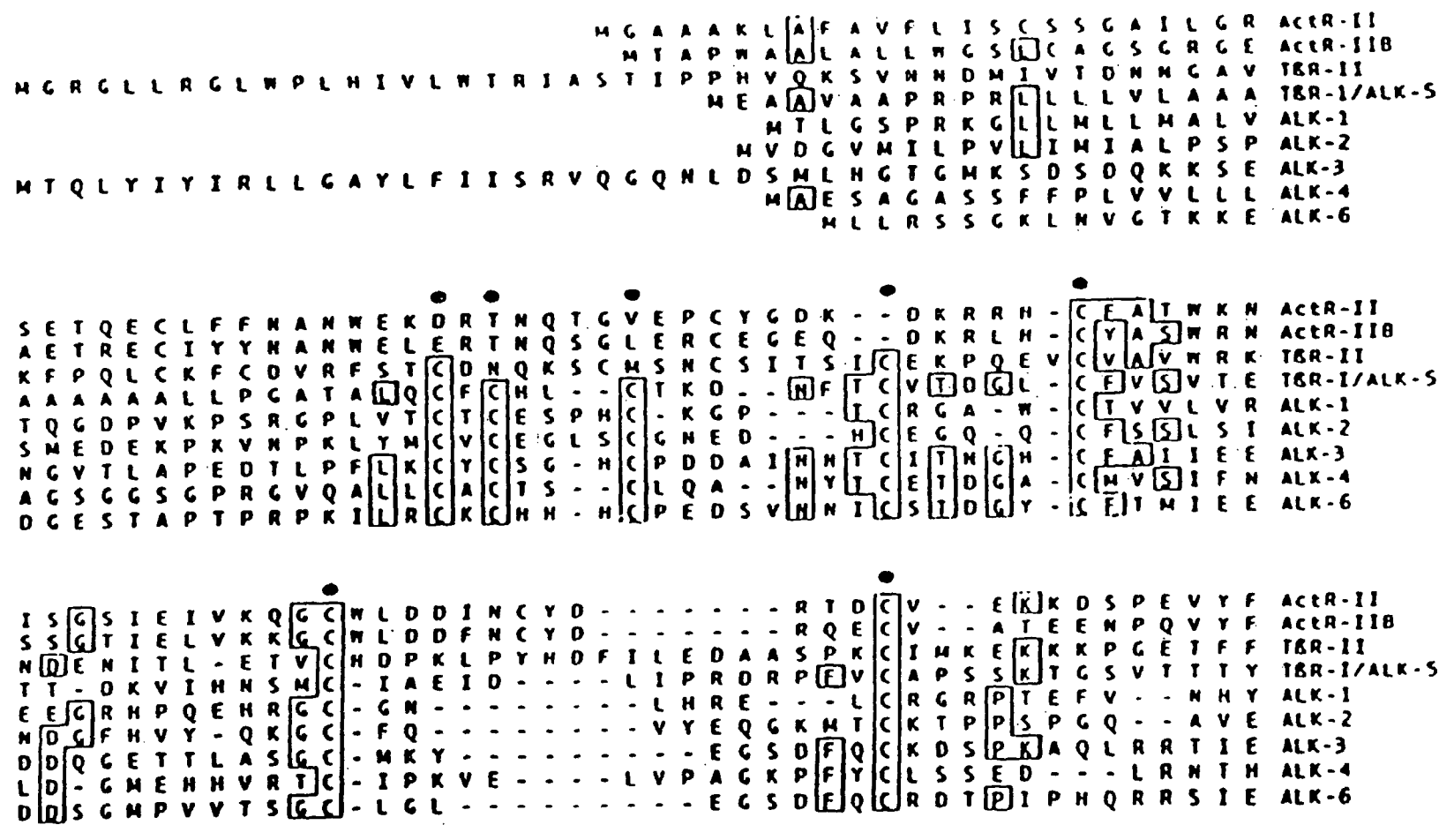

The sequence alignment between the 6 ALK genes and TβR-II, mActR-II and ActR-IIB is shown in FIG. 3. These molecules have a similar domain structure; an N-terminal predicted hydrophobic signal sequence (von Heijne (1986) Nucl. Acids Res. 14: 4683-4690) is followed by a relatively small extracellular cysteine-rich ligand binding domain, a single hydrophobic transmembrane region (Kyte & Doolittle (1982) J. Mol. Biol. 157, 105-132) and a C-terminal intracellular portion, which consists almost entirely of a kinase domain (FIGS. 3 and 4).

The extracelluar domains of these receptors have cysteine-rich regions, but they show little sequence similarity; for example, less than 20% sequence identity is found between Daf-1, ActR-II, TBR-II and ALK-5. The ALKs appear to form a subfamily as they show higher sequence similarities (15-47% identity) in their extracellular domains. The extracellular domains of ALK-5 and ALK-4 have about 29% sequence identity. In addition, ALK-3 and ALK-6 share a high degree of sequence similarity in their extracellular domains (46% identity).

Figure 5:
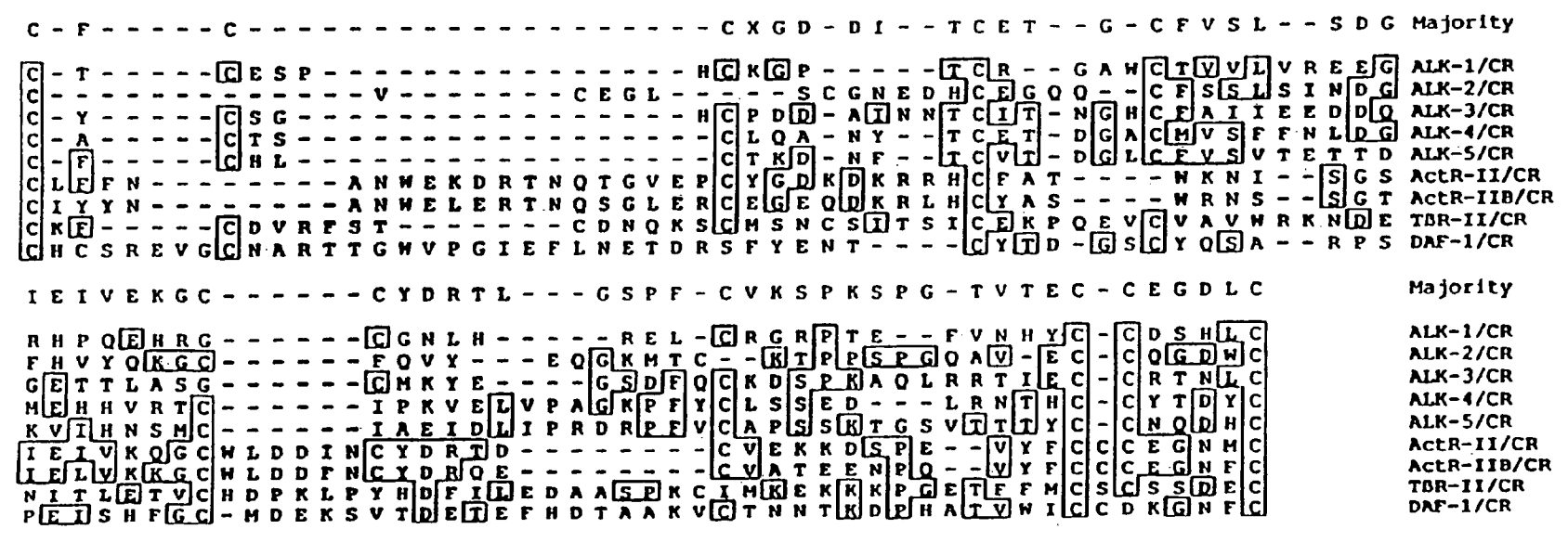

The positions of many of the cysteine residues in all receptors can be aligned, suggesting that the extracellular domains may adopt a similar structural configuration. See FIG. 5 for ALKs-1, -2, -3 & -5. Each of the ALKs (except ALK-6) has a potential N-linked glycosylation site, the position of which is conserved between ALK-1 and ALK-2, and between ALK-3, ALK-4 and ALK-5 (see FIG. 4).

The sequence similarities in the kinase domains between daf-1, ActR-II, TβR-II and ALK-5 are approximately 40%, whereas the sequence similarity between the ALKs 1 to 6 is higher (between 59% and 90%; see FIG. 6). Pairwise comparison using the Jutun-Hein sequence alignment program (Hein (1990) Meth, Enzymol., 183, 626-645), between all family members, identifies the ALKs as a separate subclass among serine/threonine kinases (FIG. 7).

The catalytic domains of kinases can be divided into 12 subdomains with stretches of conserved amino-acid residues. The key motifs are found in serine/threonine kinase receptors suggesting that they are functional kinases. The consensus sequence for the binding of ATP (Gly-X-Gly-X-X-Gly in subdomain I followed by a Lys residue further downstream in subdomain II) is found in all the ALKs.

The kinase domains of daf-1, ActR-II, and ALKs show approximately equal sequence similarity with tyrosine and serine/threonine protein kinases. However analysis of the amino-acid sequences in subdomains VI and VIII, which are the most useful to distinguish a specificity for phosphorylation of tyrosine residues versus serine/threonine residues (Hanks et al (1988) Science 241 42-52) indicates that these kinases are serine/threonine kinases; refer to Table 2.

TABLE 2

| KINASE | SUBDOMAINS (SEQ ID NOS: ) | |
|---|---|---|
| | VIB | VIII |
| Serine/threonine kinase consensus | DLKPEN 35 | G (T/S) XX (Y/F) X 37-40 |
| Tyrosine kinase consensus | DLAAFN 36 | XP (I/V) (K/R) W (T/M) 41-48 |
| Act R-II | DIKSKN Amino acids 322-327 of SEQ ID NO: 30 | GTRRYM Amino acids 361-366 of SEQ ID NO: 30 |
| Act R-III | DFKSKN Amino acids 345-350 of SEQ ID NO: 31 | GTRRYM Amino acids 361-366 of SEQ ID NO: 31 |
| TyR-II | DLKSSN Amino acids | GTARYM Amino acids |

TABLE 2-continued

| KINASE | SUBDOMAINS (SEQ ID NOS: ) | |
|---|---|---|
| | VIB | VIII |
| | 379-384 of SEQ ID NO: 32 | 420-425 of SEQ ID NO: 32 |
| ALK-I | DFKSRN Amino acids 330-335 of SEQ ID NO: 3 | GTKRYM 29 |
| ALK-2, -3, -4, -5, & -6 | DLKSKN 28 | GTKRYM 29 |

The sequence motifs DLKSKN (Subdomain VIB) and GTKRYM (Subdomain VIII), that are found in most of the serine/threonine kinase receptors, agree well with the consensus sequences for all protein serine/threonine kinase receptors in these regions. In addition, these receptors, except for ALK-1, do not have a tyrosine residue surrounded by acidic residues between subdomains VII and VIII, which is common for tyrosine kinases. A unique characteristic of the members of the ALK serine/threonine kinase receptor family is the presence of two short inserts in the kinase domain between subdomains VIA and VIB and between subdomains X and XI. In the intracellular domain, these regions, together with the juxtamembrane part and C-terminal tail, are the most divergent between family members (see FIGS. 3 and 4). Based on the sequence similarity with the type II receptors for TGF-β and activin, the C termini of the kinase domains of ALKs-1 to -6 are set at Ser-495, Ser-501, Ser-527, Gln-500, Gln-498 and Ser-497, respectively.

mRNA Expression

The distribution of ALK-1, -2, -3, -4 was determined by Northern blot analysis. A Northern blot filter with mRNAs from different human tissues was obtained from Clontech (Palo Alto, Calif.). The filters were hybridized with $^{32}$P-labelled probes at 42° C. overnight in 50% formaldehyde, 5× standard saline citrate (SSC; 1×SSC is 50 mM sodium citrate, pH 7.0, 150 mM NaCl), 0.1% SDS, 50 mM sodium phosphate, 5×Denhardt's solution and 0.1 mg/ml salmon sperm DNA. In order to minimize cross-hybridization, probes were used that did not encode part of the kinase domains, but corresponded to the highly diverged sequences of either 5' untranslated and ligand-binding regions (probes for ALK-1, -2 and -3) or 3' untranslated sequences (probe for ALK-4). The probes were labelled by random priming using the Multiprime (or Mega-prime) DNA labelling system and [α-$^{32}$P] dCTP (Feinberg & Vogelstein (1983) Anal. Biochem. 132: 6-13). Unincorporated label was removed by Sephadex G-25 chromatography. Filters were washed at 65° C., twice for 30 minutes in 2.5×SSC, 0.1% SDS and twice for 30 minutes in 0.3×SSC, 0.1% SDS before being exposed to X-ray film. Stripping of blots was performed by incubation at 90-100° C. in water for 20 minutes.

The ALK-5 mRNA size and distribution were determined by Northern blot analysis as above. An EcoRl fragment of 980 bp of the full length ALK-5 cDNA clone, corresponding to the C-terminal part of the kinase domain and 3' untranslated region (nucleotides 1259-2232 in SEQ ID No. 9) was used as a probe. The filter was washed twice in 0.5×SSC, 0.1% SDS at 55° C. for 15 minutes.

Using the probe for ALK-1, two transcripts of 2.2 and 4.9 kb were detected. The ALK-1 expression level varied strongly between different tissues, high in placenta and lung, moderate in heart, muscle and kidney, and low (to not detectable) in brain, liver and pancreas. The relative ratios between the two transcripts were similar in most tissues; in kidney, however, there was relatively more of the 4.9 kb transcript. By reprobing the blot with a probe for ALK-2, one transcript of 4.0 kb was detected with a ubiquitous expression pattern. Expression was detected in every tissue investigated and was highest in placenta and skeletal muscle. Subsequently the blot was reprobed for ALK-3. One major transcript of 4.4 kb and a minor transcript of 7.9 kb were detected. Expression was high in skeletal muscle, in which also an additional minor transcript of 10 kb was observed. Moderate levels of ALK-3 mRNA were detected in heart, placenta, kidney and pancreas, and low (to not detectable) expression was found in brain, lung and liver. The relative ratios between the different transcripts were similar in the tested tissues, the 4.4 kb transcript being the predominant one, with the exception for brain where both transcripts were expressed at a similar level. Probing the blot with ALK-4 indicated the presence of a transcript with the estimated size of 5.2 kb and revealed an ubiquitous expression pattern. The results of Northern blot analysis using the probe for ALK-5 showed that a 5.5 kb transcript is expressed in all human tissues tested, being most abundant in placenta and least abundant in brain and heart.

The distribution of mRNA for mouse ALK-3 and -6 in various mouse tissues was also determined by Northern blot analysis. A multiple mouse tissue blot was obtained from Clontech, Palo Alto, Calif., U.S.A. The filter was hybridized as described above with probes for mouse ALK-3 and ALK-6. The EcoRI-PstI restriction fragment, corresponding to nucleotides 79-1100 of ALK-3, and the SacI-HpaI fragment, corresponding to nucleotides 57-720 of ALK-6, were used as probes. The filter was washed at 65° C. twice for 30 minutes in 2.5×SSC, 0.1% SDS and twice for 30 minutes with 0.3× SSC, 0.1% SDS and then subjected to autoradiography.

Using the probe for mouse ALK-3, a 1.1 kb transcript was found only in spleen. By reprobing the blot with the ALK-6 specific probe, a transcript of 7.2 kb was found in brain and a weak signal was also seen in lung. No other signal was seen in the other tissues tested, i.e. heart, liver, skeletal muscle, kidney and testis.

All detected transcript sizes were different, and thus no cross-reaction between mRNAs for the different ALKs was observed when the specific probes were used. This suggests that the multiple transcripts of ALK-1 and ALK-3 are coded from the same gene. The mechanism for generation of the different transcripts is unknown at present; they may be formed by alternative mRNA splicing, differential polyadenylation, use of different promotors, or by a combination of these events. Differences in mRNA splicing in the regions coding for the extracellular domains may lead to the synthesis of receptors with different affinities for ligands, as was shown for mActR-IIB (Attisano et al (1992) Cell 68, 97-108) or to the production of soluble binding protein.

The above experiments describe the isolation of nucleic acid sequences coding for new family of human receptor kinases. The cDNA for ALK-5 was then used to determine the encoded protein size and binding properties.

Properties of the ALKs cDNA Encoded Proteins

To study the properties of the proteins encoded by the different ALK cDNAs, the cDNA for each ALK was subcloned into a eukaryotic expression vector and transfected into various cell types and then subjected to immunoprecipitation using a rabbit antiserum raised against a synthetic peptide corresponding to part of the intracellular juxtamembrane region. This region is divergent in sequence between the various serine/threonine kinase receptors. The following amino-acid residues were used:

| | |
|---|---|
| ALK-1 | 145-166 |
| ALK-2 | 151-172 |
| ALK-3 | 181-202 |
| ALK-4 | 153-171 |
| ALK-5 | 158-179 |
| ALK-6 | 151-168 |

The rabbit antiseru against ALK-5 was designated VPN.

The peptides were synthesized with an Applied Biosystems 430A Peptide Synthesizer using t-butoxycarbonyl chemistry and purified by reversed-phase high performance liquid chromatography. The peptides were coupled to keyhole limpet haemocyanin (Calbiochem-Behring) using glutaraldehyde, as described by Guillick et al (1985) EMBO J. 4, 2869-2877. The coupled peptides were mixed with Freunds adjuvant and used to immunize rabbits.

Transient Transfection of the ALK-5 cDNA

COS-1 cells (American Type Culture Collection) and the R mutant of MvlLu cells (for references, see below) were cultured in Dulbecco's modified Eagle's medium containing 10% fetal bovine serum (FBS) and 100 units/ml penicillin and 50 µg 1 ml streptomycin in 5% $CO_2$ atmosphere at 37° C. The ALK-5 cDNA (nucleotides (−76)-2232), which includes the complete coding region, was cloned in the pSV7d vector (Truett et al, (1985) DNA 4, 333-349), and used for transfection. Transfection into COS-1 cells was performed by the calcium phosphate precipitation method (Wigler et al (1979) Cell 16, 777-785). Briefly, cells were seeded into 6-well cell culture plates at a density of $5 \times 10^5$ cells/well, and transfected the following day with 10 µg of recombinant plasmid. After overnight incubation, cells were washed three times with a buffer containing 25 mM Tris-HCl, pH 7.4, 138 mM NaCl, 5 mM KCl, 0.7 mM $CaCl_2$, 0.5 mM $MgCl_2$ and 0.6 mM $Na_2HPO_4$, and then incubated with Dulbecco's modified Eagle's medium containing FBS and antibiotics. Two days after transfection, the cells were metabolically labelled by incubating the cells for 6 hours in methionine and cysteine-free MCDB 104 medium with 150 µCi/ml of [$^{35}$S]-methionine and [$^{35}$S]-cysteine (in vivo labelling mix; Amersham). After labelling, the cells were washed with 150 mM NaCl, 25 mM Tris-HCl, pH 7.4, and then solubilized with a buffer containing 20mM Tris-HCl, pH 7.4, 150 mM NaCl, 10 mM EDTA, 1% Triton X-100, 1% deoxycholate, 1.5% Trasylol (Bayer) and 1 mM phenylmethylsulfonylfluoride (PMSF; Sigma). After 15 minutes on ice, the cell lysates were pelleted by centrifugation, and the supernatants were then incubated with 7 µl of preimmune serum for 1.5 hours at 4° C. Samples were then given 50 µl of protein A-Sepharose (Pharmacia-LKB) slurry (50% packed beads in 150 mM NaCl, 20 mM Tris-HCl, pH 7.4, 0.2% Triton X100) and incubated for 45 minutes at 4° C. The beads were spun down by centrifugation, and the supernatants (1 ml) were then incubated with either 7 µl of preimmune serum or the VPN antiserum for 1.5 hours at 4° C. For blocking, 10 µg of peptide was added together with the antiserum. Immune complexes were then given 50 µl of protein A-Sepharose (Pharmacia—LKB) slurry (50% packed beads in 150 mM NaCl, 20mM Tris-HCl, pH 7.4, 0.2% Triton X-100) and incubated for 45 minutes at 4° C. The beads were spun down and washed four times with a washing buffer (20 mM Tris-HCl, pH 7.4, 500 mM NaCl, 1% Triton X-100, 1% deoxycholate and 0.2% SDS), followed by one wash in distilled water. The immune complexes were eluted by boiling for 5 minutes in the SDS-sample buffer (100 mM Tris-HCl, pH 8.8, 0.01% bromophenol blue, 36% glycerol, 4% SDS) in the presence of 10 mM DTT, and analyzed by SDS-gel electrophoresis using 7-15% polyacrylamide gels (Blobel and Dobberstein, (1975) J. Cell Biol. 67, 835-851). Gels were fixed, incubated with Amplify (Amersham) for 20 minutes, and subjected to fluorography. A component of 53 Da was seen. This component was not seen when preimmune serum was used, or when 10 μg blocking peptide was added together with the antiserum. Moreover, it was not detectable in samples derived from untransfected COS-1 cells using either preimmune serum or the antiserum.

Digestion with Endoglycosidase F

Samples immunoprecipitated with the VPN antisera obtained as described above were incubated with 0.5 U of endoglycosidase F (Boehringer Mannheim Biochemica) in a buffer containing 100 mM sodium phosphate, pH 6.1, 50 mM EDTA, 1% Triton X-100, 0.1% SDS and 1% β-mercaptoethanol at 37° C. for 24 hours. Samples were eluted by boiling for 5 minutes in the SDS-sample buffer, and analyzed by SDS-polyacrylamide gel electrophoresis as described above. Hydrolysis of N-linked carbohydrates by endoglycosidase F shifted the 53 kDa band to 51 kDa. The extracelluar domain of ALK-5 contains one potential acceptor site for N-glycosylation and the size of the deglycosylated protein is close to the predicted size of the core protein.

Establishment of PAE Cell Lines Expressing ALK-5

In order to investigate whether the ALK-5 cDNA encodes a receptor for TGF-β, porcine aortic endothelial (PAE) cells were transfected with an expression vector containing the ALK-5 cDNA, and analyzed for the binding of $^{125}$I-TGF-β1.

PAE cells were cultured in Ham's F-12 medium supplemented with 10% FBS and antibiotics (Miyazono et al., (1988) J. Biol. Chem. 263, 6407-6415). The ALK-5 cDNA was cloned into the cytomegalovirus (CMV)-based expression vector pcDNA I/NEO (Invitrogen), and transfected into PAE cells by electroporation. After 48 hours, selection was initiated by adding Geneticin (G418 sulphate; Gibco—BRL) to the culture medium at a final concentration of 0.5 mg/ml (Westermark et al, (1990) Proc. Natl. Acad. Sci. USA 87, 128-132). Several clones were obtained, and after analysis by immunoprecipitation using the VPN antiserum, one clone denoted PAE/TβR-1 was chosen and further analyzed.

Iodination of TGF-β1, Binding and Affinity Crosslinking

Recombinant human TGF-β1 was iodinated using the chloramine T method according to Frolik et al., (1984) J. Biol. Chem. 259, 10995-11000. Cross-linking experiments were performed as previously described (Ichijo et al., (1990) Exp. Cell Res. 187, 263-269). Briefly, cells in 6-well plates were washed with binding buffer (phosphate-buffered saline containing 0.9 mM $CaCl_2$, 0.49 mM $MgCl_2$ and 1 mg/ml bovine serum albumin (BSA)), and incubated on ice in the same buffer with $^{125}$I-TGF-β1 in the presence or absence of excess unlabelled TGF-β1 for 3 hours. Cells were washed and cross-linking was done in the binding buffer without BSA together with 0.28 mM disuccinimidyl suberate (DSS; Pierce Chemical Co.) for 15 minutes on ice. The cells were harvested by the addition of 1 ml of detachment buffer (10 mM Tris-HCl, pH 7.4, 1 mM EDTA, 10% glycerol, 0.3 mM PMSF). The cells were pelleted by centrifugation, then resuspended in 50 μl of solubilization buffer (125 mM NaCl, 10 mM Tris-HCl, pH 7.4, 1 mM EDTA, 1% Triton X-100, 0.3 mM PMSF, 1% Trasylol) and incubated for minutes on ice. Cells were centrifuged again and supernatants were subjected to analysis by SDS-gel electrophoresis using 4-15% polyacrylamide gels, followed by autoradiography. $^{125}$I-TGF-β1 formed a 70 kDa cross-linked complex in the transfected PAE cells (PAE/TβR-I cells). The size of this complex was very similar to that of the TGF-β type I receptor complex observed at lower amounts in the untransfected cells. A concomitant increase of 94 kDa TGF-β type II receptor complex could also be observed in the PAE/TfiR-I cells. Components of 150-190 kDa, which may represent crosslinked complexes between the type I and type II receptors, were also observed in the PAE/TβR-I cells.

In order to determine whether the cross-linked 70 kDa complex contained the protein encoded by the ALK-5 cDNA, the affinity cross-linking was followed by immunoprecipitation using the VPN antiserum. For this, cells in 25 $cm^2$ flasks were used. The supernatants obtained after cross-linking were incubated with 7 μl of preimmune serum or VPN antiserum in the presence or absence of 10 μg of peptide for 1.5 h at 4° C. Immune complexes were then added to 50 μl of protein A-Sepharose slurry and incubated for 45 minutes at 4° C. The protein A-Sepharose beads were washed four times with the washing buffer, once with distilled water, and the samples were analyzed by SDS-gel electrophoresis using 4-15% polyacrylamide gradient gels and autoradiography. A 70 kDa cross-linked complex was precipitated by the VPN antiserum in PAE/TβR-1 cells, and a weaker band of the same size was also seen in the untransfected cells, indicating that the untransfected PAE cells contained a low amount of endogenous ALK-5. The 70 kDa complex was not observed when preimmune serum was used, or when immune serum was blocked by 10 μg of peptide. Moreover, a coprecipitated 94 kDa component could also be observed in the PAE/TBR-I cells. The latter component is likely to represent a TGF-β type II receptor complex, since an antiserum, termed DRL, which was raised against a synthetic peptide from the C-terminal part of the TGF-β type II receptor, precipitated a 94 kDa TGF-β type II receptor complex, as well as a 70 kDa type I receptor complex from PAE/TβR-I cells.

The carbohydrate contents of ALK-5 and the TGF-β type II receptor were characterized by deglycosylation using endoglycosidase F as described above and analyzed by SDS-polyacrylamide gel electrophoresis and autoradiography. The ALK-5 cross-linked complex shifted from 70 kDa to 66 kDa, whereas that of the type II receptor shifted from 94 kDa to 82 kDa. The observed larger shift of the type II receptor band compared with that of the ALK-5 band is consistent with the deglycosylation data of the type I and type II receptors on rat liver cells reported previously (Cheifetz et al (1988) J. Biol. Chem. 263, 16984-16991), and fits well with the fact that the porcine TGF-β type II receptor has two N-glycosylation sites (Lin et al (1992) Cell 68, 775-785), whereas ALK-5 has only one (see SEQ ID No. 9).

Binding of TGF-β1 to the type I receptor is known to be abolished by transient treatment of the cells with dithiothreitol (DTT) (Cheifetz and Massague (1991) J. Biol. Chem. 266, 20767-20772; Wrana et al (1992) Cell 71, 1003-1014). When analyzed by affinity cross-linking, binding of $^{125}$I-TGF-β1 to ALK-5, but not to the type II receptor, was completely abolished by DTT treatment of PAE/TβR-1 cells. Affinity cross-linking followed by immunoprecipitation by the VPN antiserum showed that neither the ALK-5 nor the type II receptor complexes was precipitated after DTT treatment, indicating that the VPN antiserum reacts only with ALK-5. The data show that the VPN antiserum recognizes a TGF-β type I receptor, and that the type I and type II receptors form a heteromeric complex.

$^{125}$I-TGF-1 Binding & Affinity Crosslinking of Transfected COS Cells

Transient expression plasmids of ALKs-1 to -6 and TβR-II were generated by subcloning into the pSV7d expression vector or into the pcDNA I expression vector (Invitrogen).

Transient transfection of COS-1 cells and iodination of TGF-β1 were carried out as described above. Crosslinking and immunoprecipitation were performed as described for PAE cells above.

Transfection of cDNAs for ALKs into COS-1 cells did not show any appreciable binding of $^{125}$I-TGFβ1, consistent with the observation that type I receptors do not bind TGF-β in the absence of type II receptors. When the TβR-II cDNA was co-transfected with cDNAs for the different ALKs, type I receptor-like complexes were seen, at different levels, in each case. COS-1 cells transfected with TβR-II and ALK cDNAs were analyzed by affinity crosslinking followed by immunoprecipitation using the DRL antisera or specific antisera against ALKs. Each one of the ALKs bound $^{125}$I-TGF-β1 and was coimmunoprecipitated with the TβR-II complex using the DRL antiserum. Comparison of the efficiency of the different ALKs to form heteromeric complexes with TβR-II, revealed that ALK-5 formed such complexes more efficiently than the other ALKs. The size of the crosslinked complex was larger for ALK-3 than for other ALKs, consistent with its slightly larger size.

Expression of the ALK Protein in Different Cell Types

Two different approaches were used to elucidate which ALK's are physiological type I receptors for TGF-β.

Firstly, several cell lines were tested for the expression of the ALK proteins by cross-linking followed by immunoprecipitation using the specific antiseras against ALKs and the TGF-β type II receptor. The mink lung epithelial cell line, MvlLu, is widely used to provide target cells for TGF-β action and is well characterized regarding TGF-β receptors (Laiho et al (1990) J. Biol. Chem. 265, 18518-18524; Laiho et al (1991) J. Biol. Chem. 266, 9108-9112). Only the VPN antiserum efficiently precipitated both type I and type II TGF-β receptors in the wild type MvlLu cells. The DRL antiserum also precipitated components with the same size as those precipitated by the VPN antiserum. A mutant cell line (R mutant) which lacks the TGF-β type I receptor and does not respond to TGF-β (Laiho et al, supra) was also investigated by cross-linking followed by immunoprecipitation. Consistent with the results obtained by Laiho et al (1990), supra the type III and type II TGF-β receptor complexes, but not the type I receptor complex, were observed by affinity crosslinking. Crosslinking followed by immunoprecipatition using the DRL antiserum revealed only the type II receptor complex, whereas neither the type I nor type II receptor complexes was seen using the VPN antiserum. When the cells were metabolically labelled and subjected to immunoprecipitation using the VPN antiserum, the 53 kDa ALK-5 protein was precipitated in both the wild-type and R mutant MvlLu cells. These results suggest that the type I receptor expressed in the R mutant is ALK-5, which has lost the affinity for binding to TGF-β after mutation.

The type I and type II TGF-β receptor complexes could be precipitated by the VPN and DRL antisera in other cell lines, including human foreskin fibroblasts (AG1518), human lung adenocarcinoma cells (A549), and human oral squamous cell carcinoma cells (HSC-2). Affinity cross-linking studies revealed multiple TGF-β type I receptor-like complexes of 70-77 kDa in these cells. These components were less efficiently competed by excess unlabelled TGF-β1 in HSC-2 cells. Moreover, the type II receptor complex was low or not detectable in A549 and HSC-cells. Cross-linking followed by immunoprecipitation revealed that the VPN antiserum precipitated only the 70 kDa complex among the 70-77 kDa components. The DRL antiserum precipitated the 94 kDa type II receptor complex as well as the 70 kDa type I receptor complex in these cells, but not the putative type I receptor complexes of slightly larger sizes. These results suggest that multiple type I TGF-β receptors may exist and that the 70 kDa complex containing ALK-5 forms a heteromeric complex with the TGF-β type II receptor cloned by Lin et al (1992) Cell 68, 775-785, more efficiently that the other species. In rat pheochromocytoma cells (PC12) which have been reported to have no TGF-β receptor complexes by affinity cross-linking (Massague et al (1990) Ann. N.Y. Acad. Sci. 593, 59-72), neither VPN nor DRL antisera precipitated the TGF-β receptor complexes. The antisera against ALKs-1 to -4 and ALK6 did not efficiently immunoprecipitate the crosslinked receptor complexes in porcine aortic endothelial (PAE) cells or human foreskin fibroblasts.

Next, it was investigated whether ALKs could restore responsiveness to TGF-β in the R mutant of MvlLu cells, which lack the ligand-binding ability of the TGF-β type I receptor but have intact type II receptor. Wild-type MvlLu cells and mutant cells were transfected with ALK cDNA and were then assayed for the production of plasminogen activator inhibitor-1 (PAI-1) which is produced as a result of TGF-β receptor activation as described previously by Laiho et al (1991) Mol. Cell Biol. 11, 972-978. Briefly, cells were added with or without 10 ng/ml of TGF-β1 for 2 hours in serum-free MCDB 104 without methionine. Thereafter, cultures were labelled with [$^{35}$S] methionine (40 µCi/ml) for 2 hours. The cells were removed by washing on ice once in PBS, twice in 10 mM Tris-HCl (pH 8.0), 0.5% sodium deoxycholate, 1 mM PMSF, twice in 2 mM Tris-HCl (pH 8.0), and once in PBS. Extracellular matrix proteins were extracted by scraping cells into the SDS-sample buffer containing DTT, and analyzed by SDS-gel electrophoresis followed by fluorography using Amplify. PAI-1 can be identified as a characteristic 45kDa band (Laiho et al (1991) Mol. Cell Biol. 11, 972-978). Wild-type MvlLu cells responded to TGF-β and produced PAI-1, whereas the R mutant clone did not, even after stimulation by TGF-β1. Transient transfection of the ALK-5 cDNA into the R mutant clone led to the production of PAI-1 in response to the stimulation by TGF-β1, indicating that the ALK-5 cDNA encodes a functional TGF-β type I receptor. In contrast, the R mutant cells that were transfected with other ALKs did not produce PAI-1 upon the addition of TGF-β1.

Using similar approaches as those described above for the identification of TGF-β-binding ALKs, the ability of ALKs to bind activin in the presence of ActRII was examined. COS-1 cells were co-transfected as described above. Recombinant human activin A was iodinated using the chloramine T method (Mathews and Vale (1991) Cell 65, 973-982). Transfected COS-1 cells were analysed for binding and crosslinking of I-activin A in the presence or absence of excess unlabelled activin A. The crosslinked complexes were subjected to immunoprecipitation using DRL antisera or specific ALK antisera.

All ALKs appear tc bind activin A in the presence of Act R-II. This is more clearly demonstrated by affinity cross-linking followed by immunopreciptation. ALK-2 and ALK-4 bound $^{125}$I-activin A and were coimmunoprecipitated with ActR-II. Other ALKs also bound 125I-activin A but with a lower efficiency compared to ALK-2 and ALK-4.

In order to investigate whether ALKs are physiological activin type I receptors, activin responsive cells were examined for the expression of endogenous activin type I receptors. MvlLu cells, as well as the R mutant, express both type I and type II receptors for activin, and the R mutant cells produce PAI-1 upon the addition of activin A. MvlLu cells were labeled with $^{125}$I-activin A, cross-linked and immunoprecipitated by the antisera against ActR-II or ALKs as described above.

The type I and type II receptor complexes in MvlLu cells were immunoprecipitated only by the antisera against ALK-2, ALK-4 and ActR-II. Similar results were obtained using the R mutant cells. PAE cells do not bind activin because of the lack of type II receptors for activin, and so cells were transfected with a chimeric receptor, to enable them to bind activin, as described herein. A plasmid (chim A) containing the extracelluar domain and C-terminal tail of Act R-II (amino-acids −19 to 116 and 465 to 494, respectively (Mathews and Vale (1991) Cell, 65., 973-982)) and the kinase domain of TBR-II (amino-acids 160-543) (Lin et al (1992) Cell, 68, 775-785) was constructed and transfected into pcDNA/neo (Invitrogen). PAE cells were stably transfected with the chim A plasmid by electroporation, and cells expressing the chim A protein were established as described previously. PAE/Chim A cells were then subjected to $^{125}$I-activin A labelling crosslinking and immunoprecipitation as described above.

Similar to MvlLu cells, activin type I receptor complexes in PAE/Chim A cells were immunoprecipitated by the ALK-2 and ALK-4 antisera. These results show that both ALK-2 and ALK-4 serve as high affinity type I receptors for activin A in these cells.

ALK-1, ALK-3 and ALK-6 bind TGF-β1 and activin A in the presence of their respective type II receptors, but the functional consequences of the binding of the ligands remains to be elucidated.

The invention has been described by way of example only, without restriction of its scope. The invention is defined by the subject matter herein, including the claims that follow the immediately following full Sequence Listings.

The invention claimed is:

1. An isolated antibody which binds specifically to an amino acid sequence encoded by the nucleotide sequence set forth in SEQ ID NO: 5 (ALK-3).

2. The isolated antibody of claim 1, wherein the antibody bind specifically to the amino sequence of SEQ ID NO: 6.

3. The isolated antibody of claim 1, wherein the antibody binds specifically to an extracellular domain of a human protein encoded by the nucleotide sequence set forth in SEQ ID NO: 5.

4. The isolated antibody of claim 1, wherein the antibody binds specifically to amino acids 181-202 of SEQ ID NO: 6.

* * * * *